United States Patent
Rosen et al.

(10) Patent No.: US 9,715,506 B2
(45) Date of Patent: Jul. 25, 2017

(54) METADATA INJECTION OF CONTENT ITEMS USING COMPOSITE CONTENT

(71) Applicant: Smart Screen Networks, Inc., Encinitas, CA (US)

(72) Inventors: Stephen D. Rosen, San Diego, CA (US); John Stallings, San Diego, CA (US); Robert A. Strickland, San Diego, CA (US); Jeff Symon, San Diego, CA (US); Kyle David Strickland, San Diego, CA (US)

(73) Assignee: Smart Screen Networks, Inc., Encinitas, CA (US)

( * ) Notice: Subject to any disclaimer, the term of this patent is extended or adjusted under 35 U.S.C. 154(b) by 0 days.

(21) Appl. No.: 14/885,924

(22) Filed: Oct. 16, 2015

(65) Prior Publication Data

US 2017/0109349 A1    Apr. 20, 2017

(51) Int. Cl.
   *G06F 17/30* (2006.01)

(52) U.S. Cl.
   CPC ...... *G06F 17/3012* (2013.01); *G06F 17/3082* (2013.01); *G06F 17/30268* (2013.01)

(58) Field of Classification Search
   CPC .............................................. G06F 17/30657
   See application file for complete search history.

(56) References Cited

U.S. PATENT DOCUMENTS

| | | | | |
|---|---|---|---|---|
| 7,677,896 B1* | 3/2010 | Sonwalkar | ............... | G09B 7/00 434/236 |
| 2006/0230331 A1* | 10/2006 | Abanami | ............... | G06Q 30/02 715/234 |
| 2008/0243788 A1* | 10/2008 | Reztlaff | ............ | G06F 17/30657 |
| 2008/0269931 A1* | 10/2008 | Martinez | ........... | G06F 17/30026 700/94 |
| 2009/0157289 A1* | 6/2009 | Graessley | ................. | B60L 3/12 701/123 |
| 2011/0131497 A1* | 6/2011 | Goran | ................... | G06F 3/0481 715/723 |
| 2013/0076771 A1* | 3/2013 | Bachman | ........... | G06Q 30/0643 345/581 |
| 2013/0230205 A1* | 9/2013 | Nuggehalli | .......... | G06K 9/2054 382/100 |

* cited by examiner

*Primary Examiner* — Dinku Gebresenbet

(74) *Attorney, Agent, or Firm* — Procopio Cory Hargreaves and Savitch LLP; Pattric J. Rawlins; Jonathan Cheng

(57) ABSTRACT

Injection of metadata using composite content. In an embodiment, one or more content items are received, and data is retrieved from a plurality of metadata sources. A visual depiction of metadata is generated for at least one of the content item(s) based on the retrieved data. A composite content item is generated to comprise at least a portion of each of the content item(s) and the visual depiction of the metadata.

19 Claims, 9 Drawing Sheets

METADATA INJECTION OF CONTENT ITEMS USING COMPOSITE CONTENT

CROSS-REFERENCE TO RELATED APPLICATIONS

This application is related to U.S. patent application Ser. No. 14/731,260, filed Jun. 4, 2015, which is a continuation of U.S. patent application Ser. No. 14/323,738, filed Jul. 3, 2014 and issued as U.S. Pat. No. 9,058,375 on Jun. 16, 2015, which is a national stage entry of International Patent App. No. PCT/US2014/059764, and is also related to International Patent App. No. PCT/US2014/054383, the entireties of all of which are hereby incorporated herein by reference.

BACKGROUND

Field of the Invention

The embodiments described herein are generally directed to metadata, and, more particularly, to the addition of descriptive metadata to digital media.

Description of the Related Art

Digital media—generally referred to herein as "content"—can take a variety of forms, including images (e.g., JPEG, GIF, BMP, etc.), video recordings (e.g., MPEG-4, AVI, MOV, etc.), audio recordings (e.g., WAV, MP3, WMA, etc.), text (TXT, XML, HTML, etc.), combinations of different forms (e.g., Microsoft Word™, Microsoft Powerpoint™, Portable Document Format (PDF), etc.), and other forms of data. When content is owned and/or is associated with a right to use, the content may be referred to as a "digital asset." However, as used herein, the term "content" or "content item" (a specific instance of content) includes any type of media, regardless of whether or not it comprises a digital asset.

"Metadata," which is often defined as "data about data," is used herein to designate descriptive or technical information that is embedded in or otherwise associated with the data (e.g., file or files) embodying content. Technical metadata refers to information about the technical properties of the content, such as an identifier of the device that was used to capture the content, a resolution of the content, a timestamp representing the date and time on which the content was created and/or modified, a format of the content, etc. Descriptive metadata, on the other hand, refers to information describing the content, such as the names of individuals who appear in the content, an author or producer of the content, a rating of the content, a narrative description of the content, keywords that are relevant to the content, etc. Descriptive metadata is particularly useful for organizing, categorizing, and searching content. For example, a search engine may be configured to parse the descriptive metadata associated with a content item to determine whether the content item is relevant to a particular search query (e.g., if any text in the descriptive metadata match any keywords in the search query).

Currently, there are a number of commonly-used standards for storing metadata in association with content. For example, Exchangeable Image File Format (EXIF) is a standard that specifies the formats for images, sound, and ancillary tags used by digital cameras (including smart phones), scanners, and other media-capturing devices. EXIF defines a number of metadata tags or fields into which metadata, including technical and descriptive metadata, can be entered. In EXIF, metadata is embedded within the content file itself. Another example standard is the International Press Telecommunications Council (IPTC) Information Interchange Model (IIM), which has been largely superseded by the Extensible Metadata Platform (XMP). XMP is an open-source standard for the creation, processing, and interchange of standardized and custom metadata for all kinds of resources. XMP can be embedded in many types of file formats, such as JPEG, Tagged Image File Format (TIFF), and Portable Document Format (PDF), but can also be stored separately as a "sidecar" file to content. Generally, metadata stored using these formats comprise copyright information, credits, creation date, creation location, source information, comments, special format instructions, etc.

Whereas technical metadata can generally be automatically created and associated with content (e.g., during creation of the content), descriptive metadata is much less conducive to automatic generation and association. Conventionally, descriptive metadata must be manually entered and associated with content. For example, typically, for each individual content item, a content creator must select the content item and manually enter descriptive metadata to be associated with that content item, using a keyboard, touch pad, or other input device. For individuals or other entities (e.g., entertainment, film production, news, or broadcasting companies) that generate a lot of content, the generation and association of descriptive metadata with the created content can be inefficient, time-consuming, and otherwise burdensome.

For instance, with the advent of smart phones, tablets, and other digital devices and the decreasing cost of storage, the volume of content produced by users in the consumer market has exploded in recent years. A typical user of such devices may produce tens of thousands of content items. Over time, the majority of users do not bother to expend the effort necessary to manually add descriptive metadata to each content item. Furthermore, commonly-available applications, which may provide functions for adding metadata to content, do not provide the ability to add descriptive metadata in bulk. Instead, a user must wade through an ocean of content items and manually add descriptive metadata to each individual content item.

Moreover, conventional applications are not conducive to the addition of metadata in the moment. For example, many users take pictures in social situations, on vacations, during sporting events, and/or in other hurried environments, in which it is not convenient or appropriate for the user to stop for the length of time necessary to manually enter metadata. Thus, the entry of metadata is typically significantly delayed. This problem has been exacerbated with the advent of cameras with fast shutters, which can take multiple images per second, and which can produce hundreds of images in a short period of time. Content creators may often find themselves with hundreds or thousands of content items, each with generic names (e.g., assigned by the camera or other device), limited technical metadata, and little or no descriptive metadata.

The burden associated with manually entering metadata and the deficiencies in prior art applications has frustrated the ability of descriptive metadata to keep up with the ever-increasing volume of content that is generated today. In turn, this lack of descriptive metadata hinders the ability to search, organize, and enjoy such content. What are needed are improved processes and systems for adding descriptive metadata to content items. Embodiments should be user friendly, automatic or semi-automatic, and/or capable of being performed in bulk. Such improved processes and systems can facilitate the subsequent organization, sorting, and searching of the content items, thereby improving a user's experience of those content items.

SUMMARY

In an embodiment, a method is disclosed. The method comprises using at least one hardware processor to: receive one or more content items; retrieve data from a plurality of metadata sources; generate a visual depiction of metadata for at least one of the one or more content items based on the retrieved data; and generate a composite content item comprising at least a portion of each of the one or more content items and the visual depiction of the metadata.

In another embodiment, a system is disclosed. The system comprises: at least one hardware processor; and one or more software modules that, when executed by the at least one hardware processor, receive one or more content items, retrieve data from a plurality of metadata sources, generate a visual depiction of metadata for at least one of the one or more content items based on the retrieved data, and generate a composite content item comprising at least a portion of each of the one or more content items and the visual depiction of the metadata.

In another embodiment, a non-transitory computer-readable medium is disclosed. The medium has instructions stored thereon, wherein the instructions, when executed by a processor, cause the processor to: receive one or more content items; retrieve data from a plurality of metadata sources; generate a visual depiction of metadata for at least one of the one or more content items based on the retrieved data; and generate a composite content item comprising at least a portion of each of the one or more content items and the visual depiction of the metadata.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

In an embodiment, systems and methods are disclosed for adding descriptive metadata to content items, for example, to organize and facilitate searches for the content items once they are stored. As used herein, the terms "content," "content item," or "content items" may refer to any type of content, including, without limitation, images (e.g., photographs, collages, digital artwork, etc.), video recordings, audio recordings, animations, slideshows, electronic documents (e.g., spreadsheets, word-processing documents, PDF documents, etc.), etc. In embodiments, the addition of the descriptive metadata may be performed automatically or semi-automatically by a computing device, such as a smart phone, tablet, laptop, desktop, server, wearable device, drone, or other processing device.

After reading this description, it will become apparent to one skilled in the art how to implement the systems and methods in various alternative embodiments and alternative applications. However, although various embodiments will be described herein, it is understood that these embodiments are presented by way of example and illustration only, and not limitation. As such, this detailed description of various embodiments should not be construed to limit the scope or breadth of the present application as set forth in the appended claims.

1. System Overview
1.1. Infrastructure

Figure 1:
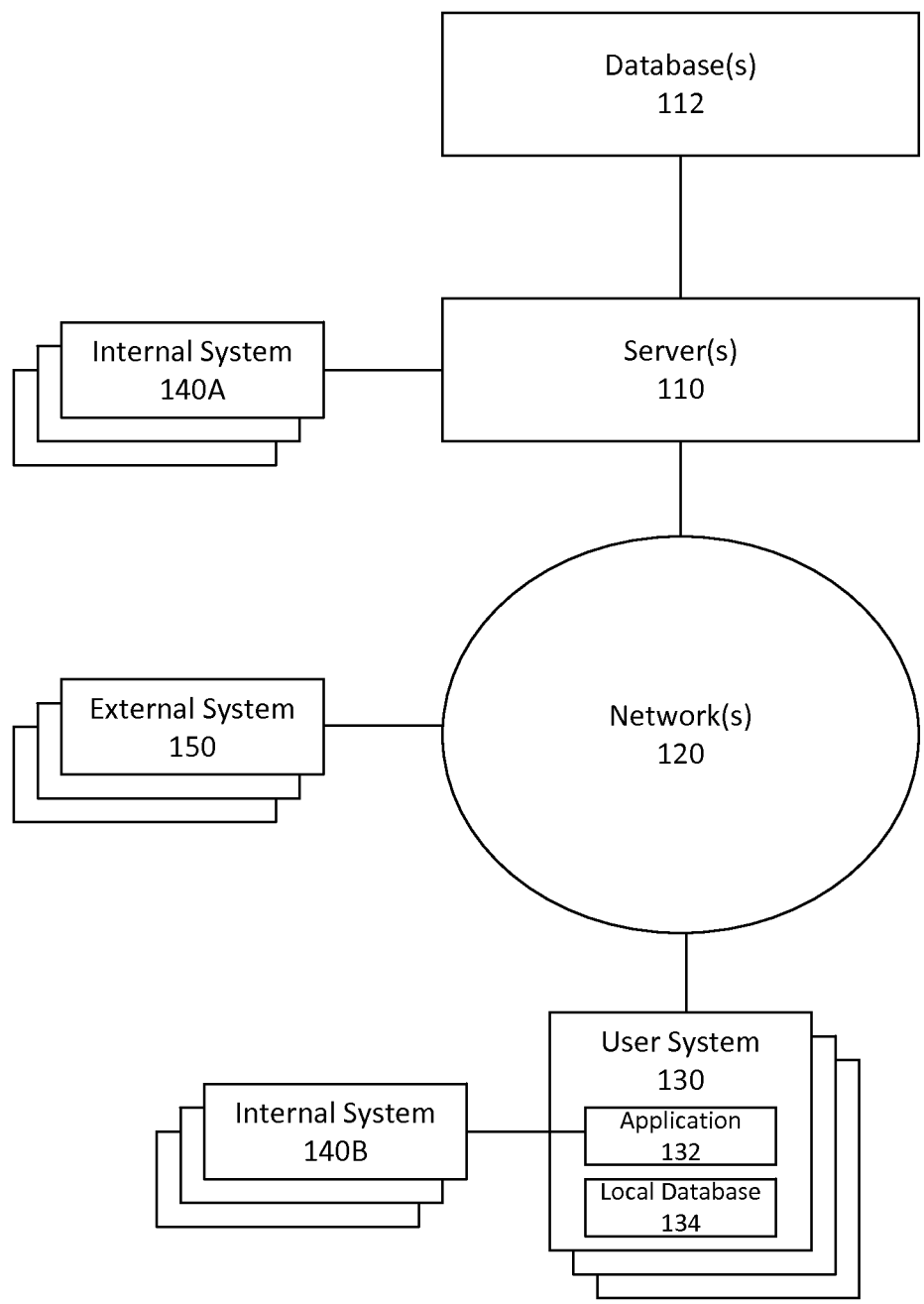
FIG. 1 illustrates an environment in which the disclosed systems, modules, and processes may operate, according to an embodiment.

FIG. 1 illustrates an example infrastructure in which the disclosed system may operate, according to an embodiment. The infrastructure may comprise one or more server(s) 110 to host and/or execute one or more of the various functions, processes, methods, and/or software modules described herein. Server(s) 110 may comprise one or more servers or cloud interfaces or instances, which utilize shared resources of one or more servers. In addition, the infrastructure may comprise one or more user systems 130 which host and/or execute one or more of the various functions, processes, methods, and/or software modules described herein. User system(s) 130 may host at least some modules of an application, according to embodiments disclosed herein, and/or a local database. Server(s) 110 may be communicatively connected to user system(s) 130 via one or more network(s) 120 and may also be communicatively connected to one or more database(s) 112 (e.g., via one or more network(s), such as network(s) 120) and/or may comprise one or more database(s) 112. In addition, server(s) 110 may be communicatively connected to (e.g., via an intranet) or comprise one or more internal systems 140, and/or may be communicatively connected to one or more external systems 150 via network(s) 120. Network(s) 120 may comprise the Internet, and server(s) 110 may communicate with user system(s) 130 and/or external system(s) 150 through the Internet using standard transmission protocols, such as HyperText Transfer Protocol (HTTP), Secure HTTP (HTTPS), File Transfer Protocol (FTP), FTP Secure (FTPS), Secure Shell FTP (SFTP), and the like, as well as proprietary protocols.

It should be understood that the components (e.g., servers, databases, and/or other resources) of server(s) 110 may be, but are not required to be, collocated. Furthermore, while server(s) 110 are illustrated as being connected to various systems through a single set of network(s) 120, it should be understood that server(s) 110 may be connected to the various systems via different sets of one or more networks. For example, server(s) 110 may be connected to a subset of user systems 130 via the Internet, but may be connected to one or more other user systems 130 via an intranet. It should also be understood that user system(s) 130 may comprise any type or types of computing devices, including without limitation, desktop computers, laptop computers, tablet computers, smart phones or other mobile phones, servers, wearable devices (e.g., Google Glass™, Apple Watch™, etc.), drones, game consoles, televisions, set-top boxes, electronic kiosks, and the like. Such user system(s) 130 may comprise image acquisition devices, such as a camera, scanner, and the like, which are able to acquire images, including photographs and/or video. While it is contemplated that such devices are capable of wired or wireless communication, this is not a requirement for all embodiments. In addition, while only a few user systems 130, a few internal systems 140, a few external systems 150, one set of server(s) 110, and one set of database(s) 112 are illustrated, it should be understood that the network may comprise any number of user system(s), internal system(s), external system(s), sets of server(s), and database(s), including, in some instances, zero (e.g., no external systems and/or no internal systems).

Server(s) 110 may comprise web servers which host one or more websites or web services. In embodiments in which a website is provided, the website may comprise one or more user interfaces, including, for example, webpages generated in HTML or other language. Server(s) 110 transmit or serve these user interfaces as well as other data (e.g., a downloadable copy of or installer for application 132) in response to requests from user system(s) 130. In some embodiments, these user interfaces may be served in the form of a wizard, in which case two or more user interfaces may be served in a sequential manner, and one or more of the sequential user interfaces may depend on an interaction of the user or user system with one or more preceding user interfaces. The requests to server(s) 110 and the responses from server(s) 110, including the user interfaces and other data, may both be communicated through network(s) 120, which may include the Internet, using standard communication protocols (e.g., HTTP, HTTPS). These user interfaces or web pages, as well as the user interfaces provided by application 132 executing on a user system 130, may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases that are locally and/or remotely accessible to user system(s) 130 and/or server(s) 110.

Server(s) 110 may further comprise, be communicatively coupled with, or otherwise have access to one or more database(s) 112. For example, server(s) 110 may comprise one or more database servers which manage one or more databases 112. A user system 130 or application executing on server(s) 110 may submit data (e.g., user data, form data, etc.) to be stored in database(s) 112, and/or request access to data stored in such database(s) 112. Any suitable database may be utilized, including without limitation MySQL™, Oracle™ IBM™, Microsoft SQL™, Sybase™, Access™, and the like, including cloud-based database instances and proprietary databases. Data may be sent to server(s) 110, for instance, using the well-known POST request supported by HTTP, via FTP, etc. This data, as well as other requests, may be handled, for example, by server-side web technology, such as a servlet or other software module, executed by server(s) 110.

In embodiments in which a web service is provided, server(s) 110 may receive requests from user system(s) 130, and provide responses in eXtensible Markup Language (XML) and/or any other suitable or desired format. In such embodiments, server(s) 110 may provide an application programming interface (API) which defines the manner in which user system(s) 130 may interact with the web service. Thus, user system(s) 130, which may themselves be servers, can define their own user interfaces, and rely on the web service to implement or otherwise provide the backend processes, methods, functionality, storage, etc., described herein. For example, in such an embodiment, a client application (e.g., application 132) executing on one or more user system(s) 130 may interact with a server application executing on server(s) 110 to execute one or more or a portion of one or more of the various functions, processes, methods, and/or software modules described herein. The client application may be "thin," in which case processing is primarily carried out server-side by platform 110. A basic example of a thin client application is a browser application, which simply requests, receives, and renders web pages at user system(s) 130, while server(s) 110 are responsible for generating the web pages and managing database functions. Alternatively, the client application may be "thick," in which case processing is primarily carried out client-side by user system(s) 130. It should be understood that the client application may perform an amount of processing, relative to server(s) 110, at any point along this spectrum between "thin" and "thick," depending on the design goals of the particular implementation. In any case, the application, which may wholly reside on either server(s) 110 or user system(s) 130 or be distributed between server(s) 110 and user system(s) 130, can comprise one or more executable software modules that implement one or more of the processes, methods, or functions of the application(s) described herein.

In an embodiment, server(s) 110 comprise or are communicatively connected to one or more internal systems 140A, and/or communicatively connected to one or more external systems 150. Server(s) may communicate with internal system(s) 140A and/or external system(s) 150 using standard communication protocols. Server(s) may "pull" information (e.g., metadata, data from which metadata is derived, etc.) from one or more of system(s) 140A and/or 150, for example, by sending a request for data to the system, and receiving the requested data in response to the request. Alternatively or additionally, one or more of system(s) 140A and/or 150 may "push" information (e.g., metadata, data from which metadata is derived, etc.) to server(s) 110 periodically (e.g., at a given frequency, such as every second, every hour, etc., in response to receiving updated data requested or otherwise indicated as desired by server(s) 110, etc.). As an example, system(s) 140A and/or 150 may stream such information to be used as metadata by server(s) 110 to server(s) 110 in real time. This information may include, without limitation, current weather data (e.g., temperature, humidity, wind speed, whether sunny, cloudy, rainy, snowy, etc.), outputs from medical monitoring devices (e.g., heartbeat, respiration, brain activity, etc.), outputs from other types of digital sensors, etc.

Additionally or alternatively, user system(s) 130 may comprise or be communicatively connected to one or more internal system(s) 140B, and/or communicatively connected to one or more external system(s) 150. These internal systems 140B and/or external systems 150 may operate in a similar or identical manner as system(s) 140 and 150 described above with respect to server(s) 110. For example, one or more user system(s) 130 may comprise or be interfaced with a temperature sensor, Global Positioning System (GPS) sensor, heartbeat monitor, etc. These integrated or interfaced systems may push or feed (e.g., periodically, in real time, etc.) information (e.g., metadata, data from which metadata may be derived, etc.) to such a user system 130, and/or return information (e.g., metadata, data from which metadata may be derived, etc.) to such a user system 130 in response to a request. In either case, the information may be provided to application 132, executing on user system 130, and/or may be stored temporarily or persistently in local database 134 on user system 130.

In an embodiment, user system 130 may generate metadata based on the received information from internal system(s) 140B and/or external system(s) 150, and/or provide the received information to server(s) 110 (e.g., to be used as or to generate metadata). Alternatively, server(s) 110 may generate metadata based on the received information from internal system(s) 140A, external system(s) 150, and/or user system(s) 130, and/or provide the received information to user system 130 (e.g., to be used as or to generate metadata by application 132).

It should be understood that each system 140A and 150 may provide different information (e.g., from different sources), which is aggregated at server(s) 110, and/or each system 140B and 150 may provide different information (e.g., from different sources), which is aggregated at user system 130. For example, one system 140A/140B or 150 may provide weather data, whereas a different system 140A/140B or 150 may provide an output from a medical monitoring device. Alternatively or additionally, two different systems 140A/140B or 150 may provide the same information (e.g., two or more systems each provide a temperature, and, for example, the average is used to derive metadata) or different information of the same type (e.g., one system provides a temperature while a different system provides a humidity). It should also be understood that each system 140A/140B or 150 may be operated by the same entity or different entities, and may be operated by the same entity as server(s) 110 and/or user system(s) 130 or a different entity than server(s) 110 and/or user system(s) 130.

1.2. Metadata Platform

Figure 2:
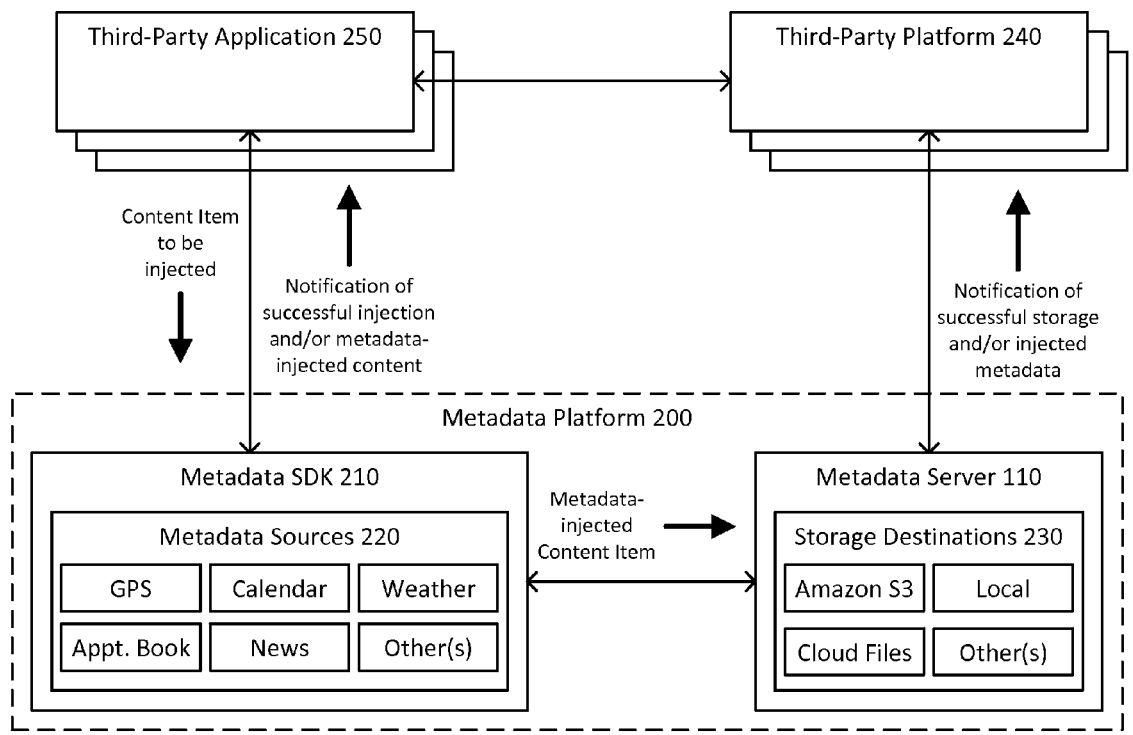
FIG. 2 illustrates the operation of a metadata platform with respect to third-party applications and platforms, according to an embodiment.

FIG. 2 illustrates an example of the operation of a metadata platform with respect to third-party applications and platforms, according to an embodiment. Metadata platform 200 aggregates, or facilitates aggregation of, descriptive metadata from a plurality of different metadata sources 220. As used with respect to disclosed embodiments, descriptive metadata may comprise text, Uniform Resource Identifiers (URIs), hyperlinks, images, charts, video, electronic documents, work orders, and any other type of data which is capable of being associated with a content item. In addition, the descriptive metadata may comprise a mash-up or other derivation of data from multiple metadata sources 220. As an example, metadata platform 200 may utilize location information from one metadata source 220 and a map image from a different metadata source 220 to derive metadata comprising a map image with an indication of the location, specified by the location information, within the map image. This plotted map image—which may represent a location at which a content item (e.g., photograph, video, or audio recording) was captured—may be associated with a content item as metadata.

For example, each of internal system(s) 140A and/or external system(s) 150 may function as metadata sources 220. Data may be received (e.g., either via a push or pull) from the system(s) 140 and/or 150, and descriptive metadata may be generated from the received data. The aggregated descriptive metadata may comprise the received data or be otherwise derived from the received data. For example, desired metadata may be extracted from the data received from source system(s) 140 and/or 150.

In addition, one or more content items (e.g., from a user system 130 or other external system over network(s) 120) may be received, and at least a portion of the aggregated descriptive metadata may be "injected" into the received content item(s). Injecting the metadata into a content item, as discussed herein, may comprise associating the metadata with the content item, for example, by adding the metadata to the content item (e.g., by embedding the metadata into one or more metadata fields within the content item) and/or adding the metadata to a sidecar file associated with the content item.

In an embodiment, the metadata may be associated with the content item by creating a composite content item that comprises a composite of one or more original content items and metadata associated with those content item(s). The composition of the original content item(s) with metadata may be in addition to the injection of metadata into embedded metadata fields within the composite content item or a sidecar file associated with the composite content item. For instance, a first subset or type of metadata may be used to create the composite content item, while a second subset or type of metadata (which may or may not overlap or be coextensive with the first subset or type of metadata) is added to embedded metadata fields or a sidecar file. As an example, if the metadata comprises an image (e.g., a map image with plotted location(s), as discussed elsewhere herein, another content item or captured image, etc.), the image may be combined with the original content item(s) to create a composite content item. For example, if the original content item is an image, the image from the metadata may be overlaid on a corner of the image of the original content item, or the image from the metadata and the image of the original content item may be arranged together in some other manner (e.g., side-by-side, top-and-bottom, etc.), to create a composite image as the composite content item. If the original content item is a video, the image from the metadata may be overlaid on or otherwise arranged with one or more frames of the video, to create a composite video as the composite content item. Additional metadata (e.g., an address of a location plotted in the image) may also be injected into an embedded field of the composite content item. In an embodiment, certain types of descriptive metadata (e.g., images, videos) that are not amenable to being input into embedded metadata fields (which are often only configured to accept text) may always be arranged with the original content item(s) to create a composite content item, whereas other types of descriptive metadata (e.g., text) that are amendable to being input into embedded metadata fields are embedded within those metadata fields.

In an embodiment, the composite content item may comprise a plurality of content items composed together (e.g., in a mash-up, collage, etc.). As one example, the composite content item may comprise images of a plurality of related assets (e.g., inventory assets). It should be understood that, in addition to a plurality of content items, the composite content item may also comprise one or a plurality of visual depictions of metadata and/or be associated with metadata via embedded or side-car fields, as discussed above.

In an embodiment, the composite content item may be defined by a template, which may comprise a selection of one or more content items and/or one or more visual depictions of metadata, and an arrangement of the selected content item(s) and/or visual depiction(s) of metadata. The arrangement may identify the position at which each of the selected content item(s) and/or visual depiction(s) of metadata are placed in the composite content item. A composite content item may then be generated based on the template, for example, by selecting content item(s) and/or visual depiction(s) of metadata identified in the template, and arranging the selected content item(s) and/or visual depiction(s) of metadata identified in the template according to the arrangement identified in the template.

Figure 9:
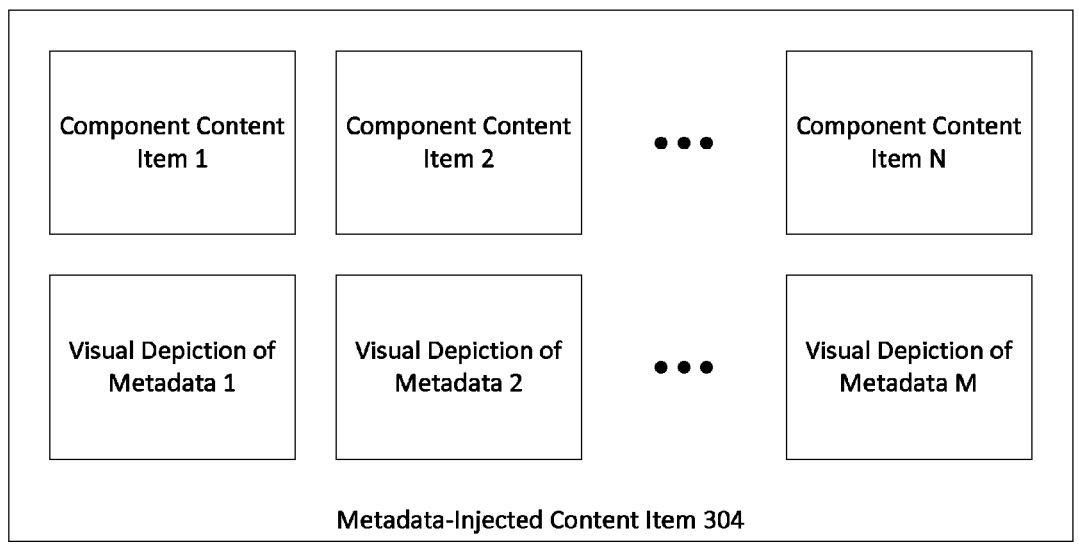
FIG. 9 illustrates a composite metadata-injected content item, according to an embodiment.

FIG. 9 illustrates a composite metadata-injected content item 304, according to an embodiment. As illustrated, composite metadata-injected content item 304 may comprise any number N (zero, one, two, three, four, and so on) of component content items and any number M (zero, one, two, three, four, and so on) of visual depictions of metadata. For example, the component content items could comprise any type of content item, including a digital image, a video, an electronic document, a third-party feed, etc. The component content item(s) may correspond one-to-one with original content item(s) 302, there may be multiple content items corresponding to a single original content item 302, and/or there may be no content item corresponding to a particular original content item 302. Similarly, the visual depiction(s) of metadata may include any type of visual element, such as a map image, a third-party or external feed (e.g., streaming video, a sensor feed), an asset identifier (e.g., asset number), an asset description (e.g., a text description of an asset), etc. The visual depiction(s) of metadata may correspond to one or more of original content item(s) 302. It should be understood that composite metadata-injected content item 304 may also comprise metadata that is not visually depicted (e.g., stored in embedded or otherwise associated fields of metadata-injected content item 304).

It should be understood that aggregation of the metadata from source system(s) 140 and/or 150 may be performed independently of when content item(s) are received or generated and/or may be performed in response to receiving or generating a content item. As a non-limiting example, weather data may be received on a periodic or real-time basis, and injected as metadata into content items, as those content items are received or generated. Alternatively, weather data may be requested when a content item is received or generated, and injected into the content item as metadata once the weather data is received in response to that request.

In an embodiment, after injecting metadata into a given content item, the content item with the injected metadata may be returned to the sender from which it was received (e.g., an originating application) and/or provided to an external or third-party system (e.g., over network(s) 120) for storage, publication, and/or the like. For example, after metadata is injected into a given content item, the metadata-injected content item may be stored locally and/or remotely in an external storage system (e.g., in the cloud).

1.2.1. Software Development Kit

In an embodiment, metadata platform 200 provides a metadata software development kit (SDK) 210, which may be utilized by one or more third-parties to design third-party applications. However, it should be understood that the metadata SDK 210 may also be utilized by the operator of metadata platform 200 (as opposed to a third-party) to design an application for a user system 130. Thus, as used herein the term "third party" or "third-party" may refer to any entity.

Metadata SDK 210 may comprise a set of software development tools that enables the creation of third-party applications. For example, a third-party developer may utilize metadata SDK 210, provided by platform 200, to design third-party application 250 (which may be the same as client application 132 in FIG. 1) for execution on user system(s) 130. Third-party application 250 may comprise module(s) and/or user interface(s) for capturing content items (e.g., by interfacing with a camera that captures an image or video) or otherwise generating content items.

In an embodiment, metadata SDK 210 may comprise one or more application programming interfaces (APIs) for interfacing with metadata sources 220. One or more APIs, provided by metadata SDK 210, may comprise a library (e.g., a specification for routines, data structures, object classes, variables, etc.). Alternatively or additionally, one or more APIs, provided by metadata SDK 210, may comprise a specification of remote calls to metadata sources 220 that may be utilized by a third-party application. For example, a third-party developer may incorporate calls (e.g., local or remote procedure calls) to metadata sources 220, in accordance with the specification in the API, into third-party application 250 which can be executed on a user system 130. In an embodiment, metadata SDK 210 may also comprise one or more APIs or libraries for interfacing with metadata server(s) 110.

In an embodiment, metadata SDK 210 may comprise one or more APIs for retrieving or otherwise receiving metadata from each of a plurality of potential metadata sources 220. Potential metadata source(s) 220 may include GPS, one or more calendar services (e.g., that provide real-time, near-real-time, and/or historical calendar data), one or more weather services (e.g., that provide real-time, near-real-time and/or historical weather data), one or more news services (e.g., that provide real-time, near-real-time, and/or historical news), one or more appointment applications (e.g., one or more third-party applications that keep track of appointments for registered users), one or more contact applications (e.g., one or more third-party applications that keep track of contacts for registered users), an object-recognition service or application (e.g., facial recognition, recognition of landmarks, products, pets, or other objects, etc.), a speech-to-text service or application (e.g., which generates closed-captions for content items comprising audio), one or more other services and/or applications (e.g., other third-party applications from which metadata may be derived), registration information (e.g., which returns authorship information based on data stored for a registered user), etc. A third-party developer may select any subset of one or more of metadata sources 220 to be used for metadata injection, according to its particular needs.

In addition, third-party developers may create custom sources using metadata SDK 210. For example, third-party developers may utilize metadata SDK 210 to generate custom modules (e.g., using a class specification or libraries in metadata SDK 210) for retrieving metadata from sources (e.g., other applications, services, etc.) that are not particularly provided for by metadata SDK 210.

It should be understood that the preceding list of potential sources is merely illustrative, and that metadata sources 220 may include more, fewer, and/or different sources than those described herein. In an embodiment, metadata sources 220 include the metadata sources described with respect to FIG. 3. Furthermore, the potential metadata sources 220 may be local to a user system 130 on which third-party application 250 is executing (e.g., another client application, such as a calendar or address book application, a GPS sensor, etc.), remote to the user system 130 on which third-party application 250 is executing (e.g., a weather service provided over network(s) 120), or a mixture of both local and remote sources.

1.2.2. Metadata Server

In an embodiment, metadata server(s) 110 may comprise or be interfaced with one or more potential storage destinations 230. Potential storage destination(s) 230 may include one or more remote storage destinations and/or one or more local storage destinations. One or more of these storage destinations may include a cloud storage destination (e.g., Amazon S3™). It should be understood that the list of potential storage destinations is merely illustrative, and that potential storage destinations 230 may include more, fewer, and/or different destinations than those described herein.

Metadata server(s) 110 may also be communicatively connected with one or more third-party platforms 240. Each third-party platform 240 may support (e.g., via communication, for example, over one or more networks such as network(s) 120) a respective third-party application 250. Each third-party application 250 may be a client application (e.g., application 132 executing on a user system 130), which communicates with a server of its respective third-party platform 240 (e.g., over network(s) 120), for example, for user registration and authentication, server-side processing, data storage, etc. It should be understood that, while only a few third-party applications 250 and a few third-party platforms 240 are illustrated, there may be any number of third-party application(s) 250 and third-party platform(s) 240, and each third-party platform 240 may support a plurality of third-party applications 250 executing on a plurality of user systems 130.

1.2.3. Metadata-Injection Module

Figure 3:
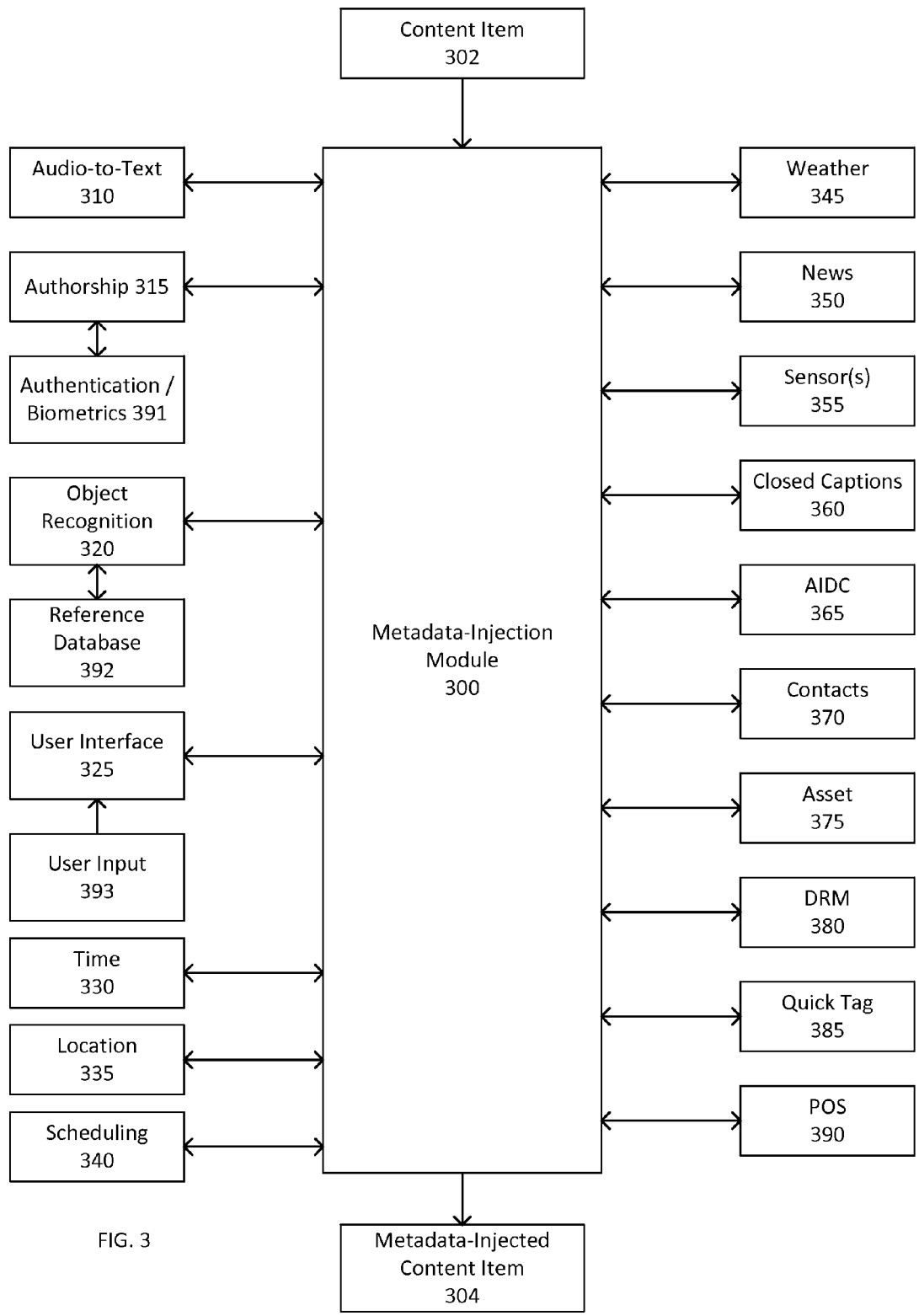
FIG. 3 illustrates a metadata injection module, according to an embodiment.

FIG. 3 illustrates a metadata-injection module 300, according to an embodiment. Metadata-injection module 300 may be implemented by a third party using metadata SDK 210. In this case, metadata-injection module 300 may be incorporated into third-party application 250. Alternatively, metadata-injection module 300 may be provided by metadata SDK 210 (e.g., as a pre-written library) and called by third-party application 250 as a routine specified in an API of metadata SDK 210. In this case, third-party application may pass the content item, to be injected with metadata, possibly with parameter(s), to metadata-injection module 300. Metadata-injection module 300 may execute on the same device (e.g., user system 130) as third-party application 250, or may execute on a device that is remote (e.g., over one or more networks, such as network(s) 120) from third-party application 250, such as metadata server 110 or third-party platform 240, in which case third-party application 250 may communicate with metadata-injection module 300 over one or more networks (e.g., network(s) 120) using standard communication protocols.

Metadata-injection module 300 comprises or is interfaced with one or more metadata sources, illustrated in FIG. 3 as sources 310, 315, 320, 325, 330, 335, 340, 345, 350, 355, 360, 365, 370, 375, and 380, which may correspond to metadata sources 220 in FIG. 2. However, it should be understood that these sources are merely illustrative, and that metadata-injection module 300 may comprise or be interfaced with fewer, more, or different sources than those shown. One or more of the sources may be local to metadata server 110 (e.g., on the same device as metadata-injection module 300, such as user system 130 or metadata server 110), or remote from metadata-injection module 300 (e.g., on a different device than metadata-injection module 300, for example, separated by network(s) 120 and/or a wireless network), in which case metadata-injection module 300 may communicate with those remote sources over one or more networks (e.g., network(s) 120) using standard communication protocols.

Each one of the metadata sources used by metadata-injection module 300 may be selected in advance by the particular third-party developer implementing or using metadata-injection module 300. For example, a given third-party developer may have a need for some metadata sources, but not others. In this case, the third-party developer may implement metadata-injection module 300 to utilize only the needed metadata sources, and not the unnecessary metadata sources, for example, by only utilizing the APIs and/or libraries of metadata SDK 210 related to the needed metadata sources. In addition, metadata SDK 210 may provide tools for a third-party developer to create its own custom metadata source. This extensibility allows a third-party developer to use any combination of the metadata sources provided by metadata SDK 210, its own metadata sources, and/or additional external metadata sources.

In an embodiment, third-party developers may pay for usage of the metadata sources (e.g., metadata sources 220, 310-390). In such an embodiment, metadata server 110 may comprise a web service which provides access to the metadata sources via one or more APIs. Third-party developers may register with metadata server 110 in advance. An accounting module may monitor which metadata source(s) each third-party developer uses via metadata server 110, and bill those third-party developers accordingly. In an embodiment, metadata server 110 may require authentication between third-party application 250 and metadata server 110 prior to utilization of the metadata sources accessible via metadata server 110. In this case, metadata server 110 may maintain a profile, for each third-party developer and/or third-party application 250, which identifies the metadata source(s) that that developer and/or application is authorized to use, and restrict each third-party application's use of metadata sources to those metadata source(s) identified in its respective profile or the profile of its developer.

Metadata-injection module 300 receives a content item 302 (e.g., from or through third-party application 250), consults at least a subset of the metadata sources to generate metadata, injects or otherwise associates the generated metadata with content item 302, and outputs metadata-injected content item 304 which corresponds to content item 302 with newly-associated metadata. Metadata-injection module 300 may receive at least some content item(s) 302, in real time or near-real time, as they are created (e.g., immediately after a photograph has been captured or a video recorded, for example, by third-party application 250). Thus, for example, metadata may be injected by metadata-injection module 300, in the background (e.g., automatically or semi-automatically), into content item(s) 302 before the content item(s) 302 are stored to persistent memory. Alternatively or additionally, metadata-injection module 300 may receive at least some content item(s) 302 at a time well after they were created, thereby allowing a user to inject metadata into old or historic content items.

In an embodiment, metadata-injection module 300 determines which of the metadata sources to retrieve metadata from based, at least in part, on the type of content item 302 (e.g., photograph, video, etc.). This content item type may be specified in the request comprising content item 302 and received by metadata-injection module 300, or may be determined by metadata-injection module 300 through analysis of content item 302. Metadata-injection module 300 may send a request, comprising an indication of the content item type, to each metadata source, and receive a response, comprising an indication of whether that metadata source supports that content item type, from the metadata source. Alternatively or additionally, metadata-injection module 300 may store associations between each metadata source and the content item type(s) that it supports. In this case, these associations may be updated (e.g., automatically, periodically, manually, etc.) by sending a request to each metadata source to be updated, and receiving a response comprising the content item type(s) that the metadata source supports. When metadata-injection module 300 receives a content item 302, metadata-injection module 300 may query the stored associations between content types and metadata sources, using the content item type, to identify all of the metadata source(s) that support the content item type. In any case, metadata-injection module 300 may only retrieve metadata from the metadata sources which support the type of content item 302.

In an embodiment, metadata-injection module 300 may consult some metadata sources 220 to retrieve metadata based on a time (e.g., represented as a timestamp) associated with content item 302. For example, this time may represent a time that content item 302 was received or created, or may be an arbitrary time that is associated with content item 302 (e.g., by a user or device). The time may be sent or passed to one or more of metadata sources 220 as a parameter, and may be used by the one or more metadata sources 220 to retrieve time-based metadata. It should be understood that where the time represents a time that content item 302 was created, a timestamp in the technical metadata of content item 302 may be used. In this case, metadata-injection module 300 does not need to receive content item 302 at or near the time of its creation, but may instead receive an old content item that may have been created long ago (e.g., either by the same device, or after being transferred from another device) and process the old content item in the same manner as it would a newly-created content item. Thus, the modules and processes described herein may apply to content items regardless of when and where they were generated.

Metadata-injection module 300 may be described herein as receiving metadata from the various metadata sources (e.g., metadata sources 220 and 310-390). However, it should be understood that the receipt of metadata by metadata-injection module 300 or return of metadata to metadata-injection module 300 by a metadata source may also refer to an instance in which information (which the metadata source may not necessarily intend to be used as metadata) is received by metadata-injection module 300 from a metadata source, and metadata-injection module 300 then derives metadata from that received information. For example, metadata-injection module 300 may derive metadata from information received from a metadata source by extracting character strings from the non-metadata information to be used as metadata, and then inject that metadata into content item 302 to produce metadata-injected content item 304. Injection may comprise inputting the metadata into embedded metadata fields of content item 302, inputted the metadata into a sidecar file associated with content item 302, generating a composite content item comprising both the original content item 302 and a visual depiction (e.g., image) of metadata, and/or otherwise associated the metadata with content item 302.

Each of the various potential metadata sources 310-390 will now be described in more detail. For each of metadata sources 310-390, metadata-injection module 300 may retrieve the information (e.g., metadata) automatically (e.g., without user input), semi-automatically (e.g., after user confirmation, for example, in response to a prompt of a user interface), or manually (e.g., in response to a specific user input or request). It should be understood that metadata sources 310-390 merely represent some examples of metadata sources, and metadata-injection module 300 may retrieve metadata from fewer, more, or different metadata sources, including custom metadata sources that are implemented by a third-party developer (e.g., specifically for a particular third-party application 250).

1.2.3.1. Audio-to-Text Module

In an embodiment, metadata-injection module 300 retrieves text information from an audio-to-text module 310. In cases in which content item 302 comprises audio data, this audio data may be sent from metadata-injection module 300 to audio-to-text module 310. For instance, the audio data may be extracted from content item 302, and the extracted audio data may be sent by metadata-injection module 300 to audio-to-text module 310. Alternatively, the entire content item 302 may be sent from metadata-injection module 300 to audio-to-text module 310, and audio-to-text module 310 may extract the audio data from content item 302. It should be understood that extraction or separation of the audio data from content item 302 may not be necessary, for example, if content item 302 consists only of the audio data (e.g., content item 302 is an audio recording).

The audio data may represent audio recorded by a microphone (e.g., integrated into a user system 130, such as a smartphone or camera, which may function as a capture device) during the capture of a content item, such as a video or audio recording. In this case, the audio data may reflect speech or ambient noise from one or more people or objects within or near a scene being captured. Alternatively or additionally, the audio data may represent audio recorded by such a microphone before or after capture of the content item. In this case, the audio data may represent audio recorded by someone (e.g., the person that captured or is about to capture the content item, or a person who possesses the content item), specifically to be used as metadata (e.g., a narration or other description of the content item), and this audio data may be attached to or otherwise associated with content item 302.

In any case, audio-to-text module 310 may convert the audio data from content item 302 into text, using well-known methods of speech-to-text conversion. In the case that the audio data is captured during capture of content item 302, the output text may reflect subtitles (e.g., closed captions) for content item 302. These subtitles may be associated with content item 302 (e.g., timed to the audio data in content item 302) by audio-to-text module 310 or metadata-injection module 300, such that they can be used as closed captions during playback of content item 302 (e.g., by a media player that supports closed captions). For example, if content item 302 comprises a video of two people having a conversation, the audio channel from the video may be extracted by metadata-injection module 300 and passed to audio-to-text module 310. Audio-to-text module 310 may convert the audio channel, representing the conversation, into text, and pass that text back to metadata-injection module 300, which may embed it into the metadata of content item 302.

In an embodiment, audio-to-text module 310 may be language agnostic (e.g., comprise libraries for all languages or a smaller subset of languages), such that it is able to translate audio in any language into text. In such an embodiment, the audio may be always be translated into text of the same language. Alternatively, the audio may be always translated into text of a normalized language (e.g., English). This may be a design choice available to each third-party developer.

In the case that the audio data is captured before or after capture of content item 302 (e.g., as voice notes received via microphone from a creator or possessor of content item 302), the output text may reflect notes, comments, narratives, descriptions, and the like, regarding the content of content item 302. This type of audio data may be captured via one or more user interfaces provided by third-party application 250 and/or metadata-injection module 300. Such user interfaces may prompt a user to generate audio metadata by speaking into a microphone (e.g., of user system 130). Alternatively or additionally, the user may be prompted to generate audio metadata by speaking into the microphone even during capture of content item 302.

Audio-to-text module 310 may return the text output from its audio-to-text process to metadata-injection module 300. In an embodiment, metadata-injection module 300 parses the text output received from audio-to-text module 310 to extract or otherwise derive appropriate metadata for content item 302. For example, audio-to-text module 310 may extract one or more character strings from the received text output based on one or more criteria. These criteria may include, without limitation, proper names (e.g., names of people or places), frequently appearing words (e.g., a certain number of significant words that appear the most frequently), peculiar words (e.g., relatively uncommon words), words that are relevant to particular metatags for a standard file format (e.g., words, matching, preceding, and/or following the name of a predefined metatag), etc. Alternatively, metadata-injection module 300 may use the entire text output as metadata.

In an embodiment, metadata-injection module 300 may parse the text output to identify a command that causes certain metadata (e.g., previously-generated metadata or obtainable metadata), indicated by the command, to be associated with content item 302. For example, if metadata-injection module 300 identifies the command "GPS," metadata-injection module 300 may retrieve GPS coordinates from location module 335 and associate the GPS coordinates or geolocation information based on the GPS coordinates with content item 302. As another example, if metadata-injection module 300 identifies the command "recognize faces," metadata-injection module 300 may activate object-recognition module 320 to automatically detect and identify metadata for faces that appear in content item 302, and associate the identified metadata (e.g., first and last name) with content item 302. In a similar manner, such voice commands may be provided for each of the metadata sources and modules described herein (e.g., "author" for authorship module 315, "user interface" for user interface 325, "time" for time module 330, "location" or "GPS" for location module 335, "weather" for weather module 345, "news" for news module 350, identifiers of various sensor(s) for sensor(s) 355, "closed captions" for closed-captions module 360, "AIDC" for AIDC module 365, "contacts" for contacts module 370, "asset" for asset module 375, etc), and when detected may cause metadata-injection module to retrieve metadata from the corresponding metadata source.

1.2.3.2. Authorship Module

In an embodiment, metadata-injection module 300 retrieves authorship information from an authorship module 315. Authorship information may include, without limitation, the first name and/or last name of an author, a username or other identifier of the author, contact information for an author (e.g., phone number, email address, mailing address, etc.), an image of the author (e.g., photograph, avatar, etc.), a title of the author, and/or any other information related to the author of content item 302 (e.g., from employee records, patient records, etc.).

Authorship module 315 may acquire the authorship information (e.g., an author's first name and/or last name and/or other identifier(s) of the author) from autobiographical information in a user's account or profile. The autobiographical information from a user's account may be accessible to authorship module 315 via one or more APIs for an account module that executes on the user device (e.g., user system 130) on which third-party application 250 is executing. The account module may be accessible to authorship module 315 once a user registers or "logs in" to the user device or third-party application 250. For example, when a user authenticates with the user device or third-party application 250—for example, using a username and password, or biometrics (e.g., fingerprint(s) recognition, facial recognition, iris recognition, voice recognition, etc.)—authorship module 315 may be provided with access to account information associated with the authenticated user (e.g., associated with the username, biometrics, etc.). In an embodiment which utilizes biometrics, the biometrics may be obtained from a biometric sensor (e.g., camera, dedicated fingerprint scanner, dedicated iris scanner, microphone, etc.) that is integral to or interfaced with the user device. It should be understood that a user device may have accounts for a plurality of users, and thus, authorship module 315 may return different authorship information depending on which user is logged in at the time that each content item 302 is received or generated. As long as a user's authenticated session is active, authorship module 315 may acquire information from the user's account as needed to be used for metadata. Alternatively, authentication may not be required to obtain authorship information (e.g., depending on a user setting). For example, the authorship information of a user account may be freely accessible to authorship module 315 with or without a prior authentication.

In an embodiment, biometrics may be obtained contemporaneously with content item 302. For example, biometrics may be obtained by a user pressing his finger to a fingerprint scanner during acquisition of content item 302 or contemporaneously with acquisition of content item 302 (e.g., within a predefined time of acquisition of content item 302, via user interfaces preceding or following an acquisition user interface in a wizard provided by third-party application 250, etc.). Third-party application 250, metadata-injection module 300, authorship module 315, or another module may infer from this action that the user intends to inject authorship information into content item 302. Thus, authorship module 315 may receive the biometrics, retrieve authorship information associated with the biometrics, and provide the authorship information to metadata-injection module 300 for injection into content item 302.

As an example, a user could initially register his or her authorship information with third-party application 250, metadata-injection module 300, authorship module 315, user system 130, etc. in a user account or profile associated with that application, module, or system. For embodiments which utilize authentication and/or biometrics, this authorship information or user account may be associated with authentication credentials and/or biometrics, respectively. As part of the registration process, a user may be provided with one or more user interfaces for specifying one or more fields to be used as authorship information. Subsequently, this authorship information may be accessed by authorship module 315 to generate metadata (e.g., in response to a request or procedure call from metadata-injection module 300) for content items (e.g., generated by third-party application 250). In an embodiment, the generation of metadata may be performed by authorship module 315 by extracting the metadata from the authorship information or from using the authorship information as the metadata.

1.2.3.3. Object Recognition Module

In an embodiment, metadata-injection module 300 retrieves object information from an object-recognition module 320. As an example, a user may specify one or more objects in content item 302, for example, by drawing a polygon around each object (e.g., using a touch operation or input device). Alternatively or additionally, metadata-injection module 300 may send or pass content item 302 to object-recognition module 320 which may automatically detect one or more objects in content item 302 (e.g., using well-known methods of edge detection), or metadata-injection module 300 may detect the object(s) in content item 302 and send or pass those objects (e.g., cropped images or audio segments from content item 302 representing the objects) to object-recognition module 320 for identification.

In any case, object-recognition module identifies one or more objects in content item 302. These objects may represent faces, people, animals (e.g., pets), landmarks (e.g., buildings, monuments, geographical features), products (e.g., consumer products), assets (e.g., inventory or infrastructure components), or any other type of recognizable object. In a content item 302 that comprises an image (e.g., photograph) or image frames (e.g., video), objects may be represented by portions of the image containing visual depictions of the object. Additionally, in a content item 302 that comprises audio, objects may be represented by an audio segment containing a sound generated by the object or otherwise related to the object. For example, an object that is a vehicle could be represented by a visual depiction of the vehicle in content item 302 and/or an audio segment representing the sound of a car horn or engine in content item 302.

Object-recognition module 320 may comprise or be interfaced with a reference database 392, which is utilized to identify the object(s) in content item 302. Reference database 392 comprises a plurality of representations of reference objects. Each representation of a reference object may model the reference object. As an example, each representation in reference database 392 may comprise a vector of feature descriptors, each of which quantify a particular feature of the reference object. In an embodiment, object-recognition module 320 converts each detected object from content item 302 into a representation that is similar or identical in structure to the representations stored in reference database 392. For example, if each representation in reference database 392 comprises a vector of feature descriptors, object-recognition module 320 may convert each detected object from content item 302 into a vector of the same feature descriptors (i.e., quantifying the same features of the detected object as for each reference object).

Object-recognition module 320 compares the representation (e.g., feature vector) of each detected object from content item 302 to one or more representations (e.g., feature vectors) of reference objects in reference database 392, and attempts to select a reference object based on one or more criteria. For example, in the case that feature vectors are used to model the detected and reference objects, each comparison may comprise calculating a distance between the feature vector of a detected object and one or more reference objects. Object-recognition module 320 may select at least one of the reference objects based on these distances and/or one or more other criteria (e.g., a threshold). For example, object-recognition module 320 may select the reference object with the shortest distance, one or more reference objects with a distance below a predefined threshold, or the reference object with the shortest distance below a predefined threshold. However, it should be understood that such techniques are a subset of more general pattern-matching techniques, and that object-recognition module 320 may implement other techniques which parameterize or quantify features of objects and/or relationships between features of objects. Regardless of the particular criteria used to select a reference object, the selected reference object represents an identification of the detected object from content item 302. On the other hand, if no reference object meets the criteria, then the detected object from content item 302 may remain unidentified.

In an embodiment, a location (e.g., from location module 335) may be used to restrict comparison to portion(s) of reference database 392. For example, metadata-injection module 300 may receive a location (e.g., GPS coordinates) from location module 335, and send or pass this location to object-recognition module 320. Reference database 392 may comprise similar or identical location information (e.g., GPS coordinates) for one or more of the stored reference objects. Thus, object-recognition module 320, when comparing a detected object from content item 302 to a reference object in reference database 392, may compare the location received from metadata-injection module to the location stored for the reference object. It should be understood that the received location may match the location stored for the reference object if the locations are identical and/or if the locations are within a predefined distance or radius from each other. Alternatively, reference database 392 may be indexed and/or sorted according to location, and object-recognition module 320 may restrict comparisons to only a portion of reference database 392 with matching locations (e.g., identical or within a predefined distance or radius). For example, if a user captures a photograph of Big Ben using his or her smartphone, the GPS coordinates of the smartphone at the time of capture may be obtained by metadata-injection module 300 from location module 335 and passed to object-recognition module 320 to restrict searching to a subset of reference objects within the vicinity (e.g., a predefined radius) of the GPS coordinates, such that Big Ben may be recognized in the photograph more quickly and efficiently than if the entire reference database 392 had to be searched.

Searching of reference database 392 may be restricted in other manners as well. For example, metadata-injection module 300 may receive one or more locations (e.g., GPS coordinate(s) or address(es)) of a user's contacts from contacts application 370, and compare these to a current location of the user's device (e.g., GPS coordinates or an address received from location module 335) to generate a list of locations or contacts within a vicinity (e.g., predefined radius) of the current location of the user's device. Metadata-injection module 300 may send or pass a list of locations within the vicinity of the current location of the user's device to object-recognition module 320. Object-recognition module 320 may receive this list of locations and restrict object recognition to comparisons of detected objects from content item 302 to only those references objects in reference database 392 which are within a vicinity (e.g., predefined radius) of at least one location in the received list of locations. Alternatively or additionally, metadata-injection module 300 may send or pass a list of contacts within the vicinity of the current location of the user's device to object-recognition module 320. Object-recognition module 320 may receive this list of contacts and restrict facial recognition to comparisons of detected faces from content item 302 to only those reference objects in reference database 392 which are associated with a contact in the received list of contacts (e.g., which represent faces of contacts in the list of contacts).

It should be understood that facial recognition is a subset of the above-described object recognition, and can be performed in the same or similar manner as other types of objects. For instance, the representation of a facial object may comprise a vector of features representing facial characteristics, such as the vertical width of the forehead, vertical length of the nose, horizontal width of the lips, vertical distance between the lips and mouth, quantified relationships between different portions of the face (e.g., center of the eyes, eyebrows, ears, nose, etc.), and/or the like.

In addition, it should be understood that audio recognition is also a subset of the above-described object recognition. For example, audio segments may be parameterized or quantified (e.g., into a feature vector) in the same manner as object images, and compared to representations of reference audio objects, in a similar or identical manner, to identify a reference audio object that matches a detected audio segment from content item 302. In this case, the audio segment may represent a person's voice, in which case the comparison between the detected audio segment from content item 302 and reference audio objects in reference database 392 may utilize conventional voice-recognition techniques. Alternatively, the detected audio segment may represent a specific sound (e.g., a bark, car horn, bell, traffic noise, song, Big Ben's chimes, mullah calls to prayer, etc.) that is identical to one of the reference audio objects in reference database 392, in which case object-recognition module 320 may utilize conventional sound-matching techniques.

When object-recognition module 320 matches a detected object from content item 302 to a reference object in reference database 392, object-recognition module 320 may retrieve object information associated with that matching reference object. This object information may also be stored in reference database 392 (e.g., with or associated with the representation of that reference object), or another database (e.g., with records linked to object models stored in reference database 392). The retrieved object information may be returned to metadata-injection module 300, which may use the object information as metadata or to generate metadata, and inject the metadata into content item 302. It should be understood that object information may be returned for each detected and matched object in content item 302. As non-limiting examples, visual identification (i.e., a successful match) of a face in content item 302 may result in the name of a person (i.e., associated with the reference object representing that face in reference database 392) being returned to metadata-injection module 300, visual identification of a pet dog may result in the name of the pet dog being returned, an audio identification of Big Ben's chimes may result in "Big Ben" being returned, a visual identification of Big Ben may also result in "Big Ben" being returned, etc. More generally, the object information may comprise any information related to the object and may potentially include links (e.g., a URL) to additional information, but will typically comprise an identification and/or description of the object.

In an embodiment, when an object is identified (i.e., matched) in content item 302, metadata-injection module 300, object-recognition module 320, user interface 325, or third-party application 250 may prompt the user to confirm that the object was properly identified. For example, if an object in a content item (e.g., photograph) captured by a user is recognized as "Mt. Rushmore," the module may provide the user with a user interface comprising at least the portion of the content item recognized as Mt. Rushmore, a prompt of "Is this Mt. Rushmore?" (or similar prompt), and one or more inputs for either confirming that the object is Mt. Rushmore or indicating that the object is not Mt. Rushmore. If the user confirms that the object was properly recognized, the module may then generate appropriate metadata (e.g., the name of the object) to be associated with content item 302.

In an embodiment, reference database 392 may be created, at least in part, from previously-created content items that are either supplied by an operator of metadata platform 200, a third party (e.g., an operator of third-party platform 240), and/or a user of third-party application 250. For instance, a user may manually tag or otherwise indicate an object in a previously-captured content item (e.g., photograph or video), and associate the object with object information, such as an identifier or description of the object. As an example, a user may utilize a user interface (e.g., provided by third-party application 250) to draw a rectangle around an object (e.g., a face of a subject) in the previously-captured content item, and associate the tagged face with a name of the subject and/or other information. Object-recognition module 320 or another module may then generate a representation of the object (e.g., a graph, feature vector, or other model representing the features and relationships between features of the object), and store the "learned" representation of the object as a reference object in reference database 392 in association with specified object information (e.g., a name of the person if the object is a face). As mentioned above, at least some of these objects (e.g., landmarks, people, pets, etc.) may also be associated with location information (e.g., GPS coordinates, address, city, state, etc.). For example, a reference object representing Big Ben could be associated with GPS coordinates for Big Ben or with "London, England." This location information may facilitate searching when location information is available (e.g., from location module 335). Conversely, this location information may be used to generate location-based metadata when a reference object is matched to a detected object from content item 302 (e.g., to add "London, England" to metadata if Big Ben is matched). For example, object recognition module 320 may return this location information to metadata-injection module 300 in the object information. If this location information comprises GPS coordinates or other raw data, metadata-injection module 300 may send or pass the location information to location module 335 or another module to be converted into more user-friendly metadata (e.g., converting GPS coordinates of Big Ben into "London, England").

Reference database 392 may be a local database (e.g., stored on user system 130) or remote database (e.g., stored on metadata server 110 or elsewhere over network(s) 120). Since the amount of information to be stored for a simple facial-recognition database of known subjects is relatively small, such a database could be stored locally. On the other hand, if reference database 392 included information for a large number of subjects (e.g., larger than the user's universe of known subjects) or also included information for numerous other objects (e.g., landmarks, products, etc.) reference database 302 would likely need to be stored remotely (e.g., on or interfaced with metadata server 110) and accessed (e.g., queried) over a network (e.g., network(s) 120). However, in this case, it should be understood that portions of the remote database corresponding to a certain geographical location of the user device (e.g., landmarks within a predefined radius of a current location of user system 130) may be downloaded to a user device as a temporary local database for quicker access. The structure of reference database 392 can be in the form of a lookup table (e.g., a relational database), or any other suitable format.

1.2.3.4. User Interface

In an embodiment, metadata-injection module 300 retrieves manually-input information from a user interface 325. Third-party application 250 or metadata-injection module 300 may provide one or more user interface(s) 325 which receive user input 393. For example, user interface 325 may comprise input fields for entering metadata or information from which metadata may be derived. In an embodiment, user interface 325 may comprise input fields dedicated to receiving metadata from the user. In this case, the information input into the input fields is provided as metadata to metadata-injection module 300 for injection into content item 302. Otherwise, metadata-injection module 300 may utilize the information to derive metadata to be injected into content item 302.

In an embodiment, user interface 325 may receive audio input from a user, in addition to or instead of text input. For example, user system 130 may comprise an integrated or otherwise connected microphone, and the user may interact with user interface 325 to record audio by, for example, selecting an input which initiates recording of audio through the microphone. In this case, user interface 325 may return the audio data to metadata-injection module 300, which may send or pass the audio data to audio-to-text module 310 to be converted into text. Metadata-injection module 300 may then generate metadata, from the text received from audio-to-text module 310, and inject the metadata into content item 302.

1.2.3.5. Time Module

In an embodiment, metadata-injection module 300 retrieves temporal information from a time module 330. In an embodiment, time module may comprise or communicate with a system clock of the user device, and may return time information (e.g., a timestamp), representing the current time, to metadata-injection module 300.

1.2.3.6. Location Module

In an embodiment, metadata-injection module 300 retrieves location information from a location module 335. Location module 335 may comprise a GPS receiver. The GPS receiver may be integral to the device (e.g., smartphone) on which metadata-injection module 300 is executing, and may derive current GPS coordinates (e.g., latitude, longitude, and elevation) representing the current location of the device. Location module 335 may utilize the GPS coordinates or received GPS coordinates (e.g., GPS coordinates received from metadata-injection module 300 that are associated with a previously-generated content item), to determine higher-level geolocation information, such as an address (e.g., street, city, state, and/or Zip code), to be returned to metadata-injection module 300 for use as or in metadata. For example, location module 335 may query a local or remote database using the GPS coordinates to retrieve an address associated with the GPS coordinates.

The location information received from location module 335 may comprise a location (e.g., GPS coordinates, address, etc.) of the device at the time that content item 302 was captured (if the content item was captured by the device) and/or a geolocation represented in content item 302 (which may be the same as the current geolocation of the device if the device recently captured the content item, or which may be different than the geolocation of the device if the content item was captured by a different device and transferred to the current device or was captured by the current device at an earlier time). In addition, the location information may comprise a visual representation of a location, such as the location plotted on a map image. Thus, in this case, the metadata injected by metadata-injection module 300 may be a map image with the plotted location, and location module 335 may comprise or be interfaced with a map service, from which it retrieves the map images.

As an example, as a user utilizes his or her smartphone to capture photographs while in Washington, D.C., metadata-injection module 300 may receive each photograph as a content item 302, acquire the current geolocation of the smartphone from location module 335, and associate the acquired geolocation with each photograph. The geolocation may comprise GPS coordinates, or metadata-injection module 300 or location module 335 may convert the GPS coordinates into higher-level information, such as an address, city, state, etc. For example, location module 3335 may acquire GPS coordinates from a GPS receiver, and determine that the GPS coordinates correspond to Washington, D.C. (e.g., by determining that the GPS coordinates are within the municipal boundaries of Washington, D.C.). Consequently, related metadata (e.g., the keywords "washington, d.c.," "washington," "district of columbia," etc.) may be associated with each of the photographs as it is captured.

In an embodiment, the location information received by metadata-injection module 300 from location module 335 may comprise more than a representation of a geolocation of the user device. For instance, the location information may comprise information that is related to or associated with a particular location. For example, location module 335, metadata-injection module 300, third-party application 250, and/or another application may provide one or more user interfaces via which a user may associate descriptive information (e.g., text, dedicated metadata, etc.) with a particular location (e.g., represented by GPS coordinates, address, etc.). Alternatively or additionally, descriptive information may be received in another manner (e.g., retrieved from an external system 150). In either case, the descriptive information may be stored in association with the corresponding location information. In this manner, pairs of descriptions and location information may be stored in a locations database that is accessible to location module 335. The locations database may be hosted locally (e.g., on user system 130) or remotely (e.g., on metadata server 110 or an external system 150). If the locations database is hosted remotely, it may be accessed by location module 335 over one or more networks (e.g., network(s) 120) via standard communication protocols.

As an example, a user may associate location information for his or her parents' white Victorian home with a description including "parents," "family," "Victorian," "white," etc. The description may be stored in association with the location information for the user's parents' home (e.g., GPS coordinates, address, etc.) in a locations database. The locations database may be indexed by the location information for retrieval based on location information. Thus, location module 335 may perform a lookup in locations database, based on location information received from metadata-injection module 300, to retrieve descriptive information associated with the received location information.

In an embodiment, metadata-injection module 300 may send or pass location information for content item 302 to location module 335. Alternatively, location module 335 may acquire a current location of the user device (e.g., from a GPS receiver) to be used as the location information for content item 302 (e.g., if content item 302 is captured contemporaneously by the user device). In either case, location module 335 may compare the location information for content item 302 to location information stored in the database that is accessible to location module 335 to identify any matches. The location information for content item 302 may match location information stored in the database if one is within a vicinity (e.g., predefined radius) of the other, geographically contained within the other (e.g., location information consisting of "San Diego" would match location information consisting of "California" since San Diego is within California), and/or the like. If a match occurs, location module 335 may retrieve the description associated with the matched location information from the database, and return at least a portion of the retrieved description as the location information to metadata-injection module 300 to be used for metadata. It should be understood that multiple locations stored in the database may match the location information associated with content item 302, in which case location module 335 may return multiple descriptions, all of which may be used by metadata-injection module 300 to generate metadata for injection into content item 302.

1.2.3.7. Scheduling Module

In an embodiment, metadata-injection module 300 retrieves scheduling information from a scheduling module or application 340. Scheduling module 340 may be a module comprised in third-party application 250. Alternatively, scheduling module 340 may be an application or comprised in an application that is separate from third-party application 250 (e.g., a separate application executing locally on user system 130, or a separate application executing remotely over network(s) 120 on a server or other system, such as metadata server 110, external system 150, or third-party platform 240), and metadata-injection module 300 may communicate with scheduling application 340 via one or more APIs. For example, scheduling module 340 may be or interface with a calendar or appointment application (e.g., Google Calendar™ Microsoft Outlook™, etc.) that a user utilizes to temporally organize events in his or her life, a dispatch system which schedules dispatch activities (e.g., for asset management, installations, repairs, inspections, emergency or non-emergency police, fire, or medical services, etc.), etc.

The scheduling information may comprise or be derived from event information with one or more event details and one or more parameters defining a time or time period. The event detail(s) may comprise a title, location, description, and/or the like. The parameter(s) may comprise a start time (e.g., start timestamp), end time (e.g., end timestamp), or both a start time and end time (e.g., start timestamp and end timestamp). However, it should be understood that these are merely examples, and that the event detail(s) and/or parameter(s) may take any form suitable to convey information associated with a time period. In the case that the scheduling information has been derived from the event information, the scheduling information may comprise metadata to be added to content item 302, instead of or in addition to the particular event detail(s) or parameter(s).

In an embodiment, metadata-injection module 300 interfaces with scheduling application 340 to generate scheduled metadata. Scheduled metadata refers to metadata that is to be added to content items generated or received within a particular time period. Scheduling information for a particular time period may be input into scheduling application 340. For example, this scheduling information may comprise event information for an event that a user or system expects to occur at a specified time or within a specified time range (e.g., lunch, appointment, meeting, party, vacation, inspection or maintenance of an asset, etc.). More generally, the scheduling information may comprise a set of metadata that is to be injected into content items generated or received at a specified time or within a specified time range. A time range may include a start time (e.g., any time after 12:00 pm), an end time (e.g., any time before 1:00 pm), or a start and end time (e.g., 12:00 pm to 1:00 pm). The start and/or end times may be represented as timestamps in Unix or Portable Operating System Interface (POSIX) time, which represents time as the number of elapsed seconds since Jan. 1, 1970, or similar formats in which the timestamp conveys at least a specific year, month, day, hour, minute, and second. It should also be understood that a time range may be represented in other forms, such as a day (e.g., July 4, which may also be represented using a starting timestamp representing 12:00 am on July 4th and an end timestamp representing 11:59 pm on July 4th), month (e.g., January, which may also be represented as a starting timestamp representing 12:00 am on January 1st and an end time stamp representing 11:59 pm on January 31st), and the like.

After metadata-injection module 300 receives a content item 302, metadata-injection module 300 may access a timestamp representing the time of creation of content item 302, and request or otherwise retrieve scheduling information from scheduling module 340 based on this timestamp. Alternatively, metadata-injection module 300 may access a timestamp representing the time that content item 302 was received by metadata-injection module 302. As still another alternative, along with content item 302, metadata-injection module 300 may receive a timestamp as a parameter representing the time that should be used, or a parameter which specifies whether to use the timestamp representing the creation of content item 302, the timestamp representing when content item 302 was received by metadata-injection module 302, or another timestamp.

In any case, metadata-injection module 300 may send or pass a timestamp to scheduling module 340, and scheduling module 340 may receive the timestamp and return scheduling information to metadata-injection module based on that timestamp. Specifically, scheduling module 340 may return any scheduling information that comprises a time period that encompasses the time represented by the timestamp received from metadata-injection module 300. It should be understood that the scheduling information may comprise event information for multiple scheduled events, including nested events. As an example, scheduling module 340 may store the following four events (e.g., input by a user into a calendar application): (1) Conference in San Diego all day on July 4th, (2) Meeting with John Smith from 10:00 am to 4:00 pm on July 4th, (3) Lunch at ABC Restaurant from 12:00 pm to 1:00 pm on July 4th, and (4) Dinner with Jane Doe from 5:00 pm to 7:00 pm on July 4th. If the received timestamp associated with content item 302 represents 12:30 pm on July 4th, scheduling module 340 may return metadata for events (1)-(3), but not (4), in response to the request. Specifically, scheduling module 340 may return, "Conference in San Diego," "Meeting with John Smith," "Lunch at ABC Restaurant," since all of these events are associated with time periods that encompass the received timestamp, whereas "Dinner with Jane Doe" is associated with a time period that does not encompass the received timestamp. Notably, event (3) is nested within event (2), which is nested within event (1). After metadata-injection module 300 receives the scheduling information returned by scheduling module 340, metadata-injection module 300 may generate metadata from the scheduling information. For instance, metadata-injection module 300 may associate the scheduling information, as is, with content item 302, or may otherwise derived metadata from the scheduling information (e.g., by extracting the terms "San Diego," "John Smith," and "ABC Restaurant" from the scheduling information).

Alternatively, scheduling module 340 may generate the metadata and return the metadata to metadata-injection module 300 to be used as the metadata injected into content item 302.

In an alternative embodiment, metadata-injection module 300 may generate metadata in advance of receiving content item 302. For example, metadata-injection module 300 may periodically poll scheduling module 340 to retrieve scheduling information related to a current or future time period (e.g., poll scheduling module 340 at the beginning of every fifteen-minute period to retrieve scheduling information for that fifteen-minute period), scheduling module 340 may periodically send or pass scheduling information to metadata-injection module (e.g., pass scheduling information to metadata-injection module 300 at the beginning of every fifteen-minute period for that fifteen-minute period), scheduling module 340 may send or pass scheduling information to metadata-injection module 300 at the start of any time period for which corresponding event information is stored, or scheduling module 340 may send or pass scheduling information to metadata-injection module 300 contemporaneously with whenever the corresponding event information is received (e.g., pass the scheduling information to metadata-injection module 300 as soon as corresponding event information is received at scheduling module 340 or whenever it is modified at scheduling module 340). In these embodiments, after metadata-injection module 300 receives the scheduling information, metadata-injection module 300 may generate the metadata in a similar manner as described above either before or after a relevant content item 302 is received. When metadata-injection module 300 receives a content item 302, metadata-injection module 300 may compare the relevant timestamp (e.g., timestamp received with content item 302, representing the time of creation of content item 302, or representing the time of receipt of content item 302) to the time period in the scheduling information (or associated with previously-generated metadata for the scheduling information), and if time period(s) in the scheduling information encompass the timestamp, either generate the metadata or retrieve previously-generated metadata for the matching scheduling information and associate the metadata with content item 302.

In an embodiment, scheduling module 340, third-party application 250, or another application may provide one or more user interfaces that enable a user to associate scheduling information with a particular time period (e.g., represented by a start timestamp and end timestamp). As discussed above, these user interfaces may be part of a calendar or appointment application that a user utilizes to temporally organize and keep track of events in his or her life. Alternatively, these user interfaces may be specifically provided for scheduling metadata, in which case the scheduling information may comprise data (e.g., text) that the user has specifically indicated should be used as the metadata. In either case, the user interface(s) may comprise inputs which allow the user to specify a state date and time, an end date and time, and/or a description or metadata to be associated with the time period represented by the start date and/or time and/or end date and/or time. The user interface(s) may also comprise input(s) for specifying whether or not the event represented by the description and time period is a one-time event (e.g., occurring for only a single time period) or recurring event (e.g., occurring for the same time period over the course of multiple days). The input(s) for entering a description or metadata may comprise one or more fields, such as names of individuals, comments, title, location, etc.

In an embodiment, scheduling module 340 may be used to schedule metadata from other metadata sources 220 (e.g., 310-335 and 345-390). For example, as mentioned above, one or more user interfaces may be provided by scheduling module 340, third-party application 250 or another application, specifically for scheduling metadata. These user interface(s) may enable a user to specify the metadata sources that should be retrieved for content items created during a defined time period. Thus, instead of or in addition to event details, the defined time period may be associated with an identification of one or more metadata sources to be used by metadata-injection module 300. Consequently, when metadata-injection module 300 receives a content item generated during the defined time period, it may only consult the metadata sources associated with that time period in scheduling module 340.

As an example, a user may utilize a user interface to create the following scheduled metadata sources: (1) for all day on Jul. 1, 2016, authorship module 315 and asset module 375, (2) from 9:00 am to 4:00 pm on Jul. 1, 2016, location module 335 and weather module 345, (3) from 12:00 pm to 1:00 pm on Jul. 1, 2016, object-recognition module 320, and (4) from 6:00 pm on Jul. 1, 2016 to 8:00 am on Jul. 3, 2016, contacts module 370. In this example, if metadata-injection module 300 receives a content item 302 generated at 12:30 pm on Jul. 1, 2016, metadata-injection module 300 will only retrieve metadata from the metadata sources specified in (1), (2), and (3), but not (4). Notably, when the scheduling information is nested (e.g., (3) is nested entirely within (2), which is nested entirely within (1), and (4) is nested partially within (1)), metadata-injection module 300 may utilize all of the metadata sources in the nested scheduling information as well as the overarching scheduling information. Thus, for the content item 302 generated at 12:30 pm on Jul. 1, 2016, metadata-injection module 300 may only retrieve metadata from authorship module 315, asset module 375, location module 335, weather module 345, and object-recognition module 320. On the other hand, if a content item 302 were generated at 11:30 pm on Jul. 1, 2016, metadata-injection module 300 may only retrieve metadata from authorship module 315, asset module 375, and contacts module 370. However, it should be understood that in this embodiment there may be some modules (e.g., authorship module 315) from which metadata-injection module 300 always retrieves metadata, regardless of whether or not that module is identified in scheduling information.

1.2.3.8. Weather Module

In an embodiment, metadata-injection module 300 retrieves weather information from a weather module 345. Weather module 345 may be a module comprised in third-party application 250. Alternatively, weather module 345 may be an application or service (e.g., web service) or comprised in an application or service that is separate from third-party application 250 (e.g., a separate application or service executing locally on user system 130, or a separate application executing remotely over network(s) 120 on a server or other system), and metadata-injection module 300 may communicate with weather application or service 345 via one or more APIs. For example, weather module 345 may be a web service, such as the (National Oceanic and Atmospheric Administration (NOAA) National Weather Service (NWS).

Weather information may comprise any weather-related information, including, without limitation, temperature, humidity, a general description (e.g., sunny, partly cloudy, cloudy, rainy, thunderstorms, lightning, etc.), wind speed, atmospheric pressure, precipitation, forecasts (e.g., chance of precipitation), weather alerts, etc.

In an embodiment, weather module 345 may receive location information (e.g., city and state, Zip code, address, GPS coordinates, etc.) and/or time information (e.g., a timestamp representing a current, past, or future time) as an input. For example, metadata-injection module 300 may send or pass the location information and/or time information to weather module 345 as parameter(s). In the case that location information is received, weather module 345 may return weather information relevant to the location represented by the location information (e.g., the temperature and humidity at that location). In the case that time information is received, weather module 345 may return weather information relevant to the time represented by the time information (e.g., the temperature and humidity at that time). In the case that location information and time information are received, weather module 345 may return weather information relevant to the location and time represented by this information (e.g., the temperature and humidity at that location at that time). If the time is a current time, then the weather information will reflect the current weather, whereas if the time is a past time, then the weather information will reflect historical weather, and, if the time is a future time, then the weather information may reflect a weather forecast.

Weather module 345 may return the weather information for the location and/or time to metadata-injection module 300, which may use the weather information to generate metadata (e.g., temperature, humidity, general description, etc.) to be injected into content item 302. In this manner, weather-related metadata may be added to a content item 302 contemporaneously with creation of the content item 302. As an example, if content item 302 is captured during a sunny day, as indicated in weather information received from weather module 345, metadata-injection module 300 may inject "sunny" in content item 302. In the case that content item 302 was previously captured, metadata-injection module 300 may send or pass time information (e.g., a timestamp) reflecting the time of capture to weather module 345 in order to retrieve historic weather information. In this manner, even old content items can be injected with metadata reflecting the weather at the time of their capture.

1.2.3.9. News Module

In an embodiment, metadata-injection module 300 retrieves news information from a news module 350. News module 350 may be a module comprised in third-party application 250. Alternatively, news module 350 may be an application or service (e.g., web service) or comprised in an application or service that is separate from third-party application 250 (e.g., a separate application or service executing locally on user system 130, or a separate application executing remotely over network(s) 120 on a server or other system), and metadata-injection module 300 may communicate with news application or service 350 via one or more APIs. For example, news module 350 may be a web service, such as one provided by Thomson Reuters™

News information may comprise news articles, journal articles, breaking news, research, opinions, economic forecasts, stock or stock market activity, etc.

In an embodiment, news module 350 may receive location information (e.g., city and state, Zip code, address, GPS coordinates, etc.) and/or time information (e.g., a timestamp representing a current, past, or future time) as an input. For example, metadata-injection module 300 may send or pass the location information and/or time information to news module 350 as parameter(s). In the case that location information is received, news module 350 may return news information relevant to the location represented by the location information (e.g., breaking news relevant to that location). Otherwise, news module 350 may return general news information (e.g., world or national events, stock or stock market activity, etc.). In the case that time information is received, news module 350 may return news information relevant to the time represented by the time information (e.g., significant news at that time). In the case that location information and time information are received, news module 350 may return news information relevant to the location and time represented by this information (e.g., significant news at that location at that time). If the time is a current time, then the news information will reflect current news (e.g., breaking news), whereas if the time is a past time, then the news information will reflect historical news (e.g., significant news articles from that time period), and, if the time is a future time, then the news information may reflect, for example, an economic forecast.

News module 350 may return the news information for the location and/or time to metadata-injection module 300, which may use the news information to generate metadata (e.g., significant news, relevant stock market activity, etc.) to be injected into content item 302. In this manner, news-related metadata may be added to a content item 302 contemporaneously with creation of the content item 302. As an example, if content item 302 is captured during a significant event, metadata-injection module 300 may inject metadata related to this event into content item 302 (e.g., so that the user could see what he or she was doing at the time of that event). In the case that content item 302 was previously captured, metadata-injection module 300 may send or pass time information (e.g., a timestamp) reflecting the time of capture to news module 350 in order to retrieve historic news information. In this manner, even old content items can be injected with metadata reflecting significant events at the time of their capture.

1.2.3.10. Sensors

In an embodiment, metadata-injection module 300 retrieves sensor information from one or more sensors 355. Sensor(s) 355 may provide real-time or historic sensor information to metadata-injection module 300. Sensor(s) 355 may be integral to a user system 130 executing third-party application 250 and/or metadata-injection module 300 and/or communicatively connected to user system 130, either directly or indirectly, via a wired or wireless connection. In the case that there are a plurality of sensors 355, the sensors may be communicatively connected to the device on which third-party application 250 and/or metadata-injection module 300 are executing via the same or different types of connections. For example, one sensor may communicate with metadata-injection module 300 over a Universal Serial Bus (USB), one sensor may communicate with metadata-injection module 300 over a network (e.g., network(s) 120, which may include the Internet), one sensor may communicate with metadata-injection module 300 via a wireless technology standard (e.g., Bluetooth™, cellular technology, satellite technology, etc.), etc.

Metadata-injection module 300 may receive sensor information from sensor(s) 355, and use the sensor information as metadata or derive metadata from the sensor information. In either case, metadata-injection module 300 may inject the metadata into content item 302.

The sensor information may comprise any type of data that is capable of being output from a sensor. Examples include, without limitation, a heartbeat from a heartbeat monitor, an electrocardiographical signal (ECG or EKG)

from electrodes attached to a patient, a blood pressure from a blood pressure monitor, a temperature from a thermometer, a speed from a speedometer or radar, acceleration from an accelerometer, atmospheric pressure from a barometer, lumens from a light sensor, an indication of a proximate object from a proximity sensor, weight from a scale, pitch, roll, and/or yaw from a gyroscope, latitude, longitude, and/or elevation from a GPS sensor, humidity from a hygrometer, motion from a seismometer, voltage from a voltmeter, etc. It should be understood that the outputs of any type of sensor may be used. Possible sensors include, without limitation, a geophone, hydrophone, microphone, fuel sensor, air-fuel ratio meter, blind spot monitor, oxygen sensor, parking sensor, radar gun, speedometer, speed sensor, throttle position sensor, tire-pressure monitoring sensor, torque sensor, transmission fluid temperature sensor, wheel speed sensor, breathalyzer, carbon dioxide sensor, carbon monoxide sensor, holographic sensor, hydrogen sensor, hydrogen sulfide sensor, infrared point sensor, potentiometric sensor, smoke detector, current sensor, magnetometer, metal detector, voltage detector, air flow meter, anemometer, flow sensor, gas meter, water meter, Geiger counter, neutron detector, air speed indicator, altimeter, depth gauge, gyroscope, inertial navigation system, magnetic compass, variometer, auxanometer, free fall sensor, gravimeter, impact sensor, inclinometer, laser rangefinder, odometer, photoelectric sensor, position sensor, rate sensor, shock detector, stretch sensor, tilt sensor, flame detector, infrared sensor, photodetector, barometer, pressure sensor, tactile sensor, hydrometer, level sensor, calorimeter, thermometer, pyrometer, alarm sensor, motion detector, proximity sensor, occupancy sensor, biosensor, sonar, ultrasonic sensor, radio sensor, actigraphic sensor, heartbeat sensor, hyperspectral sensor, etc.

1.2.3.11. Closed Captions

In an embodiment, metadata-injection module 300 retrieves closed-captions information from a closed-captions module 360. In some cases, content item 302 may include closed captions, which may have been generated from audio data in content item 302 and added to content item 302 at a prior time (e.g., prior to the time at which content item 302 was received by metadata-injection module 300, or after audio data from content item 302 has been processed by audio-to-text module 310 into subtitles that are then added to content item 302). Closed captions generally comprise text information that is embedded in or otherwise associated with content item 302, and typically represent at least a significant amount, if not all, of the dialogue and/or sound effects present in the associated content item.

In cases in which content item 302 comprises closed captions, the closed-captions data may be sent from metadata-injection module 300 to closed-captions module 360. The closed-captions data may be extracted from content item 302, and the extracted closed-captions data may be sent to closed-captions module 360. Alternatively, the entire content item 302 may be sent from metadata-injection module 300 to closed-captions module 360, and closed-captions module 360 may extract the closed-captions data from content item 302.

In an embodiment, closed-captions module 360 parses the text of the closed-captions data to extract one or more character strings based on one or more criteria. These criteria may include, without limitation, proper names (e.g., names of people or places), frequently appearing words (e.g., a certain number of significant words that appear the most frequently), peculiar words (e.g., relatively uncommon words), words that are relevant to particular metatags for a standard file format (e.g., words matching, preceding, and/or following the name of a predefined metatag), etc. Alternatively, metadata-injection module 300 may use the entire text of the closed-captions data as metadata.

In any case, the character string(s) may be returned by closed-captions module 360 to metadata-injection module 300 to be injected into content item 302 as metadata or to be used to generate metadata to be injected into content item 302.

1.2.3.12. Automatic Identification and Data Capture (AIDC)

In an embodiment, metadata-injection module 300 retrieves Automatic Identification and Data Capture (AIDC) information from an AIDC module 365. AIDC information refers to the automatic identification of objects and/or the automatic collection of external data about those objects. AIDC technologies include, without limitation, bar codes, Quick Response (QR) codes, Radio Frequency Identification (RFID), biometrics (e.g., facial recognition, iris recognition, fingerprint recognition, etc.), magnetic stripes, Optical Character Recognition (OCR), smart codes, and voice recognition.

In an embodiment, AIDC module 365 may be comprised in, comprise, or work in conjunction with object-recognition module 320. Specifically, object-recognition module 320 may recognize objects (e.g., represented by images or audio segments) in content item 302, and AIDC module 365 may collect information about the recognized objects to be used for metadata by metadata-injection module 300.

As an example, content item 302 may comprise an image of a barcode or QR code. Metadata-injection module 300 may send or pass content item 302 to object-recognition module 320, which identifies the barcode or QR code. Object-recognition module 320 may return the barcode or QR code to metadata-injection module 300 which sends or passes the barcode or QR code to AIDC module 365, or objection-recognition module 320 may send or pass the barcode or QR code directly to AIDC module 365 (in which case, AIDC module 365 may return the AIDC information to object-recognition module 320, which returns the AIDC information to metadata-injection module 300), depending on the particular implementation. Alternatively, metadata-injection module 300 may send or pass content item 302 to AIDC module 365, which may be programmed to identify the barcode or QR code without the aid of object-recognition module 320 (e.g., using identical or similar object-recognition techniques as described with respect to object-recognition module 320).

In either case, AIDC module 365 may decode the barcode or QR code to produce a character string. At least a portion of this character string may represent metadata to be injected into content item 302, in which case, it may be returned to metadata-injection module 300 to be injected into content item 302. Alternatively or additionally, at least a portion of this character string may identify or reference additional metadata to be injected into content item 302. For example, the character string may include a Uniform Resource Identifier (URI) (e.g., a Uniform Resource Locator (URL)). In this case, AIDC module 365 may acquire the resource (e.g., webpage) at the URI and return that resource or metadata derived (e.g., extracted) from that resource to metadata-injection module 300 to be injected into content item 302.

As another example, AIDC module 365 may perform OCR on content item 302 (or receive the results of OCR performed by object-recognition module 320) to convert visual representations of one or more characters in content item 302 into one or more character strings. AIDC module 365 may then return these character string(s) or metadata derived (e.g., extracted) from these character string(s) to metadata-injection module 300 to be injected into content item 302. For example, if content item 302 comprises a photograph of a "stop" sign, AIDC module 365 may recognize the word "stop" and return the word "stop" as metadata to metadata-injection module 300. If content item 302 comprises a photograph of a document, AIDC module 365 may OCR the document and return the document text to metadata-injection module 300.

As another example, AIDC module 365 may be communicatively connected to an RFID reader, which receives information from one or more RFID tags in the proximity of the RFID reader, a magnetic stripe reader which reads information from a magnetic stripe (e.g., of an identification card), and/or a smart card reader which reads information from an integrated circuit in a smart card. In each of these cases, the information may be received by AIDC module 365 and returned to metadata-injection module 300 and/or used to derive (e.g., extract) metadata that is returned to metadata-injection module 300 to be injected into content item 302.

1.2.3.13. Contacts Module

In an embodiment, metadata-injection module 300 retrieves contact information from a contacts module 370. Contacts module 370 may be a module comprised in third-party application 250. Alternatively, contacts module 340 may be an application or comprised in an application that is separate from third-party application 250 (e.g., a separate application executing locally on user system 130, or a separate application executing remotely over network(s) 120 on a server or other system), and metadata-injection module 300 may communicate with contacts application 370 via one or more APIs. For example, contacts module 370 may be an address book application or module (e.g., a contacts list managed by the Andriod™ or iOS™ operating system, Microsoft Outlook™, etc.) that a user utilizes to organize personal and/or professional contacts.

The contact information may comprise or be derived from one or more contact records stored in a contacts database comprising a plurality of contact records. Each contact record may comprise a contact's first name, middle name, last name, suffix, nickname, title, employer, relationship to the user (e.g., spouse, parent, boss, coworker, friend, etc.), phone number(s), email address, mailing address or address of residence, notes regarding the contact, and/or the like. The contact information may comprise the metadata to be inject into content item 302 or information from which metadata-injection module 300 derives the metadata to be injected into content item 302.

Metadata-injection module 300 may send or pass a portion of a contact's information in a query to contacts module 370. This portion of contact information may have been retrieved or derived from information or metadata received from one or more of the other metadata sources 220. For example, metadata-injection module 300 may receive or derive a first and last name from another metadata source, such as audio-to-text module 310 (e.g., if the name was mentioned in audio data in content item 302), object-recognition module 320 (e.g., if object information associated with an identified face comprises the name), user interface 325 (e.g., if the user manually inputs the name), location module 335 (e.g., if the user device is within a predefined radius of a location associated with the name), scheduling module 340 (e.g., if scheduling information for an event occurring during the creation date and time of content item 302 comprises the name), and/or closed-captions module 360 (e.g., if closed captions for content item 302 comprise the name). Metadata-injection module may then send or pass this first and last name to contacts module 370. As another example, metadata-injection module 300 may receive or derive an address from another metadata source, such as location module 335 (e.g., a current location of the user device).

Contacts module 370 may receive the query from metadata-injection module 300, and use the portion of contact information in the query to retrieve one or more contact records from the contacts database. For example, contacts module 370 may search the contact records in the contacts database to identify one or more contact records comprising the portion of contact information. Using the example above, if the query comprises a first name and last name (e.g., obtained from another metadata source), contacts module 370 may search the plurality of contact records to identify at least one contact record containing both the first name (e.g., in a first name field of the contact record) and the last name (e.g., in a last name field of the contact record). Using the other example above, if the query comprises a location (e.g., a current location of the device received from location module 335), contacts module 370 may search the plurality of contact records to identify at least one contact record containing the address.

If a contact record matching the portion of contact information is identified from the contacts database, contacts module 370 may return the full contact record or at least a portion of the contact record (e.g., the portion representing metadata to be injected into content item 302) to metadata-injection module 300. Using the example above, if a contact record is identified having the first name and last name from the portion of contact information in the query received from metadata-injection module 300, contacts module 370 may return contact information from that contact record, such as a title, an employer, a relationship to the user, one or more telephone numbers and types (e.g., work, home, mobile, etc.), an email address, mailing address or address of residence, notes regarding the contact, etc. It should be understood that, if no contact record matching the portion of contact information is identified, contacts module 370 may return nothing or may return an indication that no contact record was identified.

In an embodiment, the contacts database may comprise records other than representing friends, family, coworkers, etc. For example, the contacts database may comprise patient records, employee records, etc. In such a case, contacts module 370 may more appropriately be referred to as a patients module, employees module, etc., respectively. However, it should be understood that contacts module 370 may operate in the same manner regardless of the type of personal relationships that the database records actually represent.

1.2.3.14. Asset Module

In an embodiment, metadata-injection module 300 retrieves asset information from an asset module 375. Metadata-injection module 300 may receive an identification of an asset from one or more of the other metadata sources 220. This asset identifier may comprise, for example, an employee identifier, a patient identifier, an identifier of an infrastructure component (e.g., a wind turbine, motor, transmission line, vehicle, machine, tool, pipe, valve, sensor, etc.), an identifier of an inventory item (e.g., consumer product), etc. The identifier may comprise a character string (e.g., a string of numbers, an alphanumeric character string, etc), and may be unique (e.g., representing a single instance of a particular asset) or non-unique (e.g., representing a type, class, or category of asset). As an example, metadata-injection module 300 may receive the asset identifier from AIDC module 365. AIDC module 365 may have decoded or received the asset identifier from a barcode, QR code, OCR, RFID tag, magnetic stripe, smart card, etc., as described elsewhere herein. Metadata-injection module 300 may determine that the metadata received from AIDC module 365 comprises an asset identifier and send or pass the asset identifier to asset module 375. Alternatively, metadata-injection module 300 could pass all metadata received from particular metadata source(s) (e.g., AIDC module 365, a dedicated asset identifier field in user interface 325, etc.) or all metadata sources to asset module 375, and asset module 375 could return any asset information associated with portions of that metadata (e.g., by performing queries for all portions of the metadata against one or more asset databases in a brute force search method) to metadata-injection module 300.

In an embodiment, asset module 375 receives the asset identifier from metadata-injection module 300 and may query one or more asset databases based on the received asset identifier. The asset database(s) may be local (e.g., on the same device) or remote (e.g., across network(s) 120) from asset module 375. In either case, asset module 375 may generate a request or query comprising the asset identifier to perform a lookup on the database(s). In the case that an asset database is local, asset module 375 may perform a lookup on the asset database using the asset identifier. In the case that an asset database is remote, asset module 375 may send the request over one or more networks (e.g., network(s) 120, which may include the Internet) to a database server, which may perform a lookup on the asset database using the asset identifier and return one or more matches. Any matches may be returned as metadata to metadata-injection module 300, or used to derive (e.g., extract) metadata which is returned to metadata-injection module 300.

The asset information returned by asset module 375 to metadata-injection module 300 may comprise any information associated with an asset identifier, for example, in an asset database. The asset information may differ depending on the type of asset. As an example, asset information associated with an asset identifier for a patient may comprise a medical record for that patient, including name, images (e.g., patient photograph, X-rays, slide images, etc.), insurance information, physician's notes, test results, and/or the like. Asset information associated with an asset identifier for a wind turbine may comprise a location, operating statistics, model number, manufacturer's name, inspection and maintenance reports, etc. Asset information associated with an asset identifier for a vehicle may comprise a make, model, year, color, license plate number, vehicle identification number (VIN), insurance information, driver information, inspection and maintenance reports, etc. Metadata-injection module 300 may derive metadata, to be injected into content item 302, from all or a portion of the received asset information.

1.2.3.15. Digital Rights Management (DRM) Module

In an embodiment, metadata-injection module 300 retrieves digital rights management (DRM) information from a DRM module 380. DRM information may be predefined and stored in DRM module 300, and retrieved by metadata-injection module 300 when a content item 302, matching one or more criteria, is received. For example, the one or more criteria may comprise certain authorship information retrieved from authorship module 315 (e.g., content item 302 was generated by a predefined author), scheduling information retrieved from scheduling module 340 (e.g., content item 302 was generated during a predefined time period), AIDC information retrieved from AIDC module 365 (e.g., content item 302 comprises an AIDC code or was captured contemporaneously with the reading of AIDC information that identifies a DRM scheme), and/or other criteria, including criteria not determined based on information retrieved from a metadata source (e.g., content item 302 is of a predefined type or is received from a predefined source). The DRM information may comprise an identification of a DRM scheme or an implementation of a DRM scheme.

Metadata-injection module 300 may utilize the DRM information retrieved from DRM module to apply a DRM scheme to content item 302. For example, the DRM scheme governing content item 302 may be embedded as metadata into content item 302 to produce a DRM-injected content item 304. In a simple example, the DRM scheme may simply be a copyright notice which is embedded in a metadata field of content item 302 (e.g., in the "Copyright" field for IPTC). However, it should be understood that more advanced DRM may be used.

1.2.3.16. Quick Tag Module

In an embodiment, metadata-injection module 300 retrieves quick-tag information from a quick-tag module 385. Quick-tag module 385 enables a user to quickly add metadata to one or more content items 302. Due to its functional similarities, in certain aspects of an embodiment, to audio-to-text module 310, user interface 325, and scheduling module 340, quick-tag module 385 may comprise audio-to-text module 310, user interface 325, and/or scheduling module 340, be comprised in one of these metadata sources, or be otherwise interfaced with these metadata sources.

In an embodiment, quick-tag module 385 receives an audio input from a user. For example, quick-tag module 385 may interface with a microphone of user system 130 to record audio in response to a user operation. The user operation may comprise a user selection of a soft key (e.g., provided by user interface 325 or a user interface of third-party application 250), for example, by touching the key on a touch panel display or selecting the key using a pointing device (e.g., mouse, trackball, etc.). Alternatively, the user operation may comprise a user pressing a hard key (e.g., provided on a housing of user system 130, keyboard, etc.).

In response to the user operation, user interface 325 or third-party application 250 may prompt the user to begin recording (e.g., via an icon and/or text on a user interface, a sound, a vibration, a light, etc.), and sound received through the microphone of user system 130 is then recorded. Another user operation may be used to end recording (e.g., selection of a soft or hard key, as described above, initiation of a photograph or video recording, etc.), or the recording may be automatically ended after a predefined time period (e.g., 5 seconds) or after no sound is detected for a predefined time period (e.g., 1 second).

Metadata-injection module 300 may receive this audio recording from quick-tag module 385, send or pass it to audio-to-text module 310 to be converted into text, and receive the text from audio-to-text module 310. Alternatively, quick-tag module 385 could perform the audio-to-text conversion or comprise audio-to-text module 310, as mentioned above, in which case quick-tag module 385 returns the text output to metadata-injection module 300. In either case, the text may be received by metadata-injection module 300 and injected into content item 302.

In an alternative embodiment, metadata-injection module 300 may inject the quick-tag audio recording, as metadata, into content item 302, without converting it to text, or in addition to injecting the text. In addition, the quick tag may be something other than an audio-recording. For example, the quick tag may comprise text which is entered into a user interface, instead of audio input into a microphone. Thus, as used herein, the term "quick tag" may refer to any type of user input, and the term "quick-tag metadata" may refer to the metadata derived from that user input. The quick-tag metadata may comprise the user input itself, portion(s) of the user input, a conversion of the user input (e.g., text output from an audio-to-text conversion of an audio quick-tag), and/or the like.

In an embodiment, the quick-tag metadata is injected, by metadata-injection module 300, into all or a subset of content items that are captured contemporaneously with the input of the quick-tag (e.g., contemporaneously with the recording of an audio input or receipt of a text input). This may be implemented, for example, in any one of the following manners:

(1) The quick-tag is recorded at time $T_1$. Metadata-injection module 300 adds the quick-tag metadata to any future content items created within $\Delta T$ of $T_1$, i.e., within the time period $\{T_1, T_1+\Delta T\}$.

(2) The quick-tag is recorded at time $T_1$. Metadata-injection module 300 adds the quick-tag metadata to any prior content items created within $\Delta T$ of $T_1$, i.e., within the time period $\{T_1-\Delta T, T_1\}$.

(3) The quick-tag is recorded at time $T_1$. Metadata-injection module 300 adds the quick-tag metadata to any prior or future content items created within $\Delta T$ of $T_1$, i.e., within the time period $\{T_1-\Delta T, T_1+\Delta T\}$. In this case, $\Delta T$ may be different for prior and future content items, such that metadata-injection module 300 adds the quick-tag metadata to any content items created within the time period between $\{T_1-\Delta T_1, T_1+\Delta T_2\}$, where $\Delta T_1 \neq \Delta T_2$.

(4) The quick-tag is recorded at time $T_1$. Metadata-injection module 300 adds the quick-tag metadata to the N most proximate content items created after $T_1$. For example, if N is five, and the first content items created after $T_1$ are, in chronological order, A, B, C, D, E, F, and G, metadata-injection module 300 would inject the quick-tag metadata into each of A-E, but not F and G.

(5) The quick-tag is recorded at time $T_1$. Metadata-injection module 300 adds the quick-tag metadata to the N most proximate content items created before $T_1$. For example, if N is five, and the content items created before $T_1$ are, in chronological order, A, B, C, D, E, F, and G, metadata-injection module 300 would inject the quick-tag metadata into each of C-G, but not A and B.

(6) The quick-tag is recorded at time $T_1$. Metadata-injection module 300 adds the quick-tag metadata to the N most proximate content items created before and after $T_1$. For example, if N is five, the content items created before $T_1$ are, in chronological order, A, B, C, D, E, F, and G, and the content items created after $T_1$ are, in chronological order, H, I, J, K, L, M, and O, metadata-injection module 300 would inject the quick-tag metadata into each of C-L, but not A, B, M, and O.

(7) The quick-tag is recorded at time $T_1$. Metadata-injection module 300 adds the quick-tag metadata to any future content items created within $\Delta T_1$ of $T_1$ or $\Delta T_2$ from an immediately preceding content item into which the quick-tag metadata was injected, where $\Delta T_2=\Delta T_1$ or $\Delta T_2 \neq \Delta T_1$. In an example, $T_1$=12:00 pm, $\Delta T_1$=10 minutes, $\Delta T_2$=5 minutes, and content item A is received at 12:05 pm, B at 12:07 pm, C at 12:11 pm, D at 12:12 pm, E at 12:17 pm, F at 12:26 pm, and G at 1:00 pm. In this example, content item A is received within $\Delta T_1$ of $T_1$ (i.e., 5 minutes<10 minutes), thus, content item A is injected with the quick-tag metadata. Content item B is received within $\Delta T_1$ of $T_1$ (i.e., 7 minutes<10 minutes) and also within $\Delta T_2$ of content item A (2 minutes<5 minutes), thus, content item B is also injected with the quick-tag metadata. Content item C is not received within $\Delta T_1$ of $T_1$ (i.e., 11 minutes>10 minutes) but is received within $\Delta T_2$ of content item B (i.e., 4 minutes<5 minutes), thus, content item C is also injected with the quick-tag metadata. Content item D is not received within $\Delta T_1$ of $T_1$ (i.e., 12 minutes>10 minutes) but is received within $\Delta T_2$ of content item C (i.e., 1 minutes<5 minutes), thus, content item D is also injected with the quick-tag metadata. Similarly, content item E is not received within $\Delta T_1$ of T1 (i.e., 17 minutes>10 minutes) but is received within $\Delta T_2$ of content item D (i.e., 5 minutes=5 minutes), thus, content item E is also injected with the quick-tag metadata. Content item F is not received within $\Delta T_1$ of $T_1$ (i.e., 26 minutes>10 minutes) and is not created within $\Delta T_2$ of a most recent preceding content item (i.e., 9 minutes from the most recent preceding content item E>5 minutes), thus, content item F is not injected with the quick-tag metadata. Similarly, content item G is also not injected with the quick-tag metadata.

In either of these implementations, $\Delta T$, $\Delta T_1$, $\Delta T_2$, and N may be set to any suitable value. As examples, $\Delta T$, $\Delta T_1$, and/or $\Delta T_2$ could be 30 seconds, 5 minutes, 10 minutes, 15 minutes, 30 minutes, 1 hour, 5 hours, 25 hours, etc., and N could be 5, 10, 20, 100, etc. Each of these values may be a user setting, such that the user can specify the values of $\Delta T$, $\Delta T_1$, $\Delta T_2$, and/or N via one or more user interfaces (e.g., provided by third-party application 250 or metadata-injection module 300).

The particular implementation used for determining which content items into which to inject the quick-tag metadata may also be a user setting, such that the user can specify whether he wants to add quick-tag metadata according to implementation (1), (2), (3), (4), (5), and/or (7) above via one or more user interfaces (e.g., provided by third-party application 250 or metadata-injection module 300).

In an embodiment, the user interface for setting the values and/or implementation may be provided at or near the time that the quick tag is received. For instance, the user interface for setting the values and/or implementation may be the same as the user interface for recording or receiving the quick tag in the first place. For example, the user interface that is provided in response to the user operation to input the quick tag may comprise inputs for entering or selecting the desired values for $\Delta T$, $\Delta T_1$, $\Delta T_2$, and/or N and/or the implementation (1)-(7) (or other) to be used.

In an embodiment, after a quick tag has been exhausted—e.g., after the time period for the quick tag has expired or the number of content items has been reached—metadata-injection module 300 may stop injecting quick-tag metadata (e.g., stop retrieving quick-tag metadata from quick-tag module 385) until another quick tag is received.

As an example, a user, prior to taking a photograph using his or her mobile device, may select a quick-tag button on a user interface provided by quick-tag module 385, and speak. The words spoken by the user are recorded and converted by quick-tag module 385 into text. Subsequently, when metadata-injection module 300 receives a new content item 302, metadata-injection module 300 retrieves the text from quick-tag module 385, and embeds the text, as metadata, into content item 302 to generate metadata-injected content item 304. Metadata-injection module 300 may continue to do this until the quick tag expires (e.g., after a certain amount of time or after a certain number of content items have been received and injected with the quick-tag metadata).

1.2.3.17. Point-of-Sale (POS) Module

In an embodiment, metadata-injection module 300 retrieves point-of-sale (POS) information from a POS module 390. For example, POS module 390 may comprise or be integrated in or interfaced with a POS system of a merchant. Metadata-injection module 300 may generate descriptive metadata from the POS information and inject it into content item 302 to create metadata-injected content item 304. It should be understood that, as with all of the metadata sources 220 (e.g., modules 310-390), metadata-injected content item 304 may be a non-composite or composite content item, as described elsewhere herein.

In an embodiment, the POS information retrieved from POS module 390 may comprise information related to a transaction occurring or which has previously occurred at a POS terminal, for example, in a merchant's retail location. For example, during the transaction, as a cashier scans a product being purchased, the barcode (e.g., captured using a conventional barcode scanner of the POS terminal) and/or an image of the product (e.g., captured by a camera at the POS terminal) may be passed as content item 302 to metadata-injection module 300 (e.g., by a third-party application 250 executing on the POS terminal or over a network at a central location within the merchant's POS system). Metadata-injection module 300 may retrieve the POS information from POS module 390 and inject it into content item 302 to create metadata-injected content item 304. It should be understood that other metadata may also be injected into content item 302. For example, if content item 302 comprises an image of the barcode on the scanned product, metadata-injection module 300 may pass the image of the barcode to AIDC module 365 to convert it into a product identifier, and then pass the product identifier returned by AIDC module 365 to asset module 375 to retrieve product information about the scanned product, which can then be added by metadata-injection module 300 to metadata-injected content item 304.

In an embodiment, the POS information may comprise a time of the transaction, a terminal identifier for the POS terminal which was used to conduct the transaction, a store identifier for the store in which the transaction was conducted, an employee identifier for the cashier who conducted the transaction, an identifier of the consumer who purchased the product, a price paid for the product, a method of payment, and/or the like. In addition, metadata-injected content item may be a non-composite content item, or may be a composite content item. As an example, for a transaction comprising a plurality of purchased products, a content item may be acquired for each of the purchased products (e.g., images of barcodes and/or the products themselves) in the transaction, and these content items may be composed into a composite image (i.e., comprised in metadata-injected content item 304) representing each of the products in the transaction.

1.2.3.18. Module Interactions

In an embodiment, information may be passed between one or more of the metadata sources 220 (e.g., modules 310-390), either directly via interfaces of the metadata sources or indirectly via metadata-injection module 300. For example, in the indirect case, metadata-injection module 300 may retrieve information from one metadata source and send or pass at least a portion of the retrieved information to another metadata source. In the direct case, one metadata source may request and receive information from another metadata source. A few non-limiting examples will now be described.

In an embodiment, metadata-injection module 300 may utilize information from scheduling module 340 and location module 335 to detect discrepancies with respect to scheduled metadata for a received content item. For instance, metadata-injection module 300 may extract metadata for an event from scheduling information received from scheduling module 340. If the metadata includes location information (e.g., an address, city, state, name of a place, GPS coordinates, etc.), metadata-injection module 300 may retrieve, from location module 335, location information representing a current location of the user device (e.g., that is executing third-party application 250 and/or metadata-injection module 300). At one or more times during the time period defined in the scheduling information (e.g., at the start of the time period, every fifteen minutes from the start of the time period, etc.), metadata-injection module 300 may compare the location information from the scheduling information to the current location information. If the comparison indicates that the location information does not match (e.g., the location information from the scheduling information and the current location information are mutually exclusive), this discrepancy may be flagged. As an example, the location information from the scheduling information may indicate that the user (and by implication, the user device) should be currently attending an event in San Diego, Calif., whereas the current location information may indicate that the user device is in Los Angeles, Calif., in which case the discrepancy may be flagged. On the other hand, if the location information from the scheduling information indicated that the user should be currently attending an event in San Diego, Calif., and the current location information indicated that the user device is at an address in San Diego, Calif., then no discrepancy is flagged.

When a discrepancy is detected, metadata-injection module 300, third-party application 250, or another module or application may prompt the user, using one or more user interfaces (e.g., user interface 325), to confirm, modify, and/or cancel the scheduled metadata to be associated with the content item. Using the example above, if the location information from the scheduling information indicates that the user is attending an event in San Diego and the current location information indicates that the user device is in Los Angeles, the user interface(s) may prompt the user with "Are you really in San Diego?" or "Are you in Los Angeles?" The user interface(s) may enable the user to modify the scheduled metadata and/or the scheduling information, confirm that the user is in Los Angeles and cancel the scheduled metadata, confirm that the user is in San Diego and proceed with the unmodified scheduled metadata, etc.

Similarly, in an embodiment, metadata-injection module may utilize information from scheduling module 340 and object-recognition module 320 to detect discrepancies with respect to scheduled metadata for a received content item. For instance, metadata-injection module 300 may extract metadata for an event from scheduling information received from scheduling module 340, and may receive the metadata associated with a reference object identified in the content item by object-recognition module 320. If the metadata includes location information (e.g., an address, city, state, name of a place, GPS coordinates, etc.) and the metadata associated with the reference object comprises location information (e.g., if the reference object represents a place or landmark), metadata-injection module 300 may compare the location information from the scheduling information to the location information from the metadata associated with the identified reference object. If the comparison indicates that the location information does not match (e.g., the location information from the scheduling information and the location information for the identified reference object are mutually exclusive), this discrepancy may be flagged. As an example, the location information from the scheduling information may indicate that the user (and by implication, the user device) should be attending an event in San Diego, Calif., whereas the identified reference object represents Mt. Rushmore and indicates South Dakota, in which case the discrepancy may be flagged. On the other hand, if the location information from the scheduling information indicated that the user should be attending an event in San Diego, Calif., and the identified reference object represents the USS Midway Museum, then no discrepancy is flagged. Discrepancies may be handled by prompting the user to confirm, modify, and/or cancel the scheduled metadata, as discussed above. It should be understood that this embodiment may be used in addition or as an alternative to the embodiment which utilizes current location information from location module 335.

As mentioned elsewhere herein, in an embodiment, metadata-injection module 300 may utilize information obtained from one or more of audio-to-text module 310, object-recognition module 320, user interface 325, location module 335, scheduling module 340, closed-captions module 360, AIDC module 365, and any of the other metadata sources 220 to retrieve contact information from contact module 370. As an example, audio-to-text module 310 may convert audio data from content item 302 into text, which may contain contact information, such as a person's name(s), nickname, title, employer, relationship, telephone number, email address, street address, and/or the like. This contact information may be returned to metadata-injection module 300, and sent or passed by metadata-injection module 300 to contacts module 370. Contacts module 370 may then use the received contact information to search the contacts database and return contact information derived from one or more matching contact records to metadata-injection module 300.

Similarly, object-recognition module may identify a face or other object in content item 302, and return object information associated with the matched reference object to metadata-injection module 300. Again, this object information may comprise first contact information (e.g., a name), and metadata-injection module 300 may send or pass this first contact information to contacts module 370 to retrieve second contact information from one or more contact records based on the first contact information.

As another example, user interface 325 may receive first contact information from a user (e.g., who may enter the contact information into one or more fields of user interface 325) and return this first contact information to metadata-injection module 300, which may then retrieve second contact information, based on the first contact information, from contacts module 370.

As another example, location module 335 may utilize current location information or location information received from metadata-injection module to identify metadata related to that location. For example, as described elsewhere herein, location module may search a locations database, comprising associations between location information and metadata, to identify metadata associated with location information within a vicinity of (e.g., within a predefined radius or encompassed by) the current location information. Location module 335 may then return any identified metadata to metadata-injection module 300. This returned metadata may comprise first contact information (e.g., an address). Metadata-injection module 300 may then send or pass this first contact information to contacts module 370 to retrieve second contact information, based on the first contact information.

As another example, metadata-injection module 300 may receive scheduling information, relevant to a particular time period related to content item 302 (e.g., time of creation of content item 302), from scheduling module 340 which comprises first contact information (e.g., a name, title, employer, relationship, telephone number, email address, and/or street address). Such contact information may be stored, for example, as event details in event information from which the scheduling information is derived. Metadata-injection module 300 may extract this first contact information from the scheduling information, and send or pass this first contact information to contacts module 370 to retrieve second contact information, based on the first contact information.

As another example, metadata-injection module 300 may receive metadata (e.g., extracted from closed captions associated with content item 302) from closed-captions module 360. This metadata may comprise first contact information (e.g., a name, title, employer, relationship, telephone number, email address, and/or street address). Such contact information may be spoken, for example, by one or more subjects of content item 302. Metadata-injection module 300 may extract this first contact information from the metadata, and send or pass this first contact information to contacts module 370 to retrieve second contact information, based on the first contact information.

As another example, metadata-injection module 300 may receive AIDC information (e.g., acquired from an AIDC code in content item 302) from AIDC module 365. The AIDC information may comprise first contact information (e.g., a name, title, employer, telephone number, email address, and/or street address). Such contact information may be encoded, for example, in an AIDC code, such as a bardcode or QR code. Metadata-injection module 300 may extract this first contact information from the AIDC information, and send or pass this first contact information to contacts module 370 to retrieve second contact information, based on the first contact information.

In an embodiment, metadata-injection module 300 may receive audio input from user interface 325, and send or pass the audio input to audio-to-text module 310 to be converted into text. Audio-to-text module 310 may return the text to metadata-injection module 300, which may utilize the returned text to generate metadata. Alternatively, audio-to-text module 310 may generate the metadata from the text and return the generated metadata to metadata-injection module 300. In either case, generating the metadata may comprise extracting character strings, to be used as metadata, from the text according to one or more criteria. These criteria may include, without limitation, proper names (e.g., names of people or places), frequently appearing words (e.g., a certain number of significant words that appear the most frequently), peculiar words (e.g., relatively uncommon words), words that are relevant to particular metatags for a standard file format (e.g., words matching, preceding, and/or following the name of a predefined metatag), etc. Alternatively, the entire text from audio-to-text module 310 may be used as the metadata. Regardless of how the metadata is generated, metadata-injection module 300 may inject the metadata into content item 302.

In an embodiment, metadata-injection module 300 may receive location information from location module 335, and send or pass this location information to weather module 345, as discussed elsewhere herein, to retrieve weather information relevant to the location represented in the location information. Additionally or alternatively, metadata-injection module 300 may receive time information from time module 330 and/or access time information associated with content item 302, and send or pass this time information to weather module 345, as discussed elsewhere herein, to retrieve weather information relevant to the time represented in the time information. It should be understood that metadata-injection module 300 may retrieve and send both the location information and time information to weather module 345 in order to retrieve weather information relevant to both the time and location represented in this information.

In an embodiment, metadata-injection module 300 may receive location information from location module 335, and send or pass this location information to news module 350, as discussed elsewhere herein, to retrieve news information relevant to the location represented in the location information. Additionally or alternatively, metadata-injection module 300 may receive time information from time module 330 and/or access time information associated with content item 302, and send or pass this time information to news module 350, as discussed elsewhere herein, to retrieve news information relevant to the time represented in the time information. It should be understood that metadata-injection module 300 may retrieve and send both the location information and time information to news module 350 in order to retrieve news information relevant to both the time and location represented in this information.

In an embodiment, metadata-injection module 300 may receive object information from object-recognition module 320, and send or pass this object information to AIDC module 365, as discussed above, to retrieve AIDC information relevant to an object (e.g., barcode, QR code, etc.) represented in the object information.

In an embodiment, metadata-injection module 300 may receive an asset identifier identifying a person or object from, for example, one or more of audio-to-text module 310 (e.g., an asset identifier spoken into a microphone), authorship module 315 (e.g., an identifier of the author associated with an authenticated account), object-recognition module 320 (e.g., which may convert a visual depiction of an asset identifier in an image into text, for example, via OCR), user interface 325 (e.g., an asset identifier manually input by a user), location module 335 (e.g., an asset identifier associated in a locations database with location information associated with content item 302), scheduling module 340 (e.g., an asset identifier in event details associated in event information with a time period relevant to content item 302), news module 350 (e.g., an asset identifier mentioned in a news feed), sensor(s) 355 (e.g., an asset identifier received in the output of a sensor), closed-captions module 360 (e.g., an asset identifier included in closed captions associated with content item 302), AIDC module 365 (e.g., an asset identifier decoded or received from a barcode, QR code, RFID tag, magnetic stripe, smart card, OCR, etc.), and contacts module (e.g., an identifier of a contact). Metadata-injection module 300 may send or pass this asset identifier to asset module 375, as discussed elsewhere herein, to retrieve asset information associated with the asset identifier.

In an embodiment, metadata-injection module 300 may receive scheduling information for a relevant time period (e.g., encompassing the creation time of content item 302) from scheduling module 340 which identifies one or more of the other metadata sources (e.g., any of metadata sources 310-335 and 345-390). In this embodiment, metadata-injection module 300 may retrieve metadata from the metadata source(s) identified in the scheduling information for the relevant time period.

1.2.4. Operation

In an embodiment, third-party application 250 may initiate communication with metadata-injection module 300, implemented using metadata SDK 210 or provided by metadata SDK 210. Third-party application 250 may be a client application, such as application 132, executing on a user system 130, and may send or pass a content item 302 to metadata-injection module 300. Third-party application 250 may be an application for capturing or otherwise generating content item 302, and/or may be an application which manages (e.g., loads, manipulates, edits, etc.) previously-generated content items 302.

Metadata-injection module 300 may be locally executed on user system 130, and may be incorporated into third-party application 250 or separate from third-party application 250. Alternatively, metadata-injection module 300 may be executed on a remote system, such as metadata server 110, and third-party application 250 may send content item 302 to metadata-injection module 300 executing on metadata server 110 over network(s) 120.

In an embodiment, metadata-injection module 300 receives content item 302 from third-party application 250, and injects appropriate metadata, such as location information (e.g., GPS information), event information (e.g., from an appointment book or calendar), weather information (e.g., from a weather service), news information (e.g., from a news service), custom information (e.g., from a custom third-party service), etc., as described elsewhere herein. Specifically, metadata-injection module 300 may aggregate the metadata from one or more (including potentially all) of metadata sources 220 (e.g., metadata sources 310-390), which may be local (e.g., on the same device) and/or remote (e.g., over network(s) 120) to metadata-injection module 300.

Content item 302 sent or passed from third-party application 250 to metadata-injection module 300 may be included in a request that specifies or otherwise identifies one or more metadata sources from which metadata should be aggregated and/or includes other parameters. In this case, metadata-injection module 300 may parse the request, and retrieve the metadata from each of the one or more metadata sources identified in the request. In this case, the determination of which metadata sources to use may be based on a user setting which may be set, for example, via one or more user interfaces of third-party application 250 or a system or programmatic setting which may be set, for example, by the third-party developer of third-party application 250. In this manner, a user or third-party developer could specify the metadata sources 220 to be used by metadata-injection module 300.

Alternatively, metadata-injection module 300 may otherwise determine from which of metadata sources 220 to retrieve metadata. As discussed elsewhere herein, this determination may be based, at least in part, on the type of content item 302 (e.g., photograph, video, etc.). For example, metadata-injection module 300 may query a table or other data structure using the content item type to retrieve a subset of available metadata sources which are applicable to the content item type. Alternatively, metadata-injection module 300 may simply attempt to retrieve metadata from all available metadata sources.

As another alternative, this determination of metadata sources may be based on scheduling information received from scheduling module 340. In such an embodiment, metadata-injection module 300 may always retrieve scheduling information relevant to content item 302 (e.g., scheduling information comprising a time period encompassing a creation time of content item 302) from scheduling module 340, and select additional metadata sources based on which metadata sources are identified in the scheduling information. In this manner, metadata sources may be scheduled. That is, the metadata sources to be used for metadata injection may be defined by a user for a particular time period in advance of that time period. In addition, the request may comprise other parameters.

Regardless of how the metadata sources to be used are identified or determined or if all available metadata sources are utilized, metadata-injection module 300 retrieves the metadata (e.g., from local sources, and/or from remote sources, for example, over network(s) 120) from each of the determined metadata source(s) and injects the retrieved metadata into, or otherwise associates the retrieved metadata with, the received content item. Specifically, as described in more detail elsewhere herein, metadata-injection module 300 may embed the retrieved metadata into metadata fields of content item 302 incorporate the retrieved metadata into a sidecar file associated with content item 302, and/or generate a composite content item comprising both content item 302 and a visual depiction of metadata (e.g., an image returned as metadata).

Once the metadata, retrieved from one or more metadata sources 220, have been injected into the content item, received from third-party application 250, metadata-injection module 300 may return the metadata-injected content item 304 to third-party application 250. Alternatively or additionally, metadata-injection module 300 may notify third-party application 250 (e.g., via a response to the request) that the metadata injection has been successful, and/or send metadata-injected content item 304 to metadata server(s) 110 for storage in one or more storage destinations 230. Whether metadata-injection module 300 returns metadata-injected content item 304 to third-party application 250, stores metadata-injected content item 304 in a storage destination 230 (e.g., in cloud storage), or does both may be a system setting defined by third-party application 250 and/or a user setting provided by third-party application 250 which a user may specify (e.g., via one or more user interfaces displayed on a display by third-party application 250).

Alternatively or additionally, once the metadata has been injected into the content item, metadata-injection module 300 may send or pass the metadata-injected content item 304, directly or indirectly, to a media production or editing application (e.g., application(s) within Adobe Creative Suite™ or Adobe Creative Cloud™, application(s) within Avid Artist Suite™ Apple FinalCut Pro™, etc.). The media production or editing application may be local to metadata-injection module 300 (e.g., executing on the same user system 130). Alternatively, the media production or editing application may be remote from metadata-injection module 300 (e.g., executing on a different system), in which case metadata-injection module 300 may send the metadata-injected content item 304 to the media production or editing application over network(s) 120. In either case, metadata-injection module may utilize an API to send the metadata-injected content item 304 to the media production or editing application, or may pass the metadata-injected content item 304 to an intermediate module (e.g., a module of third-party application 250) which utilizes an API to send the metadata-injected content item 304 to the media production or editing application. In the above manner, the metadata-injected content item 304 may be automatically (e.g., without user intervention) or semi-automatically (e.g., in response to a user confirmation) imported into a media production or editing application. The media production or editing application may allow a user, for example, to edit the metadata-injected content item 304 (e.g., crop, apply filters or effects, alter attributes, change content, etc.), incorporate at least a portion of the metadata-injected content item 304 into another content item, combine at least a portion of the metadata-injected content item 304 with one or more other content items, publish the metadata-injected content item 304, and/or the like.

In an embodiment in which metadata-injected content item 304 is sent by metadata-injection module 300 to metadata server(s) 110 for storage, metadata server(s) 110 may send the metadata-injected content item to one or more storage destinations 230, which may be comprised in metadata server(s) 110 or remotely accessible to metadata server(s) 110 (e.g., via network(s) 120). Metadata server(s) 110 may select the storage destination(s) to which the metadata-injected content item is sent to be stored based on a system setting and/or user setting. Alternatively or additionally, the storage destination(s) may be specified or otherwise identified in the request, comprising metadata-injected content item 304, that is sent by metadata-injection module 300 to metadata server(s) 110. In this case, a user may specify the storage destination(s) to which metadata-injected content item 304 is sent to be stored (e.g., via one or more user interfaces displayed on a display by third-party application 250).

In any case, metadata server(s) 110 may optionally send a notification that metadata-injected content item 304 has been successfully stored. As illustrated in FIG. 2, this notification may be sent by metadata serve(s) 110 to a third-party platform 240 that supports third-party application 250. However, it should be understood that alternatively or additionally, this notification may be sent by metadata server(s) 110 to third-party application 250 either directly (e.g., via network(s) 120) or indirectly (e.g., by sending it to metadata-injection module 300, which in turn returns it to third-party application 250), and/or any other recipient.

Additionally or alternatively, in an embodiment, after a metadata-injected content item 304 has been received and/or stored by metadata server(s) 110, metadata server(s) 110 may push real-time metadata to third-party platform 240, in addition to or instead of sending a notification to third-party platform 240. Third-party platform 240 may utilize this metadata to provide improved searching capabilities for content items. For example, third-party platform 240 may store and organize the received metadata for each metadata-injected content item 304 (e.g., associated with a particular user) either on third-party platform 240 (or remote storage accessible to third-party platform 240) or at the user system executing third-party application 250, such that the metadata is associated with the content item (e.g., via an identifier of the content item) into which it was injected, and can be searched. Thus, a user, when searching for a particular content item, may enter a query (e.g., one or more keywords), and either third-party application 250 or third-party platform 240 supporting the third-party application 250 may search the stored metadata based on the query and return one or more content items associated with matching metadata (e.g., metadata comprising the one or more keywords of a query).

An example of how a third-party application (e.g., third-party application 250) may utilize the metadata SDK (e.g., metadata SDK 210) will now be described, according to an embodiment. A third-party developer may develop a third-party client application (e.g., third-party application 250 or application 132 executing on user system 130) which obtains content items. Client application 250 may capture the content item, and/or may simply receive the content item (e.g., from a capture device, from a scanning device, from another application, by user selection, etc.). For example, the client application may be interfaced with a camera of a user system (e.g., a camera of a smartphone, a webcam of a laptop computer, etc.) to capture a photograph or video (e.g., in response to a user input via a hard or soft key). After the content item has been captured, the client application may initiate a call to an internal procedure that implements a metadata-injection module (e.g., class) specified by the metadata SDK or incorporates a metadata-injection module (e.g., library) provided by metadata SDK, or may initiate a remote procedure call to a metadata-injection module (e.g., executing on metadata server(s) 110).

The content item (e.g., content item 302) may be sent to the metadata-injection module (e.g., metadata-injection module 300) automatically whenever a content item has been captured via the client application, semi-automatically in response to user confirmation to a prompt that is presented to the user whenever a content item has been captured via the client application, and/or manually in response to a user input (e.g., via a hard or soft key at any time after the content item has been captured). The client application may implement the decision of when the captured content item is sent to the metadata-injection module as a user setting, such that a user may specify whether content items, captured via the client application, should be sent automatically, semi-automatically, or manually (e.g., via one or more user interfaces generated by the client application on a display of the user system). It should be understood that a plurality of content items may be sent to the metadata-injection module (e.g., metadata-injection module 300) to be injected with metadata in a batch process. The systems and processes may be the same as for a single content item (e.g., content item 302), but applied to multiple content items.

Continuing the example, the metadata-injection module (whether local or remote) receives the captured photograph from the client application and may inspect all available sources. Alternatively, the metadata-injection module may inspect a subset of the available sources—for example, corresponding to sources identified in the request sent by or invoked by the client application and comprising the captured photograph, or corresponding to sources that are relevant to photographs—to identify whether those sources have available metadata. As a non-limiting example, the metadata-injection module may check one or more other applications (e.g., a calendar or contact application associated with the user of the client application, and/or executing on the same user system on which the client application is executing), a GPS (within the user system on which the client application is executing), and/or additional sensors integral, interfaced, and/or communicatively connected with the user system on which the client application is executing. The metadata-injection module collects metadata from these sources, and "injects" them into the content item (e.g., by inserting the metadata into embedded metadata fields of the content item or a sidecar file associated with the content item, or generating a composite content item). The metadata-injection module may then return this metadata-injected content item to the client application. Alternatively or additionally, the metadata-injection module may upload the metadata-injected content item to a server (e.g., metadata server(s) 110) for storage. In this case, the server stores the metadata-injected content item and may notify an external platform (e.g., third-party platform 240), that supports the client application, that the content item has been stored. In addition, the server may provide all the metadata that has been injected into the content item to the external platform supporting the client application.

The external platform may utilize this metadata to provide improved searching capabilities for content items. For example, the external platform may store and organize the received metadata for each metadata-injected content item (e.g., associated with a particular user) either on the external platform or at the user system executing the client application, such that the metadata is associated with the content item (e.g., via an identifier of the content item) into which it was injected, and can be searched. Thus, a user, when searching for a particular content item, may enter a query (e.g., one or more keywords), and either the client application or the external platform supporting that client application may search the stored metadata based on the query and return one or more content items associated with matching metadata (e.g., metadata comprising the one or more keywords of a query).

2. Process Overview

Embodiments of process(es), which may be implemented by the above described system(s), will now be described in detail. It should be understood that the described process(es) may be embodied in one or more software modules that are executed by one or more hardware processors. The described process may be implemented as instructions represented in source code, object code, and/or machine code. These instructions may be executed directly by the hardware processor(s), or alternatively, may be executed by a virtual machine operating between the object code and the hardware processors. In addition, the disclosed module(s) may be built upon or interfaced with one or more existing systems. Furthermore, the software modules may be integrated in a stand-alone application, an extension of another application, or integrated into an operating system. Alternatively, the process(es) may be embodied in hardware components, such as in an embedded system or integrated circuit (IC), or a combination of software and hardware components. Accordingly, as used herein, the term "module" should be interpreted as contemplating a software module, a hardware module, and a module comprising a combination of software and hardware. Furthermore, the term "module" or "modules," whether used in the singular or plural form should be interpreted as encompassing both a single module and, alternatively, a plurality of modules.

In an embodiment, the disclosed processes for adding descriptive metadata to content items are implemented as software modules that are executed entirely on user system 130, entirely on server(s) 110, or distributed between user system 130 and server(s) 110 (e.g., some modules executed on user system 130, as application 132, and some modules executed on server(s) 110).

2.1. Metadata Injection

Figure 4:
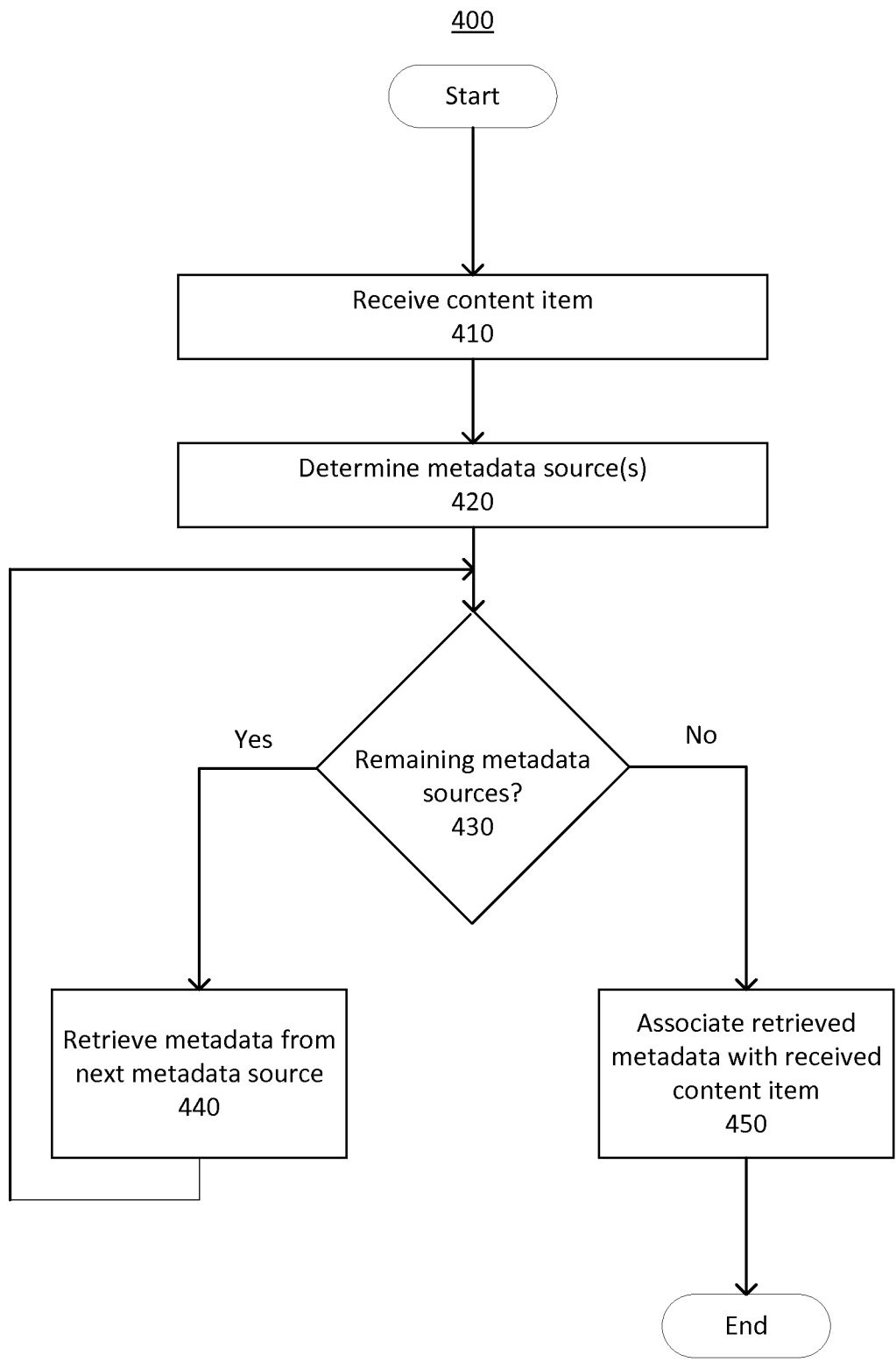
FIG. 4 illustrates a process of injecting metadata into a content item, according to an embodiment.

FIG. 4 illustrates a high-level flow diagram for a process 400 of injecting metadata into a content item, according to an embodiment. Process 400 may be implemented by metadata-injection module 300 described herein. This metadata-injection module may be a software module that is specified in an API of metadata SDK 210, implemented by a third-party developer, and incorporated in third-party application 250. Alternatively, the metadata-injection module may be provided as a pre-written library of metadata SDK 210 that is accessible via a specified procedure call and/or executed by metadata server 110, such that third-party application 250 may call the metadata-injection module (e.g., passing the content item, possibly with one or more parameters, to the metadata-injection module) either locally on a user system 130 (if the metadata-injection module is locally executed) or remotely on metadata server 110 (e.g., via a remote procedure call over network(s) 120 if the metadata-injection module is remotely executed).

Process 400 begins in step 410, when a content item is received. The content item may be received in a request or procedure call along with one or more parameters or other data, such as an identification of the type of content item, an identification of one or more metadata sources (e.g., metadata sources 220) to be used, one or more storage destinations (e.g., storage destinations 230) to which the content item should be sent following the metadata injection, etc.

In step 420, metadata source(s) (e.g., metadata sources 220, 310-390) are determined. In an embodiment in which metadata sources are identified in the request that is received in step 410, this determination simply comprises accessing those identifications of the metadata sources.

Additionally or alternatively, the metadata sources may be determined in step 420 based, at least in part, on the type of the content item (e.g., image, video, etc.). The type of the content item may be identified in the request that is received in step 410, in which case the type of the content item may be determined by simply accessing that parameter from the request. Alternatively, the type of the content item may be determined by analyzing the content item. In either case, process 400 may select one or more metadata sources that are associated with the determined type of the content item. For example, process 400 may access a table or other data structure which associates each available metadata source (e.g., each metadata source 220, 310-390) with one or more content item types. This data structure may be searched based on the determined content item type to identify a subset of the available metadata sources which are associated with the determined content item type. This subset of available metadata source(s) are the determined metadata source(s) that are used in the subsequent steps of process 400.

Additionally or alternatively, the metadata sources may be determined in step 420 based, at least in part, on scheduling information, as described elsewhere herein. For instance, process 400 may retrieve scheduling information (e.g., from scheduling module 340) relevant to a time of creation of the content item received in step 410. This scheduling information may identify the metadata source(s) to be used. Therefore, the determination of metadata source(s) in step 420 may comprise parsing the scheduling information to identify these metadata source(s).

In steps 430 and 440, each of the metadata source(s) determined in step 420 is checked. Specifically, in step 430, it is determined whether any of the metadata source(s) determined in step 420 remain to be checked. If so (i.e., "Yes" in step 430), in step 440, the next metadata source (e.g., identified in an array or linked list of metadata sources generated in step 420) is checked. Checking a metadata source in step 440 may comprise sending a request for metadata to the metadata source and receiving a response to the request comprising the requested metadata, receiving real-time metadata from the metadata source, retrieving metadata previously received from the metadata source (e.g., previously requested and received on a periodic basis, previously pushed from the metadata source, etc.), etc.

Once metadata has been retrieved from each metadata source determined in step 420 (i.e., "No" in step 430), the retrieved metadata from all of these metadata sources are injected into, or otherwise associated with, the content item that was received in step 410. Alternatively, retrieved metadata from each metadata source may be injected into the content item as it is retrieved (e.g., after step 440 or in parallel with the loop formed by steps 430 and 440). In either case, the retrieved metadata may be analyzed or otherwise processed before it is associated with the received content item.

This processing may comprise deriving the metadata to be associated with the received content item from the metadata that is retrieved from the metadata source(s) in step 440. In other words, the data retrieved from these metadata source(s) may be processed into the metadata to be injected or otherwise associated with the received content item. This processing may comprise, for example, parsing or extracting the metadata from the data retrieved in step 440 (e.g., extracting text from fields of the retrieved data), formatting the data retrieved in step 440 into the metadata, or otherwise transforming or converting the data retrieved in step 440 into metadata for the content item.

2.2. Metadata Scheduling

Figure 5:
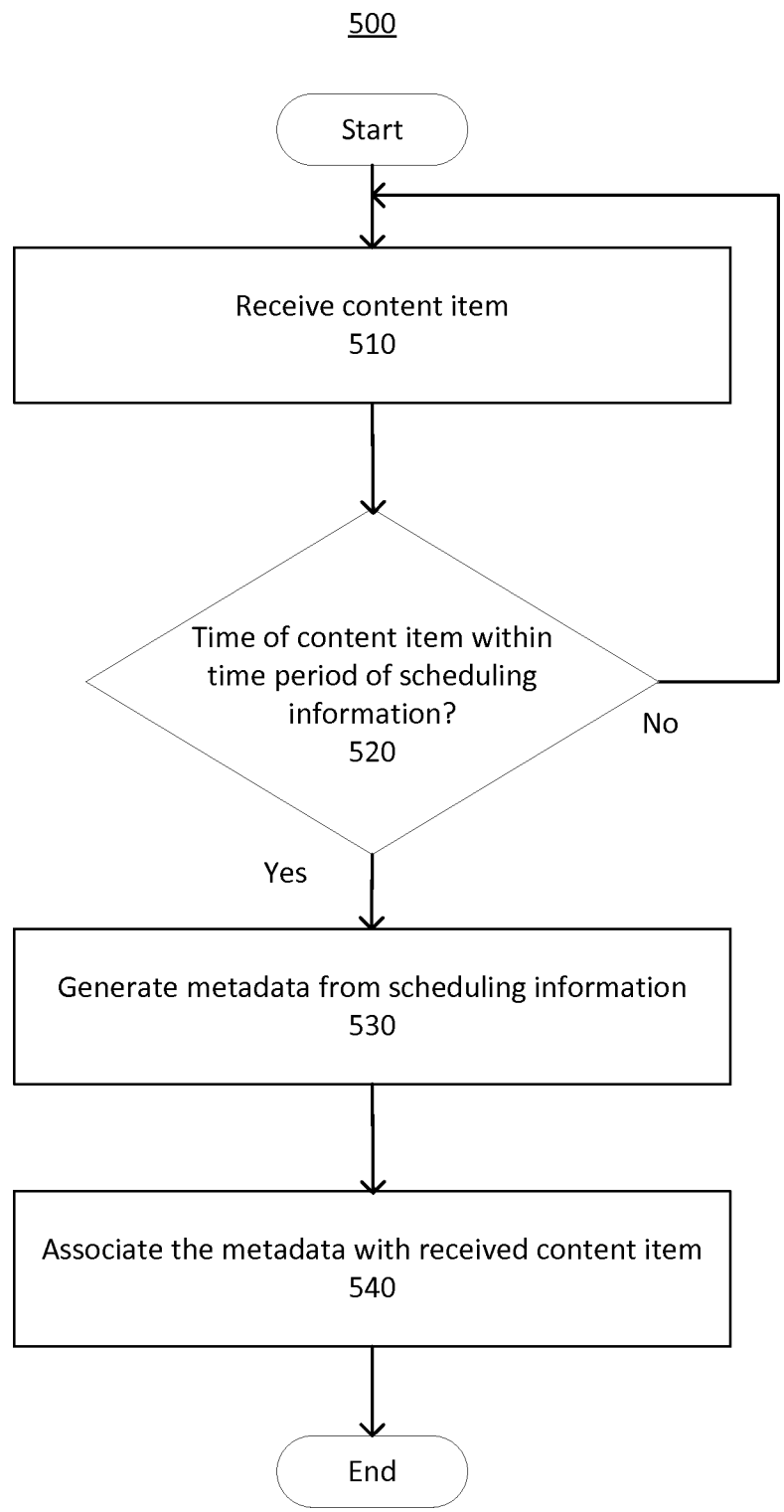
FIG. 5 illustrates a process for associating scheduled metadata with content item(s), according to an embodiment.

FIG. 5 illustrates a process 500 for associating scheduled metadata with content item(s), according to an embodiment. Process 500 may be implemented by metadata-injection module 300, scheduling module 340, and/or a combination of metadata-injection module 300 and scheduling module 340. Process 500 begins in step 510, when a content item (e.g., content item 302) is received (e.g., by metadata-injection module 300).

In step 520, time data (e.g., timestamp) associated with the content item is compared to one or more time periods in scheduling information. This comparison may be performed by scheduling module 340 in response to a request that comprises the time data, or may be performed by metadata-injection module 300 after receiving scheduling information from scheduling module 340, as discussed elsewhere herein. In either case, the comparison may comprise comparing a timestamp associated with the content item ($T_c$) to a time range associated with one or more events in the scheduling information. For example, the time range may comprise a start timestamp ($T_s$), an end timestamp ($T_e$), or both a start and end timestamp. If the time range comprises a start timestamp only, the timestamp associated with the content item is encompassed by the time range if it is subsequent to the start timestamp, i.e., $T_c \geq T_s$. If the time range comprises an end timestamp only, the timestamp associated with the content item is encompassed by the time range if it precedes the end timestamp, i.e., $T_c \leq T_e$. If the time range comprises both a start timestamp and an end timestamp, the timestamp associated with the content item is encompassed by the time range if it is between the start and end timestamps, i.e., $T_s \leq T_c \leq T_e$.

If the time data is not encompassed by one or more time periods in the scheduling information (i.e., "No" in step 520), no metadata is generated from the scheduling information, and process 500 waits to receive another content item. It should be understood that, even though no metadata is generated from the scheduling information, this does not preclude the possibility of generating metadata from other metadata sources.

On the other hand, if the time data is encompassed by one or more time periods in the scheduling information (i.e., "Yes" in step 520), metadata is generated from the associated scheduling information in step 530 (e.g., by metadata-injection module 300 or scheduling module 340). Alternatively, the generation of metadata in step 530 may be performed in advance of step 520 and/or step 510. In this case, metadata may be generated for all available scheduling information, and the pre-generated metadata may be associated with content items based on a comparison of a timestamp, related to a content item received in step 510, with a time period associated with scheduling information from which the metadata was previously generated or associated with the pre-generated metadata itself.

In either case, metadata may be generated from the scheduling information by extracting one or more words or character strings from text in one or more fields of the scheduling information, and/or by using a character string stored in a specific, dedicated metadata field of the scheduling information (e.g., a description field). The scheduling information may comprise event information with one or more event details and one or more parameters (e.g., start and end timestamps) defining a time period. As an example, for an event represented in the scheduling information with a description of "Lunch with John Smith," the character strings "Lunch" and "John Smith" may be extracted as metadata. Also, as described elsewhere herein, metadata generated from nested events represented in the scheduling information may be concatenated or otherwise combined for injection into the content item received in step 510 (e.g., content item 302). For example, if the scheduling information comprises a first event of "Meeting with John Smith" from 10:00 am to 2:00 pm and a second event of "Lunch at ABC Restaurant" from 12:00 pm to 1:00 pm on the same day, the second event is nested within the first event. Thus, the metadata generated in step 530 for a content item with a timestamp representing 12:30 pm on the same day may include both event descriptions or character string(s) extracted from both event descriptions (e.g., "John Smith", "Lunch", and "ABC Restaurant").

In step 540, the relevant metadata generated in step 530 is associated with the content item received in step 510, and process 500 ends. As discussed elsewhere herein the metadata may be embedded into metatags or other fields of the content item, added to a sidecar file associated with the content item, and or used to generate a composite content item.

2.3. Metadata Aggregation

Figure 6:
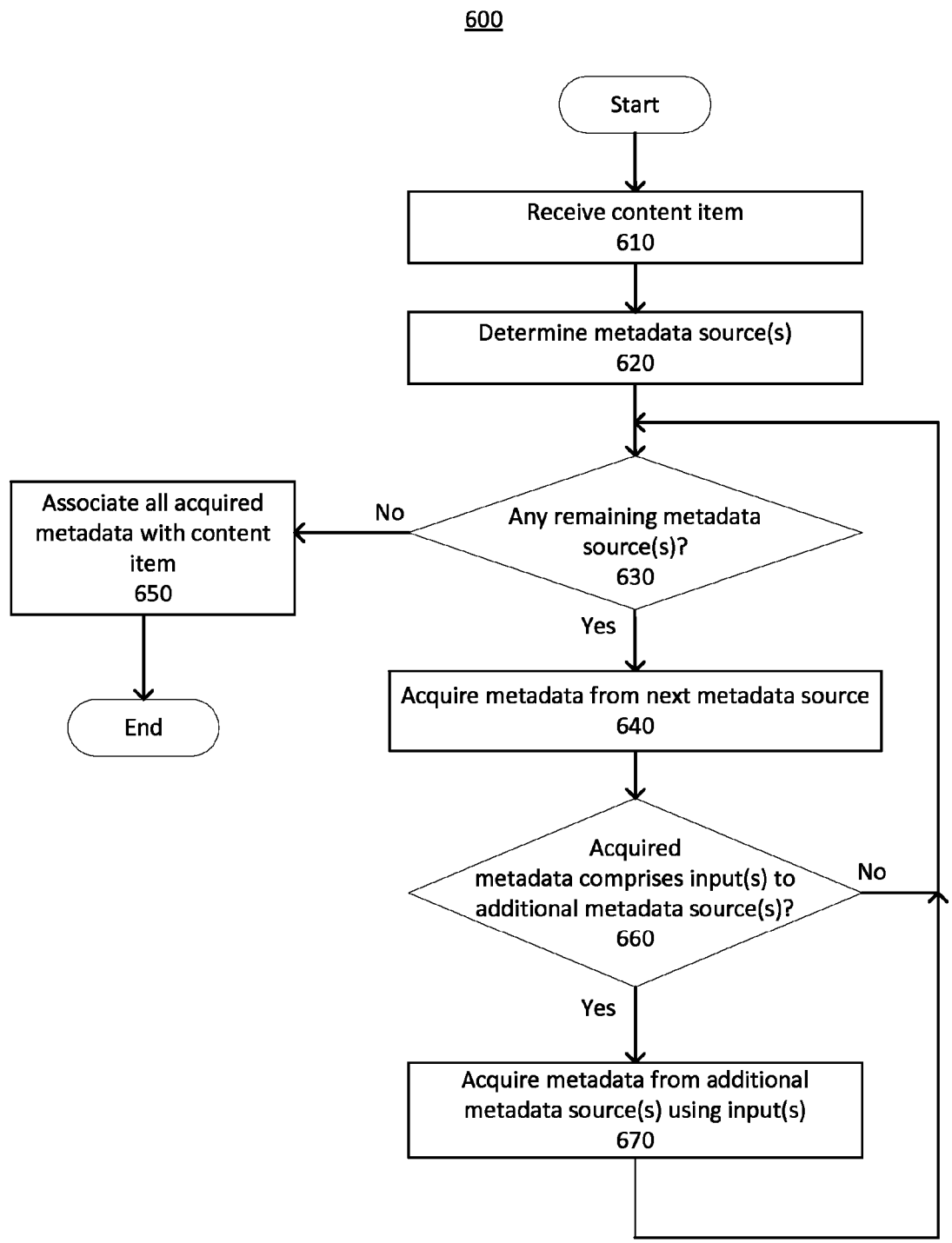
FIG. 6 illustrates a process for aggregating metadata from multiple metadata sources, according to an embodiment.

FIG. 6 illustrates a process 600 for aggregating metadata from multiple metadata sources (e.g., metadata sources 220, 310-390), according to an embodiment. This process may be implemented, for example, by metadata-injection module 300. Process 600 is similar to process 400. However, process 600 illustrates the potential relationships between multiple metadata sources. Steps 610, 620, 630, 640, and 650 in process 600 may be identical or similar to steps 410, 420, 430, 440, and 450, respectively, in process 400. Therefore any descriptions of steps 410, 420, 430, 440, and 450 may apply equally to steps 610, 620, 630, 640, and 650, respectively, and vice versa.

Process 600 starts in step 610, in which a content item is received. In step 620, one or more metadata sources are determined, for example, based on the type of content item received in step 610 and/or one or more parameters received with the content item(s) in step 610, or based on scheduling information. Alternatively, all metadata sources may be consulted, regardless of the type of content item received in step 610 and any parameters, in which case step 620 may be unnecessary and omitted.

In step 630, if metadata source(s) remain to be checked from the metadata source(s) determined in step 620 (i.e., "Yes" in step 630), process 600 proceeds to step 640. Otherwise (i.e., "No" in step 630), process 600 proceeds to step 650, in which all acquired metadata is associated with the content item(s) received in step 610, and process 600 ends. However, it should be understood that step 650 may occur in parallel or interspersed with the other steps (e.g., after steps 640 and/or 670), such that metadata is associated with the content item(s) received in step 610 as that metadata is acquired. In addition, as discussed elsewhere herein, at least a portion of the metadata may be associated with the content item(s) by generating a visual depiction of the metadata, and generating a composite content item (e.g., composite image) comprising each of the content item(s) (which may be a plurality of content items) and the visual depiction of the metadata. It should be understood that metadata (e.g., any remaining non-visually-depicted metadata) may also be associated with the composite image using embedded fields or a side car file.

In step 640, metadata is acquired (e.g., in a manner discussed elsewhere herein) from the next metadata source in the set of metadata source(s) determined in step 620.

In step 660, process 600 determines whether or not the metadata acquired in step 640 comprises one or more inputs which can be used to acquire additional metadata from one or more additional metadata sources. For example, metadata acquired from one metadata source and comprising first contact information (e.g., name(s), title, employer, relationship, telephone number(s), email address(es), street address (es), etc.) may be input to contacts module 370 to acquire second contact information based on the first contact information, as discussed elsewhere herein. As another example, location information acquired from location module 335 may be input to object-recognition module 320 to facilitate object recognition by restricting searching based on the location information.

If the metadata acquired in step 640 does comprise input(s) which can be used to acquire additional metadata from one or more additional metadata source(s) (i.e., "Yes" in step 660), process 600 proceeds to step 670. Otherwise (i.e., "No" in step 660), process 600 returns to step 630. In step 670, metadata is acquired (e.g., in the manner discussed elsewhere herein) from the additional metadata source(s) using one or more of the input(s) as an input to the respective metadata source. Then, process 600 returns to step 630.

2.4. Scheduled Metadata Sources

Figure 7:
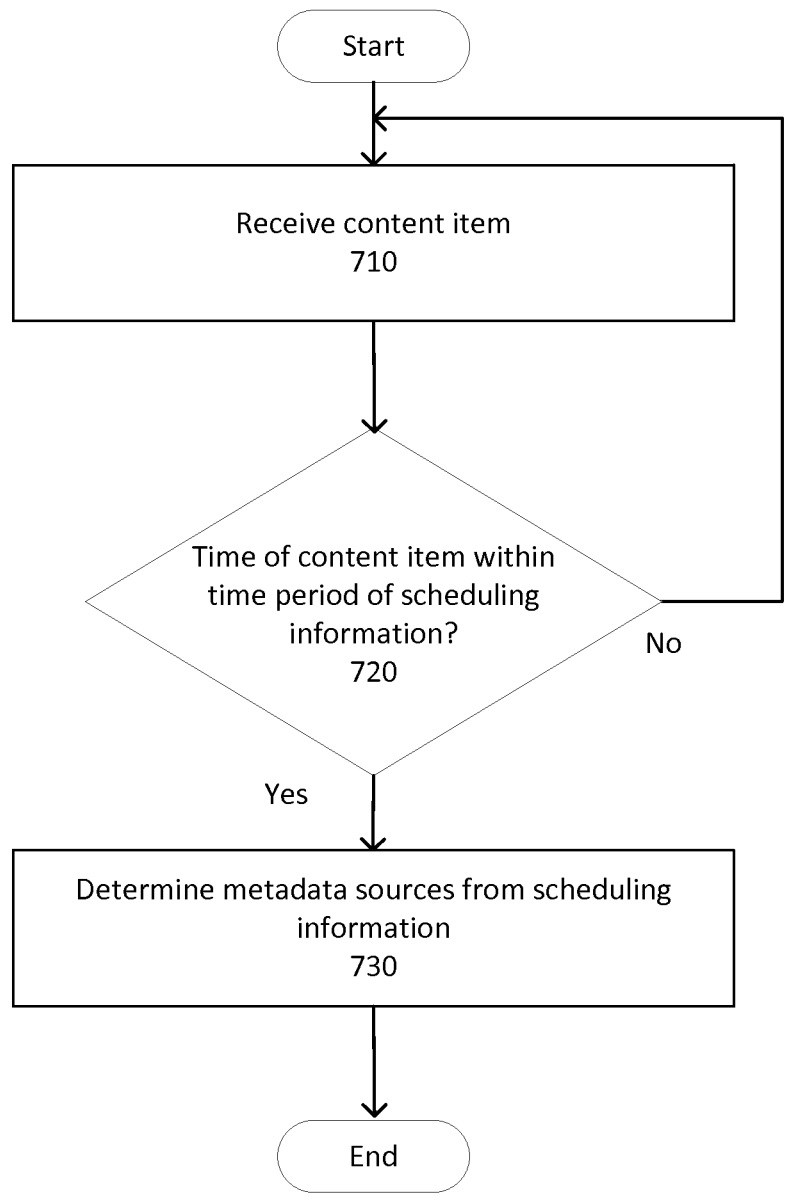
FIG. 7 illustrates a process for scheduling metadata sources, according to an embodiment.

FIG. 7 illustrates a process 700 for scheduling metadata sources (e.g., metadata sources 220, 310-335 and 345-390), according to an embodiment. Process 700 may correspond to step 420 in process 400 and/or step 620 in process 600.

Process 700 starts in step 710, in which a content item is received. In step 720, time data (e.g., timestamp) associated with the content item is compared to one or more time periods in scheduling information. This comparison may be performed by scheduling module 340 in response to a request that comprises the time data, or may be performed by metadata-injection module 300 after receiving scheduling information from scheduling module 340, as discussed elsewhere herein. In either case, the comparison may comprise comparing a timestamp associated with the content item ($T_c$) to a time range associated with one or more events in the scheduling information. For example, the time range may comprise a start timestamp ($T_s$), an end timestamp ($T_e$), or both a start and end timestamp. If the time range comprises a start timestamp only, the timestamp associated with the content item is encompassed by the time range if it is subsequent to the start timestamp, i.e., $T_c \geq T_s$. If the time range comprises an end timestamp only, the timestamp associated with the content item is encompassed by the time range if it precedes the end timestamp, i.e., $T_c \leq T_e$. If the time range comprises both a start timestamp and an end timestamp, the timestamp associated with the content item is encompassed by the time range if it is between the start and end timestamps, i.e., $T_s \leq T_c \leq T_e$.

If the time data is not encompassed by one or more time periods in the scheduling information (i.e., "No" in step 720), no metadata sources are determined. In this case, no metadata may be injected into the content item received in 710. Alternatively, there may be a default set of metadata sources which are used for metadata injection, and/or there may be a fixed set of metadata sources that are always used for metadata injection. For example, in steps 420 and/or 620 of processes 400 and/or 600, respectively, if no scheduling information applies to the time associated with the content item or the applicable scheduling information does not identify any metadata sources, the respective process may proceed using this default and/or fixed set of metadata sources.

On the other hand, if the time data is encompassed by one or more time periods in the scheduling information (i.e., "Yes" in step 720), the metadata sources to be used for metadata-injection (e.g., by metadata-injection module 300) are determined from the associated scheduling information in step 730.

3. Metadata Injection

As discussed elsewhere herein, metadata injection, as described herein, generally refers to the association of metadata with a content item. This association may comprise incorporating (e.g., embedding) the metadata into the content item, incorporating the metadata into a sidecar file associated with the content item, and/or generating a composite content item.

In an embodiment in which metadata is embedded into a content item, the content item may comprise metadata fields, provided according to a standard (e.g., EXIF, IIM, XMP, etc.). Thus, the metadata-injection module (e.g., metadata-injection module 300) may input metadata into the corresponding metadata fields provided by the standard.

However, these standards do not generally anticipate the multiplicity of descriptive metadata enabled by the disclosed metadata-injection module, and frequently only provide embedded fields for technical metadata. Thus, in an embodiment, the metadata-injection module may "abuse" the embedded fields provided by such standards by inputting metadata that was not intended for a particular field into the field.

In such an embodiment, the metadata-injection module (e.g., metadata-injection module 300) or the third-party application (e.g., third-party application 250) may maintain a mapping of types of metadata to standard fields for each supported standard. In an embodiment in which the third-party application maintains this mapping, third-party application 250 may send or pass the mapping to the metadata-injection module (e.g., along with the content item) to be used by the metadata-injection module during the injection of metadata into the content item. It should be understood that different third-party applications or different implementations of the metadata-injection module may use the same or different mappings, and/or may modify their respective mappings over time or allow users to modify the mappings (e.g., according to user settings).

In an embodiment, the metadata-to-field mapping comprises a plurality of associations that associate a type of metadata with a field of a supported standard. The mapping may provide such associations for a plurality of standards, and may provide the associations for at least a subset of fields in each of the plurality of standards. As an example, the mapping may be represented or expressed as a table which comprises rows for each supported standard, as illustrated in the following table:

| | Standard | Field | Metadata Type |
|---|---|---|---|
| 1 | EXIF | Make | Weather1 |
| 2 | EXIF | Model | Weather2 |
| 3 | EXIF | Description | ClosedCaptions |
| ... | ... | ... | ... |
| 50 | IPTC | By-Line | Authorship |
| 51 | IPTC | By-Line Title | Weather |
| 52 | IPTC | Contact | Contacts |
| ... | ... | ... | ... |

In an embodiment, the metadata-to-field mapping may only store associations for those fields that are being abused, i.e., not being used according to their intended purpose. In other words, fields which are to be used by the metadata-injection module according to their intended purpose or which are not used by the metadata-injection module may not be represented in the mapping. Also, as illustrated by lines 1 and 2 in the above table, metadata of a single type may be split across multiple fields, for example, if one field is not sufficient for the expected volume of metadata of that type.

When inputting metadata into the embedded fields of each content item that utilizes one of these standards, the metadata-injection module may, for each metadata type (e.g., authorship, location, events, weather, news, sensor output, AIDC, contacts, assets, etc.), consult the metadata-to-field mapping to determine the field into which the metadata of that type should be input, and input the metadata accordingly.

In an embodiment in which the metadata-to-field mapping is maintained by the third-party application (e.g., third-party application 250), a reverse mapping (i.e., a field-to-metadata mapping) can be used to translate embedded fields back into the appropriate type of metadata. This field-to-metadata mapping may use the same data structure as the metadata-to-field mapping, and may be maintained at the third-party application or a third-party platform (e.g., third-party platform 240) supporting the third-party application.

The field-to-metadata mapping can be used for the purposes of searching or filtering content items based on the type of metadata. For example, a user interface provided by the third-party application or third-party platform may allow a user to specify one or more metadata types on which to search and/or filter stored metadata-injected content items. The third-party application or third-party platform may consult the field-to-metadata mapping to determine on which fields to search or filter. Using the above example, if the user specifies a search for "sunny" in the weather metadata, the search mechanism may search the "Make" and "Model" fields of any EXIF-based content items and search the "By-Line Title" field of any IPTC-based content items for the term "sunny," and return any matching content items in response to the search.

In an embodiment, the metadata-injection module (e.g., metadata-injection module 300) may inject metadata into content items (e.g., content item 302) according to a taxonomy. For example, as discussed above, the metadata-injection module may map a predefined taxonomy to the fields of a preexisting standard (e.g., EXIF, IPTC, etc.). As an illustration, a taxonomy for animals may map a genus to one predefined field of the standard, a species to another predefined field of the standard, etc. It should be understood that any taxonomy may be mapped in this manner, i.e., as a plurality of associations that each represent a pairing of a field within the taxonomy with a predefined field of the standard. These associations may be defined arbitrarily or may take into account the fields of the standard (e.g., making sure that the data type of the field of the taxonomy is the same as the data type of the predefined field in the standard).

Additionally or alternatively, the metadata-injection module may inject a predefined taxonomy value as metadata into a content item. The taxonomy value may identify a classification, related to the content item, from a predefined hierarchy defined by a given taxonomy. For example, a taxonomy for animals may include a particular value (e.g., a number) for a particular dog breed. The metadata-injection module may inject this taxonomy value, representing the dog breed, as metadata into a metadata field embedded in or otherwise associated with a photograph of a dog of that particular dog breed.

Non-limiting examples of various taxonomies that may be used with the metadata-injection module are provided by WAND, Inc. of Denver Colo., and are described at wand-inc.com/taxonomies.aspx. These taxonomies may include, for example, taxonomies for accounting, automotive parts and equipment, banking, building and construction management, customer service, drug development, electric and gas utility, engineering, environmental, finance and investment, fire department, food and beverage, food service equipment and supplies, general business, higher education, human resources, industrial equipment and supplies, information technology, insurance, intellectual property, K-12, legal, life insurance, local government, logistics, manufacturing, medical administration, medical condition and specialties, medical equipment and supplies, mining, news, non-profit, oil and gas, personal care products, police department, procurement, product and service, project management, property and casualty insurance, real estate, records retention, retail, sales and marketing, scientific and technical equipment, sensory, sentiment, skills, telecommunications, wastewater, and/or water utility.

As with metadata sources 220, the taxonomy or taxonomies used by metadata-injection module 300 may be extensible. In other words, each taxonomy utilized by metadata-injection module 300 may be represented as a discrete module that may be added to or removed from metadata-injection module 300 according to the particular design goals. Alternatively or additionally, the taxonomy to be used may be passed as a parameter (e.g., comprising or identifying the taxonomy) to metadata-injection module 300. Thus, each third-party developer could utilize a different taxonomy for their particular implementation or use of metadata-injection module 300, including third-party taxonomies.

A few examples of how taxonomies will now be described in greater detail. As a first example, a user could use his or her mobile user system 130 to take a photograph of a dog. This photograph may be received by metadata-injection module 300 as content item 302. Metadata-injection module 300 may pass the photograph to object-recognition module 320, which may match the dog in the photograph to an object model in reference database 392. The matched object model may be associated with a particular value (character string of numbers and/or letters) for an animal taxonomy. This particular value may represent or otherwise identify the breed of the dog, as well as implicitly or explicitly identifying the particular animal class (e.g., mammal), family (e.g., canidae), and/or the like. Object-recognition module 320 may return this taxonomy value to metadata-injection module 300, which may inject the returned taxonomy value or data derived from the returned taxonomy value (e.g., a name of the breed derived from a lookup performed by metadata-injection module 300 on a metadata source 220 using the returned taxonomy value) into a field in the metadata of the photograph. As discussed elsewhere herein, this metadata field may be predefined by the format standard of the photograph as a taxonomy field or mapped by metadata-injection module 300 as a taxonomy field. In either case, the photograph is injected with metadata that identifies a position of the subject of the photograph (i.e., the dog) within the hierarchy of a predefined taxonomy.

As a second example, a technician could use the disclosed system to perform a repair, inspection, installation, or other activity. For example, the technician could have third-party application 250, comprising, or locally or remotely interfaced with, metadata-injection module 300, installed on his or her mobile user system 130. Third-party application 250 may guide the technician through each of the tasks that, collectively, constitute the activity, for example, in the format of a checklist or template. For a cable installation, the tasks may comprise connecting a cable distribution infrastructure to a home, wiring cable through the home, installing a cable box, verifying that the cable box is working correctly, etc. For an aircraft inspection, the tasks may comprise inspecting each of a list of parts within the aircraft.

During one or more, and possibly all, of the tasks, third-party application 250 may prompt or otherwise provide the technician with the opportunity to capture a content item related to the task. Using the example of a cable installation, third-party application 250 may prompt the technician to photograph the connection between the cable distribution infrastructure and the home while guiding the technician through the connection process, may prompt the technician to photograph the installed cable box and/or an AIDC code associated with the cable box while guiding the technician through installation of the cable box, and the like. Using the example of the aircraft inspection, third-party application 250 may prompt the technician to photograph each inspected part while inspecting that part. For example, while third-party application 250 guides the technician through inspection of an aileron on the aircraft, third-party application 250 may prompt the technician to take a photograph of the aileron.

Each of these photographs may be passed to metadata-injection module 300 as content item 302, and metadata-injection module 300 may inject metadata related to a taxonomy associated with the activity into the photograph. Metadata-injection module 300 may pass the photograph to object-recognition module 320, which may match object(s) (e.g., connectors or cable box in the cable installation example, or the aileron or other aircraft parts in the aircraft inspection example) in the photograph to an object model in reference database 392. Alternatively or additionally, object-recognition module 320 may OCR an identifier (e.g., serial number on a cable box in the cable installation example, part number on an aircraft part such as the aileron in the aircraft inspection example) in the photograph to generate text representing the identifier and return the text identifier to metadata-injection module 300. Alternatively or additionally, metadata-injection module 300 may pass the photograph or an AIDC code (e.g., barcode or QR code on a cable box in the cable installation example, or on an aircraft part such as the aileron in the aircraft inspection example) extracted by object-recognition module 320 to AIDC module 365, which may return an identifier encoded in the AIDC code and/or additional information associated with that identifier or encoded within the AIDC code. It should be understood that, where an identifier of an object is obtained (e.g., serial number of a cable box, part number of an aileron), metadata-injection module 300 may derive additional data associated with the identifier, for example, by retrieving additional data (e.g., asset or inventory details) associated with the identifier from asset module 375, as discussed elsewhere herein.

In any case, metadata-injection module 300 may receive data related to the photographed object, and inject it into each photograph or other content item obtained during an activity. In the cable installation example, metadata-injection module 300 may obtain the serial number of a photograph cable box (e.g., OCR'ed by object-recognition module 320 or input via user interface 325), a model number of the cable box, dimensions of the cable box, features of the cable box etc. In the aircraft inspection example, metadata-injection module 300 may obtain a part number of a part (e.g., aileron) recognized in or OCR'ed from the photograph, dimensions of the part, prior inspection results for the part, etc.

In addition, metadata-injection module 300 may retrieve taxonomy information related to the activity and/or task being performed, and inject it into the photograph for a particular task. For example, metadata-injection module 300 may retrieve a dispatch record associated with a given activity (e.g., based on an activity identifier passed by third-party application 250 to metadata-injection module 300 or acquired by metadata-injection module 300 from another metadata source 220, such as user interface 325 or scheduling module 340), and inject information from the dispatch record into one or more photographs captured during the activity. Furthermore, metadata-injection module 300 may retrieve a task or task identifier from a taxonomy that represents the task (e.g., of installing a cable box, of inspecting an aileron) within a hierarchy of the entire activity. Metadata-injection module 300 may inject this task identifier into the photograph taken during that task. For example, task information (e.g., task identifier or information associated with the task identifier) of each task within the taxonomy of a cable installation can be injected into a corresponding photograph of that task, and task information for each part inspection within the taxonomy of an aircraft inspection can be injected into a corresponding photograph of that particular part. This type of metadata injection facilitates searching of the activity photographs (e.g., by searching based on the field representing the injected task identifier), provides the ability to verify activity results (e.g., by searching and viewing the photographs of each task first-hand), sort the photographs corresponding to each task according to the taxonomy (e.g., within the hierarchy of the taxonomy, for example, to facilitate post hoc review of the activity), audit the activity, evaluate the activity, use the activity for training purposes, in the case of the aircraft inspection, view each inspected part of a particular aircraft over time (e.g., by searching a database for a particular aircraft based on a part identifier and/or task identifier within the taxonomy), etc.

4. Content Management System

The metadata injected into content item(s) (e.g., to produce metadata-injected content item(s) 304) may be used to facilitate searching and organization of the content item(s), for example, in a content management system (CMS).

The CMS may comprise a search engine that identifies content items which match one or more criteria, such as user-specified parameters and data associations. The CMS may perform these identifications based, at least in part, on a search of the metadata injected into the content items. For instance, the CMS may receive a query comprising one or more keywords, and search the metadata injected into the stored content items to identify content items injected with metadata comprising the keyword(s). The CMS may then return results of the search. These results may comprise identifications of or references to each identified content item or the content items themselves.

The CMS may also organize the metadata-injected content items, for example, for storage and/or presentation to a user. For instance, the metadata-injected content items may be organized in a hierarchical manner based on the injected metadata. As an example, metadata-injected content items may be arranged into a plurality of "buckets" or folders based on their associated metadata. Thus, for example, all content items injected with metadata comprising "John Smith" may be organized into a bucket or folder for "John Smith." In this manner, metadata-injected content items are "tagged" and easily retrievable according to their metadata. It should be understood that, in this example, each metadata-injected content item may correspond to a plurality of buckets or folders.

The CMS may retrieve the metadata-injected content items for a user (e.g., a user of user system 130), for example, in response to a search of the content items or in response to a selection of a particular content item (e.g., from a bucket or folder). As discussed elsewhere herein, the content items may be stored remotely from user system 130 (e.g., by metadata server 110). For example, the metadata-injected content items (e.g., content item(s) 304) may be stored in cloud storage. Cloud storage represents the storage of data in virtualized storage pools which are generally hosted by third-party data centers. In cloud storage, the data may be distributed across a plurality of hardware storage devices, which themselves may be geographically distributed. The content items may be downloaded from the remote location over network(s) 120 to user system 130 as needed or requested. Alternatively, copies of the content items may be maintained at user system 130, while the remote storage serves as a backup for the locally-stored content items.

The CMS may provide a convenient user interface for users to access, organize, and search content items stored in the cloud. In an embodiment, the CMS may be provided in or interfaced with third-party application 250 (e.g., executing on a user system 130).

5. Content Streaming

In an embodiment, content items 302 may be streamed to metadata-injection module 300. For example, content items 302 could each comprise an image frame from a streaming video, or an image from a batch of streaming images. Metadata-injection module 300 may inject each frame with metadata and output each frame as metadata-injected content item 304. Alternatively, metadata-injection module 300 may accumulate metadata for each frame, and inject the entire stream (e.g., a video file comprising all of the frames) with the accumulated metadata (e.g., with duplication removed) as metadata-injected content item 304.

In an embodiment, the content items 302 may be streamed to metadata-injection module 300 in real time (i.e., as they are created), in which case the time at which each content item 302 is received may be used as the time to be input into one or more of metadata sources 220 (e.g., 310-390). Alternatively (e.g., if content items 302 are not being streamed in real time), the time relevant to each frame may be determined as an offset from a time of creation for the entire video based on a frame rate of the video. On the other hand, for many applications, that level of granularity in time may not be necessary or desired for the retrieval of metadata.

In an embodiment, a user may set the frame rate at which metadata should be injected by metadata-injection module 300 into frames of a streaming content item 302. This injection frame rate may be set via a user interface of third-party application 250 and/or user interface 325. For example, if a user sets the injection frame rate at one frame per second for a content item 302 streaming at sixty frames per second, metadata-injection module 300 may only inject metadata into one frame of streaming content item 302 per second, i.e., every sixty frames, such that intervals of fifty-nine frames are not injected with metadata. However, it should be understood that this is only an example, and that other injection frame rates and streaming frame rates are possible.

6. Metadata Streaming

In an embodiment, metadata may be streamed by one or more of metadata sources 220 (e.g., 310-390) to metadata-injection module 300. This metadata may be streamed to metadata-injection module 300 as a real-time feed from remote metadata sources (e.g., web services across one or more networks, such as external system(s) 150 across network(s) 120). Metadata-injection module 300 may pull metadata from these metadata feed(s) as needed for injection (e.g., as content items are received).

As an example, weather module 345 may stream current weather information (e.g., temperature, humidity, precipitation, etc.) to metadata-injection module 300 in real time. In this case, weather module 345 may be provided with a set of one or more locations (e.g., by third-party application 250, metadata-injection module 300, third-party platform 240, metadata server 110, etc.), such that it only streams weather information for those location(s). Alternatively, weather module 345 may stream weather information for all available locations.

As another example, news module 350 may stream current sports information (e.g., sports scores, sports news, etc.) to metadata-injection module 300 in real time. Again, news module 350 may be provided with a set of one or more locations, teams, athletes, etc., such that it only streams sports information for those location(s), team(s), athletes, etc. Alternatively, news module 350 may stream sports information for all available locations, teams, athletes, etc.

As another example, sensor(s) 355 may stream current sensor output(s) to metadata-injection module 300 in real time. For example, the sensors of a drone may stream telemetry data (e.g., acquired by the sensors while the drone is in flight) to metadata-injection module 300.

It is contemplated that metadata sources other than those highlighted herein, such as satellites, may stream metadata to metadata-injection module 300 for injection into content items 302. The streaming metadata may comprise descriptive data streams. Additionally or alternatively, the streaming metadata may include technical data streams, such as elevation, wavelength (e.g., for infrared), etc.

7. Example Use Cases

Illustrative use cases for how the disclosed third-party application (e.g., third-party application 250 or client application 132) and or metadata-injection module (e.g., metadata-injection module 300) may be utilized will now be described.

7.1. Healthcare

In an embodiment, the disclosed third-party application (e.g., third-party application 250) and/or metadata-injection module (e.g., metadata-injection module 300) can be used to manage patients, for example, at a healthcare provider's facility.

Generally patients admitted to a healthcare facility receive a patient identifier that is linked to a patient's electronic health record (HER) or other patient record stored in a database of the healthcare provider. The patient identifier may be encoded into AIDC technology, such as a QR code (e.g., printed on a wristband worn by the patient) and/or RFID tag (e.g., embedded in a wristband worn by the patient).

The healthcare provider may capture a content item from the patient for security purposes (e.g., a photograph of the patient's face, iris, fingerprint, etc.), for diagnostic purposes (e.g., a photograph of an injury, skin condition, mole, etc., an X-ray image, etc.), and/or for any other purpose (e.g., patient monitoring, training, etc.). The content item may be captured upon the patient's initial visit to the healthcare provider, and/or during subsequent visits. For example, this content item may be captured by third-party application 250 or another application executing on or interfaced with a capture device. The content item may then be passed as content item 302 to metadata-injection module 300, which may inject metadata into the content item. This metadata may comprise, without limitation, a patient identifier, information from the patient's record (e.g., electronic health record), information from a healthcare provider's record (e.g., physician's record), insurance codes (e.g., retrieved from a module similar to asset module 375), a location (e.g., received from location module 335), scheduled event details (e.g., retrieved from scheduling module 340), a duration of the visit, a prognosis and/or physician annotations (e.g., input via user interface 325), etc.

Metadata-injection module 300 may receive the patient identifier from one of the metadata sources 310-390 in any of the manners described herein. For example, the patient identifier may be captured in an audio recording (e.g., a healthcare provider speaking into a microphone of the capture device), which is converted to text by audio-to-text module 310. As another example, the patient identifier could be manually entered by a healthcare provider into user interface 325. As another example, the patient identifier may be decoded or received from an AIDC technology. For instance, the photograph of the patient may be captured while the user is holding up his or her wristband to the camera, such that the barcode printed on the patient's wristband can be identified by object-recognition module 320 and/or decoded by AIDC module 365 into the patient identifier, as described elsewhere herein. Alternatively, the photograph of the patient may be captured while third-party application 250 reads or otherwise receives information from an RFID tag (or contemporaneously with third-party application 250 receiving information from an RFID tag) embedded within the patient's wristband. The read range and/or position of the RFID reader may be set so as to only be able to read information from an RFID tag being worn by a patient in front of the capture device. Such a configuration may avoid reading another patient's RFID tag while capturing the photograph. In either case, metadata-injection module 300 may receive the patient identifier in AIDC information returned by AIDC module 365.

The metadata-injected photograph that is output from metadata-injection module 300 may be stored by the healthcare provider (e.g., in the patient's EHR or other patient record), and preferably in a database that complies with the Health Insurance Portability and Accountability Act (HIPAA)) for subsequent use.

As an example of one advantageous use of this embodiment, a healthcare provider may capture a photograph of a patient's mole as a content item 302 over the course of several visits, and easily search for the metadata-injected content items 304 based on their metadata or by viewing the patient's record to visualize how the mole has changed over time. As another example, photographs of a particular patient condition (e.g., injury, skin condition, etc.) may be injected by metadata-injection module 300 with metadata related to the patient (e.g., weight, height, age, etc.) and/or condition (e.g., etiology, diagnosis, physician annotations, etc.), but which does not identify the patient. In this case, the metadata-injected content item 304 may be used for training purposes (e.g., for medical students, for physicians, etc.). As yet another example, the metadata-injected content items 304 may be used for compliance (e.g., for the healthcare provider's malpractice insurance), auditing, and/or evidence in a malpractice lawsuit.

7.2. Telemedicine

Similarly, in an embodiment, the disclosed third-party application (e.g., third-party application 250) and/or metadata-injection module (e.g., metadata-injection module 300) can be used to manage medical services provided outside a healthcare provider's facility, such as in the case of telemedicine. One major problem for healthcare provides who utilize telemedicine is receiving payment from an insurance company for the telemedical services rendered to a patient that has a health insurance policy with the insurance company. Many insurance companies may be skeptical with respect to insurance claims for telemedical services, because its inherent inability to be verified (e.g., by hospital records) lends itself to fraud.

In an embodiment, third-party application 250 may comprise or be interfaced with telemedical software. The telemedical software may be dedicated telemedical software, or may instead be any software which enables communications between two parties (e.g., Voice-over-Internet-Protocol (Voip) software, Skype™, etc.). The telemedical software may generate an audio, visual, or audiovisual recording of a virtual patient visit, i.e., between a healthcare provider (e.g., physician) and patient (e.g., over the Internet or phone). A visual or audiovisual recording may be conducted using cameras provided at each of the healthcare provider's and patient's user systems (e.g., user systems 130). It should be understood that, in the case of a visual or audiovisual recording, the recording may comprise a plurality of images or image frames captured by the camera at the healthcare provider's system and/or by the camera at the patient's system. In addition, it should be understood that the patient's user system may not actually be owned by the patient, but may be a system at any location (e.g., a health care facility) that is remote from the healthcare provider's location, and that the visual or audiovisual recording may comprise images or image frames captured by the camera at the patient's system during a procedure being performed remotely by the healthcare provider on the patient (e.g., surgery, inspection, etc.). In the case of audio or audiovisual recording, the recording may comprise a conversation between the healthcare provider and patient.

The captured recording may be passed by the telemedical software to metadata-injection module 300 after it has been recorded (e.g., as a video file) or during recording (e.g., as a content stream, as discussed elsewhere herein). In either case, metadata-injection module 300 may inject metadata into content item 302 as a whole (e.g., into metadata fields associated with content item 302) and/or on a frame-by-frame basis (e.g., into metadata fields associated with one or more individual frames or subset of frames in content item 302). This injected metadata may comprise, without limitation, information from a physician record for the healthcare provider, information from a patient record for the patient, text of a conversation represented in content item 302 (e.g., extracted from by audio-to-text module 310 from an audio or audiovisual recording), insurance codes (e.g., retrieved from a module similar to asset module 375), a location (e.g., received from location module 335), scheduled event details (e.g., retrieved from scheduling module 340), a duration of the telemedical service, a prognosis and/or physician annotations (e.g., input via user interface 325), etc. In addition, metadata-injected content item 304 may be added to the patient's record (e.g., electronic health record), and/or otherwise stored (e.g., in database(s) 112).

Advantageously, metadata-injected content item 304 is a verifiable record of the telemedical service that was performed. Thus, metadata-injected content item 304 can be provided during an insurance audit or with an insurance claim as proof that the telemedical service was actually performed, thereby facilitating payment for the telemedical service by the insurance company to the healthcare provider.

7.3. Automated Scheduling

In an embodiment, the disclosed third-party application (e.g., third-party application 250) and/or metadata-injection module (e.g., metadata-injection module 300) can be used to automatically schedule events (e.g., in scheduling module 340).

For example, a user could use a third-party application 250 or another application executing on his or her mobile device (e.g., smartphone, tablet, etc.) to capture a photograph of a QR code. The application may convert the QR code to AIDC information, for example, using the techniques described herein with respect to object-recognition module 320 and/or AIDC module 365. It should be understood that this same example could be applied to AIDC technologies other than QR codes. For example, the mobile device may be used to capture a photograph of a barcode, capture a photograph of printed text and perform OCR on the photograph to output the text, and/or read or receive information from an RFID tag, magnetic stripe, or smart card.

Regardless of the AIDC technology used to acquire the AIDC information, the AIDC information may comprise scheduling information, including one or more event details and one or more parameters defining a time period. The application may automatically pass this scheduling information to a local or remote calendar application, which comprises, is comprised in, or is accessible (e.g., via an API, standard communication protocols, etc.) to scheduling module 340. The scheduling information may be automatically input into the calendar application as a new event entry to be managed by the calendar application, such that it is available to scheduling module 340.

Subsequently, during the time period defined in event entry, the user may use third-party application 250 to capture a photograph. Third-party application 250 may pass the photograph to metadata-injection module 300. Metadata-injection module 300 may pass the timestamp for creation of the photograph to scheduling module 340.

Scheduling module 340 may determine that the timestamp received from metadata-injection module 300 is encompassed by the time period defined in the event entry in the calendar application. Thus, scheduling module may derive scheduling information from the event entry and return that scheduling information to metadata-injection module 300.

Metadata-injection module 300 may receive the scheduling information from scheduling module 340, and automatically inject the scheduling information into the captured photograph as metadata. Thus, the captured photograph will be automatically injected with event details from the user's calendar application.

As an example, a QR code may be printed on a poster or ticket for an upcoming concert, and the QR code may encode information for the concert, such as "Los Angeles Philharmonic" at "Segerstrom Concert Hall" in "Costa Mesa, Calif." on Jan. 1, 2016 from 6:00 pm to 8:00 pm. A user may photograph the QR code printed on the poster or ticket using a camera on his or her mobile device or wearable device (e.g., Google Glass™), and the QR code may be automatically decoded into the event information and entered as a new event entry into the user's calendar application.

Subsequently, on Jan. 1, 2016 at 6:15 pm, while the user is presumably attending the concert, the user may use the camera on his or her mobile device to capture a selfie of himself or herself. Third-party application 250 may pass this photograph to metadata-injection module 300, which passes a timestamp of the photograph to scheduling module 340. Scheduling module 340 identifies the event entry based on the timestamp and returns scheduling information derived from the event entry. Metadata-injection module 300 then injects the scheduling information as metadata into the selfie. For example, the metadata-injection module 300 may embed "Los Angeles Philharmonic" into a metadata field specified a description and "Segerstrom Concert Hall, Costa Mesa, Calif." into a metadata field specified for a location. It should be understood that the timestamp may remain associated with the photograph as technical metadata.

7.4. Asset Management

In an embodiment, the disclosed third-party application (e.g., third-party application 250) and/or metadata-injection module (e.g., metadata-injection module 300) can be used to manage corporate or utility assets in the field.

For example, a worker in the field could use a third-party application 250 executing on his or her mobile user system 130 (e.g., smartphone, tablet, etc.) to capture a photograph of an asset (e.g., a wind turbine), including a QR code affixed to the asset. Third-party application 250 may pass the photograph as content item 302 to metadata-injection module 300 (e.g., during or any time after creation).

Metadata-injection module 300 may pass the photograph to object-recognition module 320. Object-recognition module 320 may match the QR code in the photograph to a model of a QR code in reference database 392, thereby identifying the QR code as a QR code. Object-recognition module 320 may return the QR code to metadata-injection module 300.

Metadata-injection module 300 may then pass the QR code to AIDC module 365. AIDC module 365 may decode the QR code into an asset identifier, and return the asset identifier to metadata-injection module 300.

Metadata-injection module 300 may then pass the asset identifier to asset module 375. Asset module 375 may send a request comprising the asset identifier over one or more networks to a remote asset database, which performs a lookup on the asset identifier and returns associated asset information. Asset module 375 may return the associated asset information to metadata-injection module 300.

Metadata-injection module 300 may parse the asset information to generate metadata from the asset information. For example, the metadata may comprise the asset identifier, a description of the asset (e.g., manufacturer, model number, serial number, etc.), inspection history, maintenance history, and/or the like. In an embodiment, the metadata may also comprise a location of the asset (e.g., received from location module 335), such as a map image with the location of the asset plotted on the map. For example, metadata-injection module 300 may retrieve location information (e.g., current GPS coordinates, map image, etc.) of mobile user system 130, at the time that the photograph is captured, from location module 335, and inject the location information into the photograph. In this manner, an organization can keep track of the location of its assets in the field over time by storing the location-injected photographs for each asset for subsequent searching and/or reporting. For example, an asset manager for the organization can do a search, based on an asset identifier, to view all of the photographs of the identified asset over time, as well as their locations (e.g., stored as an address, GPS coordinates, and/or plotted map image in the metadata for each photograph). In addition, the organization can ensure that assets are at the location at which they should be, for example, by comparing the location information in a location-injected photograph of an asset with an expected location of the asset.

Metadata-injection module 300 may then inject the metadata into content item 302 to produce metadata-injected content item 304. In embodiments which abuse standard fields, metadata-injection module 300 may consult a metadata-to-field matching and input the metadata into the mapped fields based on metadata type. Metadata-injected content item 304 may be used for tracking the location of the asset (e.g., over time), compliance (e.g., to verify the location of an asset, condition of the asset, etc.), field management, collaboration (e.g., metadata-injected content item 304 may be shared with others to arrive at a collective resolution on how to repair the asset, etc.), monitoring a repair being performed on the asset (e.g., content items comprising a pre-repair photograph of the asset, photograph(s) taken of the asset during the repair, and/or post-repair photograph of the asset), assessing or evaluating a repair completed on the asset or a potential need to replace the asset, visualization of the asset over time (e.g., content items comprising photographs of the asset at a plurality of points in time), etc.

In an alternative or additional use case, a user could utilize a scheduling application (e.g., part of third-party application 250) to schedule metadata for a planned maintenance. For example, a worker (who may or may not be the same as the user) may plan to be performing maintenance on a wind turbine between 12:00 pm and 2:00 pm on a particular day. Thus, the user may utilize the scheduling application to associate 12:00 pm to 2:00 pm on that day with metadata associated with the wind turbine and/or planned maintenance tasks. For illustration purposes, the metadata may comprise an asset identifier for the wind turbine and a description of the work to be performed.

On the day, between 12:00 pm and 2:00 pm, the worker may perform the maintenance, as planned. During the maintenance, the worker may take photographs of various features of the wind turbine, for example, using third-party application 250 executing on a mobile device (e.g., smartphone, tablet, etc.).

Third-party application 250 may pass the photographs as content items 302 to metadata-injection module 300 (e.g., during or after the time period of 12:00 pm to 2:00 pm). Metadata-injection module may consult scheduling module 340, which comprises, is comprised in, or interfaces with the scheduling application in which the planned maintenance was previously recorded. Because the timestamps of the photographs are within the time period between 12:00 pm and 2:00 pm, scheduling module returns scheduling information, including the asset identifier and work description, to metadata-injection module 300. Metadata-injection module 300 may inject the asset identifier and work description, as metadata, into content items 302.

In addition, metadata-injection module 300 may derive additional metadata, based on the asset identifier and/or work description. For example, metadata-injection module 300 may pass the asset identifier to asset module 375, which may query an asset database using the asset identifier and return asset information associated with that asset identifier in the asset database to metadata-injection module 300. Metadata-injection module 300 may further inject the received asset information into content items 302. Similarly, metadata-injection module 300 may extract task identifiers from the work description, pass these identifiers to a metadata source (e.g., similar to asset module 375), which queries a task database using the task identifiers to retrieve task descriptions and returns the task descriptions to metadata-injection module 300 to be injected into content items 302.

In an additional or alternative embodiment, metadata-injected content item 304 may comprise a composite image generated by metadata-injection module 300. The composite image may comprise a visual depiction of location metadata, such as a map image with a plot indicating the location of the asset associated with the asset identifier (e.g., acquired in any manner described herein) relative to the map image. Alternatively or additionally, the composite image may comprise visual representations of assets that are related to the asset associated with the acquired asset identifier. These visual representations may be images of other assets captured (e.g., by the worker's mobile user system 130) contemporaneously with each other or using related user interface(s), or may be images that are included in the asset information retrieved from asset module 375. As an example, an image of an asset may be composed with image(s) of component(s) of that asset, for example, that are themselves assets, and may also be embedded with metadata related to all of the depicted assets. For instance, a composite image for a wind turbine asset may comprise an image of the wind turbine composed with images of the blades, tower, and/or generator, and may also include embedded metadata related to the wind turbine, blades, tower, and/or generator. As another example, a composite image for a company vehicle may comprise an image of the vehicle composed with images of the vehicle's tires, odometer, license plate, etc., and may also include embedded metadata for one or more of the vehicle (e.g., make, model, color, year, vehicle identification number), tires (e.g., age), odometer (e.g., OCR of the odometer reading), license plate (e.g., license plate number, registration information), etc. In this manner, a single metadata-injected content item 304, generated by metadata-injection module 300, may comprise a composite image depicting a plurality of related assets and/or asset components, and may additionally comprise metadata (e.g., visually depicted in the composite image and/or in embedded or side car fields) for one or more, including all, of the depicted assets and/or asset components. Advantageously, such a metadata-injected content item 304 comprises a multitude of information for a set of related assets in a single file.

It should be understood that this is merely one illustration, and that this compositing technique may be applied advantageously in contexts other than asset management. For example, in the context of contacts, the metadata-injected content item 304 may comprise images of a plurality of related contacts and/or metadata associated with those contacts. In the context of expense auditing and/or reimbursement, explained in more detail elsewhere herein, the metadata-injected content item 304 may comprise images of receipts, attendees, odometer readings, etc. related to a business expense and/or metadata associated with the business expense. In addition, other contexts and use cases will be apparent to reviewers of the present application.

7.5. Wearable Devices

In an embodiment, the disclosed third-party application (e.g., third-party application 250) and/or metadata-injection module (e.g., metadata-injection module 300) can be used in conjunction with wearable devices (e.g., Google Glass™)

For example, the wearable device may represent user system 130, and may comprise an image acquisition device (e.g., camera) and/or sound recording device (e.g., microphone). A user, wearing the device, may utilize the device to capture a content item 302. In some embodiments, the wearable device may itself execute third-party application 250 and/or metadata-injection module 300 to inject metadata from metadata sources 220 (e.g., 310-390) into content item 302.

Alternatively, the wearable device may transmit content item 302 to another device to be stored, either contemporaneously with capture of content item 302 or subsequent to capture of content item 302. For example, the wearable device may transmit content item 302 to a smartphone in the user's pocket (e.g., using Bluetooth™ or other wireless or wired technology). In this case, the smartphone may represent user system 130 executing third-party application 250 and/or metadata-injection module 300 to inject metadata from metadata sources 220 (e.g., 310-390) into content item 302. As another example, the wearable device may transmit content item 302 directly to metadata server 110 for storage (e.g., in cloud storage). In this case, metadata server 110 may execute metadata-injection module 300 to inject metadata from metadata sources 220 (e.g., 310-390) into content item 302.

7.6. Drones

In an embodiment, the disclosed third-party application (e.g., third-party application 250) and/or metadata-injection module (e.g., metadata-injection module 300) can be used in conjunction with drones.

For example, the drone may represent user system 130 or may communicate content items 302 to a user system 130 (e.g., via a wireless interface). The drone may comprise an image acquisition device (e.g., camera) and/or sound recording device (e.g., microphone), and use these device(s) to generate content items 302 (e.g., photographs, video, audio, etc.).

In the case that the drone executes metadata-injection module 300, the metadata may be injected into each content item 302 at the drone, and the metadata-injected content item 304 may be stored on the drone for subsequent retrieval (or transmitted (e.g., via a wireless interface) to another system for storage. In the case that metadata-injection module 300 is executed remotely from the drone, the drone may transmit (e.g., via a wireless interface) each content item 302 to the system executing metadata-injection module 300, or may store each content item 302 for subsequent transfer to the system executing metadata-injection module 300.

Regardless of where metadata-injection module 300 is executed (i.e., either locally or remotely from the drone), metadata-injection module 300 may communicate with sensor(s) 355 integral or interfaced with the drone. Thus, content items 302 captured by the drone are automatically injected with sensor output captured by the drone. As discussed elsewhere herein, the timing of the sensor outputs can be synched to the time of creation for each content item 302, such that each content item 302 comprises, as metadata, the sensor output at the time that the particular content item was created. Thus, for example, each content item 302 represents both what the drone "saw" and "felt" at a given moment.

In addition, metadata-injection module 300 may retrieve DRM information from DRM module 380, and utilize the DRM information to apply a DRM scheme to content item 302. Thus, each content item 302 captured by the drone may be automatically covered by a predefined DRM scheme.

7.7. Historic Metadata

In an embodiment, since metadata-injection module 300 may utilize a timestamp representing the time that content item 302 was generated when retrieving metadata, metadata-injection module 300 may inject metadata related to the time of creation of content item 302, regardless of how long ago content item 302 was created before being received by metadata-injection module 300. Thus, regardless of whether metadata-injection module 300 receives content item 302 immediately after its creation, recently after its creation, or long after its creation, metadata-injection module 300 may inject metadata that is relevant to the time of creation.

Thus, for example, on Jan. 1, 2016, a user may utilize a third-party application 250 to load a photograph, taken using a digital camera on Jan. 1, 2000, into metadata-injection module 300. Metadata-injection module 300 may pass the timestamp, representing Jan. 1, 2000, to one or more of metadata sources 220 (e.g., 310-390) to retrieve metadata relevant to Jan. 1, 2000. For example, metadata-injection module 300 may pass the timestamp to weather module 345 to retrieve historic weather information from Jan. 1, 2000, metadata-injection module 300 may pass the timestamp to news module 350 to retrieve historic news information from Jan. 1, 2000, metadata-injection module 300 may pass the timestamp to sensor(s) 355 to retrieve historic sensor output from Jan. 1, 2000, etc. This retrieved metadata, relevant to Jan. 1, 2000, may then be injected into content item 302 to produce metadata-injected content item 304.

In some cases, the content item may predate digital acquisition, and therefore, may not have a timestamp or may not have a timestamp reflecting the actual time at which the content item was captured. For example, the user may possess a hardcopy of a photograph taken on Jan. 1, 1950, which was produced from a negative created by a non-digital camera. In this case, the user may scan the photograph into a digital format (e.g., JPEG), on Jan. 1, 2016, to produce content item 302. However, the timestamp that is created for the photograph by the scanning system will reflect time at which the photograph was scanned (i.e., Jan. 1, 2016), rather than the time at which the photograph was taken (i.e., Jan. 1, 1950). Thus, in this case, the user could alter the timestamp of content item 302. Alternatively, third-party application 250 or metadata-injection module 300 may provide a user interface into which the user may input the correct or approximate date and/or time. For instance, the user may enter user input 393, comprising the correct date, into user interface 325, which provides user input 393 to metadata-injection module 300 for injection into content item 302. In either case, content item 302 may be injected with metadata relevant to the time of capture (i.e., Jan. 1, 1950), in the same manner as discussed above, to produce metadata-injected content item 304. Thus, for example, a photograph taken at the 1984 Olympics in Los Angeles can be converted into a digital format and automatically injected with descriptive metadata, including weather and news headlines from the time, by metadata-injection module 300.

In this manner, metadata can be added retroactively to legacy material to produce metadata-injected content items 304 that are associated, in their metadata, with other content items from the same time period (e.g., to facilitate searching for content items based on time period). It should be understood that the described process for metadata-injection may be performed in bulk or batch, such that a plurality of content items are injected with metadata at the same time. In some cases, the metadata may be the same metadata. For example, a user may inject the same metadata into a plurality of photographs taken at the 1984 Olympics by providing the plurality of photographs, along with a time, to metadata-injection module 300, as discussed above.

7.8. Quick Tags

In an embodiment, the disclosed third-party application (e.g., third-party application 250) and/or metadata-injection module (e.g., metadata-injection module 300) can be used to quick-tag photographs with contact or patient information in the professional or healthcare setting, respectively.

For example, a professional may meet with a client or a physician may meet with a patient. In this setting, the professional or physician may open third-party application 250, which may provide a quick-tag input (e.g., a soft key on a user interface). The professional or physician may activate the quick-tag input and speak the name of the client or patient. The user interface of third-party application 250, comprising the quick-tag input or following activation of the quick-tag input, may also provide inputs for the professional or physician to specify one or more parameters to be used by quick-tag module 385. For instance, these parameters may include the number of photographs to which the quick-tag metadata is to be applied and/or the amount of time that the quick-tag metadata should be applied. Third-party application 250 may record the spoken name, receive the parameters, and pass the audio recording and parameters to quick-tag module 385.

Subsequently, during the meeting, the professional or physician may take photographs of or with the client or patient using third-party application 250. These photographs may be passed by third-party application 250 to metadata-injection module 300. Metadata-injection module 300 may request metadata from quick-tag module 385, and, if the parameters are satisfied (e.g., the content item is one of the number of photographs to be quick tagged or is within the time period for quick tagging), quick-tag module 385 may return the quick-tag metadata to metadata-injection module 300. Metadata-injection module 300 may receive the quick-tag metadata and embed it, possibly with other metadata, into each photograph to produce metadata-injected photographs. It should be understood that, in the case that the quick tag is received as audio, metadata-injection module 300 may pass the audio to audio-to-text module 310, which may convert the audio to text and return the text to metadata-injection module 300. In this case, metadata-injection module 300 may inject the text into each photograph instead of or in addition to the audio.

7.9. Expense Auditing

In an embodiment, the disclosed third-party application (e.g., third-party application 250) and/or metadata-injection module (e.g., metadata-injection module 300) can be used to facilitate the auditing and/or reimbursement of business expense. Specifically, metadata-injection module 300 may inject relevant metadata into images of receipts, invoices, and the like.

For example, an employee may take a client to dinner at a restaurant. The employee may utilize third-party application 250 on his mobile user system 130 to capture a photograph of a receipt from the dinner. Metadata-injection module 300 (e.g., comprised within or interfaced with third-party application 250) may receive the photograph as content item 302, and inject authorship information from authorship module 315, an employee identifier or other employee information from asset module 375, a location (e.g., an address, an address plotted on a map image, etc.) of the restaurant from location module 335 (e.g., including and/or derived from current GPS coordinates of mobile user system 130), a list of attendees or other event details from scheduling module 340, quick tags from quick-tag module 385, and/or a review of the restaurant (e.g., Yelp™: review) from news module 350 (e.g., based on current GPS coordinates of mobile user system 130 or an identifier of the restaurant from user input 393 via user interface 325 or scheduling module 340). In addition, the photograph may be OCR'ed (e.g., by object recognition module 320), and the line items, including costs and taxes, may be injected by metadata-injection module 300 as metadata into the photograph. It should be understood that these are simply illustrations, and metadata-injection module 300 may inject less, more, or different metadata than those described.

The result of the metadata injection is a metadata-injected photograph of the receipt as metadata-injected content item 304. This metadata-injected photograph may then be submitted by the employee to an accounting department of his employer for reimbursement. The metadata-injected photograph may already comprise all of the information needed for reimbursement, auditing, searching (e.g., by employee name or other identifier, cost, restaurant, location), etc., and/or serves as evidence that the employee's expense report is legitimate (e.g., that the employee was at the stated restaurant at the stated time). Accordingly, the expense reimbursement procedure is streamlined, for example, from a tedious reimbursement form that must be manually filled out by the employee with a copy or scan of the receipt, to a single photograph that the employee can email to the employer's accounting department.

In another example, metadata-injection module 300 may generate a composite metadata-injected content item 304 to be used for auditing and/or reimbursement of business expenses. Again using the illustration of an employee taking a client to dinner at a restaurant, third-party application 250, which may be installed on the employee's mobile device, may prompt or otherwise enable the employee to capture a photograph of the receipt for dinner, photographs of a starting and ending odometer reading in the instrument panel of the employee's vehicle, photograph(s) of the attendee(s) (e.g., at the restaurant), and/or other photographs (e.g., photograph(s) of the restaurant, waiter/waitress, food, drinks, etc.). Each of these photographs may be passed by third-party application 250 to metadata-injection module 300.

Metadata-injection module 300 may combine these photographs into a composite image. In an embodiment, metadata-injection module 300 combines the photographs using a template that specifies how the different photographs should be arranged. Metadata-injection module 300 may also add visual depictions of metadata to the composite image. As an illustration, the template may specify that the photograph of the receipt be placed in the upper-left corner of the composite image, the photographs of the odometer readings be placed in the upper-right corner of the composite image, and the photographs of the attendee(s) be placed in the lower-left corner of the composite image. In addition, metadata-injection module 300 may retrieve location information from location module 335 based, for example, on a GPS reading of the employee's mobile device at the time that one or more of the photographs are captured (e.g., at the time that the photograph of the receipt and/or attendee(s) are captured). The location information may comprise an image of a portion of a map with the location of the employee's mobile device (i.e., representing the location of the restaurant) plotted on the map portion, and/or a route traveled by the employee from the time he or she captured the starting odometer reading to the time that he or she captured the ending odometer reading (e.g., which may be tracked by third-party application 250 using periodic GPS readings). Alternatively or additionally, the location information could include an address corresponding to the location of the employee's mobile device (i.e., the address of the restaurant), and/or the starting and ending points of the employee's route. In any case, metadata-injection module 300 may add the location information to the composite image. For example, the template may specify that the location information (e.g., address, map image, including restaurant location and/or route) be placed in the lower-right corner of the composite image.

It should be understood that the described template, comprising a selection and arrangement of image(s) and/or visual depiction(s) of metadata, is merely one example, and that a template may define other selections and arrangements of images and visual depictions of metadata than those described. It should also be understood that a template may be used in the same or similar manner to create composite images in a variety of other use cases and examples other than business expense auditing and/or reimbursement, including any of those described herein.

Additionally, metadata-injection module 300 may add metadata to embedded fields or a sidecar file of the composite image. For example, metadata-injection module 300 may add the employee's identifier, as well as the address returned from location module 335, to the metadata. Metadata-injection module 300 may OCR the receipt (e.g., using object recognition module 320 or AIDC module 365), and add the store location and/or number, date, time, line items (e.g with descriptions and amounts of purchased items), tax amount, tip amount, and/or total amount from the receipt to the metadata. As another example, metadata-injection module 300 may OCR the odometer readings, calculate a difference between the ending and starting odometer readings, and add the difference amount to the metadata. As yet another example, metadata-injection module 300 may perform facial recognition (e.g., using object recognition module 320) and/or contact lookup (e.g., using contacts module 370) to identify names for the attendee(s) in the photograph of the attendee(s), and add their names to the metadata. Metadata-injection module could also retrieve event details, if available, from scheduling module 340. It should be understood that metadata-injection module 300 may use any of the techniques described herein to retrieve different or additional metadata to be injected into the composite image.

Once the composite image has been generated (possibly with associated metadata), metadata-injection module 300 outputs the composite image as metadata-injected content item 304. The employee and/or third-party application 250 may then provide metadata-injected content item 304, comprising the composite image, as a digital file to an accounting department of the employer (e.g., to an employee within the accounting department, or to accounting software provided by the employer). Advantageously, the composite image comprises all of the information needed to validate the business expense for tax and/or internal purposes in one visual mash-up. In addition, if metadata has been added to embedded or sidecar fields of the composite image, those fields may be searched or used to automatically populate fields of accounting software (e.g., expense amount, employee identifier, etc.).

In an embodiment, to prevent employees from faking travel expenses or locations, location module 335 may derive any of the location information discussed herein from GPS coordinates received directly from a GPS sensor in the employee's mobile device, and/or third-party application 250 may prevent or detect tampering with metadata-injected content item 304. Thus, metadata-injected content item 304, with the composite image and/or embedded location information, represents proof that the employee actually was where the employee said he or she was.

7.10. Dispatch

In an embodiment, the disclosed third-party application (e.g., third-party application 250) and/or metadata-injection module (e.g., metadata-injection module 300) can be used in conjunction with a dispatch system. Specifically, metadata-injection module 300 may inject relevant metadata into content items generated during a dispatch activity.

For example, scheduling module 340 may comprise or be interfaced with a dispatch system, which schedules and/or produces dispatch activities (e.g., for asset management, installations, repairs, inspections, emergency or non-emergency police, fire, or medical services, etc.). In this case, each dispatch activity may be a scheduled event, such that content items created by a dispatched user (e.g., a technician, paramedic, police officer, fire fighter, etc, using a mobile user system 130 executing third-party application 250) during a time period associated with the dispatch activity is automatically injected with dispatch-related metadata (e.g., details about the dispatch activity, etc.). In some instances, the time period may be defined as the current time or other start time until an indication is received (e.g., at the dispatch system) that the dispatch activity is complete (i.e., no predefined end time), to accommodate fluid or dynamic (e.g., emergency) dispatch activities for which an end time is not known ahead of time.

As an example, a dispatcher may dispatch a user to a dispatch activity, and associate a user identifier of the user with the dispatch activity. In addition, the dispatcher, user, or third-party application 250 (e.g., automatically) may associate a time period with the dispatch activity. Thereafter, when the dispatched user creates a content item 302 (e.g., takes a photograph or video using a mobile user system 130), content item 302 is passed to metadata-injection module 300. Metadata-injection module 300 may pass the user's identifier to scheduling module 340, which may perform a lookup of dispatch activities that are both associated with the user identifier and associated with a time period that encompasses the time at which content item 302 was created. Dispatch information associated with matching dispatch activities are returned to metadata-injection module 300, which injects the dispatch information (possibly with other information) as metadata into content item 302 to generate metadata-injected content item 304. This dispatch information may comprise, without limitation, a description of the dispatch activity, a location of the dispatch activity (e.g., address, GPS coordinates, plotted map image), details about the dispatch activity, taxonomy values from a taxonomy for the dispatch activity, a list of users or other individuals associated with the dispatch activity, an asset record (e.g., if the dispatch activity is an inspection, repair, or installation of an asset), a customer record (e.g., if the beneficiary of the dispatch is a consumer of a good or service provided by the dispatcher), an employee record (e.g., of the dispatched user), a patient record (e.g., if the dispatch activity is emergency medical care), results for the dispatch activity, etc. In this manner, content items related to a dispatch activity are automatically injected with metadata related to that dispatch activity.

7.11. Mobile Workforce

In an embodiment, the disclosed third-party application (e.g., third-party application 250) and/or metadata-injection module (e.g., metadata-injection module 300) can be used as or in conjunction with mobile workforce software (e.g., executing on a mobile user system 130). Specifically, metadata-injection module 300 may inject relevant metadata into content items generated by geographically-distributed employees and/or contractors within an organization.

The mobile workforce software may utilize workforce templates and/or taxonomies for managing activities performed workforce users. For example, a cable technician may utilize a template or taxonomy of the mobile workforce software during an inspection, repair, or installation of cable equipment (e.g., in accordance with a work order). This template or taxonomy may be a checklist, wizard, or the like that guides the user through performance of the activity (e.g., through various tasks that, collectively, constitute the activity). During performance of the activity, the user may generate content items 302 (e.g., in response to prompting by the mobile workforce software), such as taking a photograph, video, etc. Each of these content items 302 may be passed (e.g., by the mobile workforce software) to metadata-injection module 300, which may inject task-related, activity-related, user-related, work-order-related, and/or other workforce-related information as metadata into each content item 302. In such an embodiment, the mobile workforce software itself may act as a metadata source for metadata-injection module 300, returning the task-related, activity-related, user-related, work-order-related, and/or other workforce-related information to metadata-injection module 300 for injection into content items 302. In addition, the metadata-injected content items 304 may be attached to workflow elements, such as the work order associated with the activity being performed. Thus, work orders may be automatically populated with content items, such as photographs, which provide visualization of one or more tasks performed for the work order.

8. Example Processing Device

Figure 8:
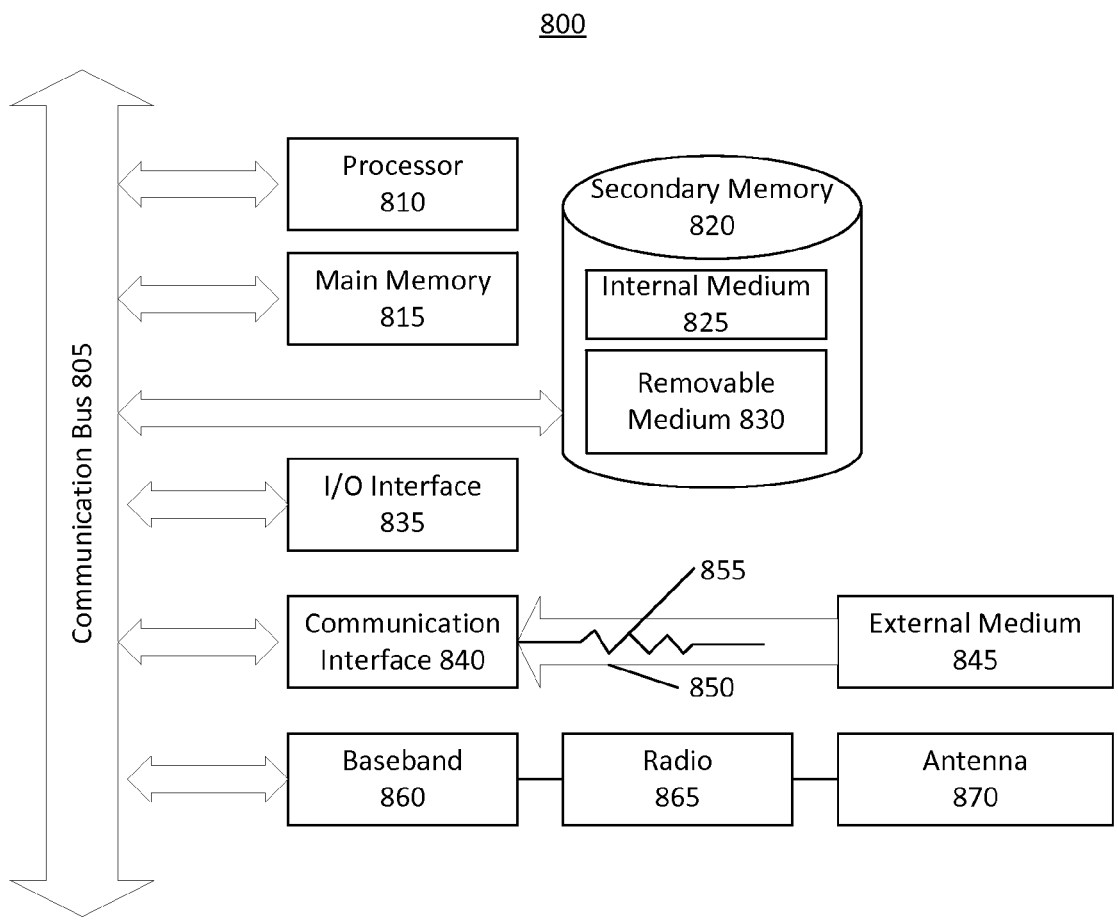
FIG. 8 illustrates a processing system on which one or more of the processes described herein may be executed, according to an embodiment.

FIG. 8 is a block diagram illustrating an example wired or wireless system 800 that may be used in connection with various embodiments described herein. For example, system 800 may be used as or in conjunction with one or more of the mechanisms, processes, methods, or functions (e.g., to store and/or execute application 132, third-party application 250, metadata-injection module 300, and/or one or more of metadata sources 220, including modules 310-390) described above, and may represent components of server 110, user system(s) 130, internal system(s) 140A, internal system(s) 140B, external system(s) 150, third-party platform 240, and/or other devices described herein. System 800 can be a server or any conventional personal computer, or any other processor-enabled device that is capable of wired or wireless data communication. Other computer systems and/or architectures may be also used, as will be clear to those skilled in the art.

System 800 preferably includes one or more processors, such as processor 810. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), graphics processing unit (GPU), an additional microprocessor or controller for dual or multiple processor systems, or a coprocessor. Such auxiliary processors may be discrete processors or may be integrated with processor 810. Examples of processors which may be used with system 800 include, without limitation, the Pentium® processor, Core i7® processor, and Xeon® processor, all of which are available from Intel Corporation of Santa Clara, Calif.

Processor 810 is preferably connected to a communication bus 805. Communication bus 805 may include a data channel for facilitating information transfer between storage and other peripheral components of system 800. Communication bus 805 may further provide a set of signals used for communication with processor 810, including a data bus, address bus, and control bus (not shown). Communication bus 805 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 800 preferably includes a main memory 815 and may also include a secondary memory 820. Main memory 815 provides storage of instructions and data for programs executing on processor 810, such as one or more of the functions and/or modules discussed above. It should be understood that programs stored in the memory and executed by processor 810 may be written and/or compiled according to any suitable language, including without limitation C/C++, Java, JavaScript, Perl, Visual Basic, .NET, and the like. Main memory 815 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 820 may optionally include an internal memory 825 and/or a removable medium 830, for example, a floppy disk drive, a magnetic tape drive, a compact disc (CD) drive, a digital versatile disc (DVD) drive, other optical drive, a flash memory drive, etc. Removable medium 830 is read from and/or written to in a well-known manner. Removable storage medium 830 may be, for example, a floppy disk, magnetic tape, CD, DVD, SD card, etc.

Removable storage medium 830 is a non-transitory computer-readable medium having stored thereon computer-executable code (i.e., software) and/or data. The computer software or data stored on removable storage medium 830 is read into system 800 for execution by processor 810.

In alternative embodiments, secondary memory 820 may include other similar means for allowing computer programs or other data or instructions to be loaded into system 800. Such means may include, for example, an external storage medium 845 and an interface 840. Examples of external storage medium 845 may include an external hard disk drive or an external optical drive, or and external magneto-optical drive.

Other examples of secondary memory 820 may include semiconductor-based memory such as programmable read-only memory (PROM), erasable programmable read-only memory (EPROM), electrically erasable read-only memory (EEPROM), or flash memory (block-oriented memory similar to EEPROM). Also included are any other removable storage media 830 and communication interface 840, which allow software and data to be transferred from an external medium 845 to system 800.

System 800 may include a communication interface 840. Communication interface 840 allows software and data to be transferred between system 800 and external devices (e.g. printers), networks, or information sources. For example, computer software or executable code may be transferred to system 800 from a network server via communication interface 840. Examples of communication interface 840 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 800 with a network or another computing device.

Communication interface 840 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 840 are generally in the form of electrical communication signals 855. These signals 855 are preferably provided to communication interface 840 via a communication channel 850. In one embodiment, communication channel 850 may be a wired or wireless network, or any variety of other communication links. Communication channel 850 carries signals 855 and can be implemented using a variety of wired or wireless communication means including wire or cable, fiber optics, conventional phone line, cellular phone link, wireless data communication link, radio frequency ("RF") link, or infrared link, just to name a few.

Computer-executable code (i.e., computer programs or software, such as the disclosed application 132 or third-party application 250) is stored in main memory 815 and/or secondary memory 820. Computer programs can also be received via communication interface 840 and stored in main memory 815 and/or secondary memory 820. Such computer programs, when executed, enable system 800 to perform the various functions, methods, and processes described above.

In this description, the term "computer-readable medium" is used to refer to any non-transitory computer readable storage media used to provide computer executable code (e.g., software and computer programs) to system 800. Examples of these media include main memory 815, secondary memory 820 (including internal memory 825, removable medium 830, and external storage medium 845), and any peripheral device communicatively coupled with communication interface 840 (including a network information server or other network device). These non-transitory computer readable mediums are means for providing executable code, programming instructions, and software to system 800.

In an embodiment that is implemented using software, the software may be stored on a computer-readable medium and loaded into system 800 by way of removable medium 830, I/O interface 835, or communication interface 840. In such an embodiment, the software is loaded into system 800 in the form of electrical communication signals 855. The software, when executed by processor 810, preferably causes processor 810 to perform the inventive features and functions previously described herein.

In an embodiment, I/O interface 835 provides an interface between one or more components of system 800 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

System 800 also includes optional wireless communication components that facilitate wireless communication over a voice and over a data network. The wireless communication components comprise an antenna system 870, a radio system 865 and a baseband system 860. In system 800, radio frequency (RF) signals are transmitted and received over the air by antenna system 870 under the management of radio system 865.

In one embodiment, antenna system 870 may comprise one or more antennae and one or more multiplexors (not shown) that perform a switching function to provide antenna system 870 with transmit and receive signal paths. In the receive path, received RF signals can be coupled from a multiplexor to a low noise amplifier (not shown) that amplifies the received RF signal and sends the amplified signal to radio system 865.

In alternative embodiments, radio system 865 may comprise one or more radios that are configured to communicate over various frequencies. In one embodiment, radio system 865 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 865 to baseband system 860.

If the received signal contains audio information, then baseband system 860 decodes the signal and converts it to an analog signal. Then, the signal is amplified and sent to a speaker. Baseband system 860 also receives analog audio signals from a microphone. These analog audio signals are converted to digital signals and encoded by baseband system 860. Baseband system 860 also codes the digital signals for transmission and generates a baseband transmit audio signal that is routed to the modulator portion of radio system 865. The modulator mixes the baseband transmit audio signal with an RF carrier signal generating an RF transmit signal that is routed to antenna system 870 and may pass through a power amplifier (not shown). The power amplifier amplifies the RF transmit signal and routes it to antenna system 870 where the signal is switched to the antenna port for transmission.

Baseband system 860 is also communicatively coupled with processor 810. Central processing unit 810 has access to data storage areas 815 and 820. Central processing unit 810 is preferably configured to execute instructions (i.e., computer programs or software) that can be stored in memory 815 or secondary memory 820. Computer programs can also be received from baseband processor 870 and stored in data storage area 815 or in secondary memory 820, or executed upon receipt. Such computer programs, when executed, enable system 800 to perform the various functions, methods, or processes as previously described. For example, data storage areas 815 may include various software modules.

Various embodiments may also be implemented primarily in hardware using, for example, components such as application-specific integrated circuits (ASICs), or field-programmable gate arrays (FPGAs). Implementation of a hardware state machine capable of performing the functions, methods, or processes described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general-purpose processor, a digital signal processor (DSP), an ASIC, FPGA, or other programmable logic device, discrete gate or transistor logic, discrete hardware components, or any combination thereof designed to perform the functions, methods, or processes described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

The above description of the disclosed embodiments is provided to enable any person skilled in the art to make or use the invention. Various modifications to these embodiments will be readily apparent to those skilled in the art, and the general principles described herein can be applied to other embodiments. Thus, it is to be understood that the description and drawings presented herein represent a presently preferred embodiment, and are therefore representative of the subject matter which is broadly contemplated by this application. It is further understood that the scope of the present application fully encompasses other embodiments that may become obvious to those skilled in the art and that the scope of the present application is accordingly not limited.

What is claimed is:

1. A method comprising using at least one hardware processor of a mobile device having a camera to:
   create one or more content items by at least capturing an image, via the camera, as at least one of the one or more content items;
   retrieve data from a plurality of metadata sources, wherein the retrieved data comprises a location corresponding to a location at which the image was captured;
   generate a visual depiction of metadata for at least one of the one or more content items based on the retrieved data, wherein the visual depiction of metadata comprises a map image having a visual indication representing the location at which the image was captured; and
   generate a composite content item comprising a single image file that combines at least a portion of each of the one or more content items, including at least a portion of the captured image of the at least one content item, with the visual depiction of the metadata, including the map image having the visual indication representing the location at which the image was captured.

2. The method of claim 1, wherein the visual depiction of metadata comprises text.

3. The method of claim 1, wherein the composite content item comprises at least one composite image comprising the at least a portion of each of the one or more content items and the visual depiction of the metadata.

4. The method of claim 3, wherein the composite content item is a video and the at least one composite image is a video frame within the video.

5. The method of claim 1, wherein the composite content item further comprises embedded metadata fields, and wherein the method further comprises using the at least one hardware processor to:
   generate metadata based on the retrieved data; and
   add the generated metadata to the embedded metadata fields of the composite content item.

6. The method of claim 1, wherein generating the composite content item comprises:
   accessing a template comprising an arrangement; and
   arranging the at least a portion of each of the one or more content items and the visual depiction of the metadata in the composite content item according to the arrangement in the template.

7. The method of claim 6, wherein the one or more content items comprise a plurality of content items.

8. The method of claim 7, wherein the plurality of content items comprises a plurality of images, and wherein the composite content item comprises a composite of at least a portion of each of the plurality of images.

9. The method of claim 7, wherein receiving the plurality of content items comprises:
   receiving a first one of the plurality of content items;
   retrieving first data from at least one of the plurality of metadata sources based on the first content item; and
   retrieving at least a second one of the plurality of content items based on the retrieved first data.

10. The method of claim 9, wherein the first content item is an image representing a first asset, and wherein the second content item is an image representing a second asset that is associated with the first asset at the at least one metadata source.

11. The method of claim 9, wherein the first content item is an image representing a first asset, and wherein the second content item is an image representing a component of the first asset that is associated with the first asset at the at least one metadata source.

12. The method of claim 7, further comprising generating one or more user interfaces that prompt a user to acquire each of the plurality of content items.

13. The method of claim 12, wherein the one or more user interfaces prompt the user to acquire an image of a receipt, such that the plurality of content items comprise an image of a receipt.

14. The method of claim 13, further comprising using the at least one hardware processor to:
   acquire text from the image of the receipt using optical character recognition; and
   add the text to metadata associated with the composite content item.

15. The method of claim 12, wherein the one or more user interfaces prompt the user to acquire an image of an odometer, such that the plurality of content items comprise a first image of an odometer.

16. The method of claim 15, wherein the one or more user interfaces prompt the user to acquire a second image of the odometer, such that the plurality of content items further comprise a second image of the odometer, and wherein the method further comprises using the at least one hardware processor to:
   convert the first image of the odometer into a first odometer reading;
   convert the second image of the odometer into a second odometer reading;
   calculate a difference between the first odometer reading and the second odometer reading; and
   add the calculated difference to metadata associated with the composite content item.

17. The method of claim 12, wherein the one or more user interfaces prompt the user to acquire each of the plurality of content items according to a predefined taxonomy that identifies a plurality of content types to be acquired.

18. A system comprising:
a camera;
at least one hardware processor; and
one or more software modules that, when executed by the at least one hardware processor,
  capture an image via the camera,
  retrieve data from a plurality of metadata sources, wherein the retrieved data comprises a location corresponding to a location at which the image was captured,
  generate a visual depiction of metadata for the captured image based on the retrieved data, wherein the visual depiction of metadata comprises a map image having a visual indication representing the location at which the image was captured, and
  generate a single image file that combines at least a portion of the captured image with the map image having the visual indication representing the location at which the image was captured.

19. A non-transitory computer-readable medium having instructions stored thereon, wherein the instructions, when executed by a processor, cause the processor to:
  capture an image via a camera;
  retrieve data from a plurality of metadata sources, wherein the retrieved data comprises a location corresponding to a location at which the image was captured;
  generate a visual depiction of metadata for the captured image based on the retrieved data, wherein the visual depiction of metadata comprises a map image having a visual indication representing the location at which the image was captured; and
  generate a single image file that combines at least a portion of the captured image with the map image having the visual indication representing the location at which the image was captured.

* * * * *